(12) United States Patent
Paterson et al.

(10) Patent No.: US 7,662,396 B2
(45) Date of Patent: *Feb. 16, 2010

(54) COMPOSITIONS AND METHODS FOR ENHANCING THE IMMUNOGENICITY OF ANTIGENS

(75) Inventors: Yvonne Paterson, Philadelphia, PA (US); Nicholas Souders, Philadelphia, PA (US); Duane Sewell, Cheltenham, PA (US); Zhen-kun Pan, Wynnewood, PA (US); Reshma Singh, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/373,528

(22) Filed: Mar. 13, 2006

(65) Prior Publication Data

US 2006/0210540 A1    Sep. 21, 2006

Related U.S. Application Data

(63) Continuation-in-part of application No. 10/835,662, filed on Apr. 30, 2004.

(51) Int. Cl.
*A61K 39/02* (2006.01)
*C12N 1/21* (2006.01)
*C07H 21/04* (2006.01)

(52) U.S. Cl. .............. 424/200.1; 424/185.1; 424/192.1; 424/234.1; 424/277.1; 435/252.3; 536/23.4; 536/23.7

(58) Field of Classification Search ........................ None
See application file for complete search history.

(56) References Cited

U.S. PATENT DOCUMENTS

| | | | |
|---|---|---|---|
| 4,521,382 A | 6/1985 | Kessick | |
| 4,777,239 A | 10/1988 | Schoolnik et al. | |
| 4,816,253 A | 3/1989 | Likhite et al. | |
| 5,262,177 A | 11/1993 | Brown et al. | |
| 5,342,774 A | 8/1994 | Boon et al. | |
| 5,681,570 A | 10/1997 | Yang et al. | |
| 5,824,538 A | 10/1998 | Branstrom et al. | |
| 5,830,702 A | 11/1998 | Portnoy et al. | |
| 5,858,682 A | 1/1999 | Gruenwald et al. | |
| 5,877,159 A | 3/1999 | Powell et al. | |
| 6,051,237 A * | 4/2000 | Paterson ................. | 424/200.1 |
| 6,479,258 B1 | 11/2002 | Short | |
| 6,565,852 B1 | 5/2003 | Paterson | |
| 6,767,542 B2 | 7/2004 | Paterson et al. | |
| 2003/0028206 A1 | 2/2003 | Shiber | |
| 2003/0202985 A1 | 10/2003 | Paterson | |
| 2004/0228877 A1 | 11/2004 | Dubensky et al. | |
| 2005/0118184 A1 | 6/2005 | Paterson et al. | |
| 2005/0129715 A1 | 6/2005 | Paterson et al. | |
| 2006/0051380 A1 | 3/2006 | Schulick et al. | |
| 2006/0093582 A1 | 5/2006 | Paterson et al. | |
| 2006/0121053 A1 | 6/2006 | Sweeney et al. | |
| 2006/0205067 A1 | 9/2006 | Paterson et al. | |

FOREIGN PATENT DOCUMENTS

| | | |
|---|---|---|
| EP | 0 902 086 | 3/1999 |
| WO | WO 93/15212 | 8/1993 |
| WO | WO 94/17192 | 8/1994 |
| WO | WO 96/14087 | 5/1996 |
| WO | WO 96/34531 | 11/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 01/27295 | 4/2001 |
| WO | WO 01/72329 | 10/2001 |
| WO | WO 03/092600 | 11/2003 |
| WO | WO 2004/006837 | 1/2004 |

OTHER PUBLICATIONS

Lebrun et al, Molecular Microbiology 21(3): 579-592, 1996.*
Paglia et al, Eur J Immunol 27: 1570-1575, 1997.*
Guzman et al, Eur J Immunol 28: 1807-1814, 1998.*
Bourquin et al, Eur J Immunol 30: 3663-3671, 2000.*
Witkowski et al, Biochemistry 38(36): 11643-50, Sep. 7, 1999.*
Seffernick et al, J Bacteriol 183 (8): 2405-10, Apr. 2001.*
Golsteyn et al, J Cell Sci 110: 1893-1906, 1997.*
Adams at al. (1992) "Cre-*lox* recombination in *Escherichia coli* cells. Mechanistic differences from the in vitro reaction." *J. Mol. Biol.* 226:661-673.
Allison et al. (1997) "Cloning and characterization of a Prevotella melaninogenica hemolysin," *Infect Immun.* 65(7):2765-71.
An et al. (1996) "A recombinant minigene vaccine containing a nonameric cytoxic-T-Lymphocyte epitope confers limited protection against *Listeria monocytogenes* infection" *Infect. Immun* 64,(5):1685-1693.
Anderson (1998) "Human gene therapy," *Nature.* Apr. 30:392(6679 Suppl):25-30.
Angelakopoulos et al. (2002) "Safety and shedding of an attenuated strain of *Listeria monocytogenes* with a deletion of actA/plcB in adult volunteers: a dose escalation study of oral inoculation," *Infect Immun.* 70(7):3592-601.
Attwood et al. (2000) "The Babel of Bioinformatics" *Science* 290(5491):471-473.
Awwad (1989) "Cyclophosphamide-induced immunologically mediated regression of a cyclophosphamide-resistant murine tumor: a consequence of eliminating precursor L3T4+ suppressor T-cells." *Cancer Res.* 49(7): 1649-1654.
Barry et al. (1992) "Pathogenicity and immunogenicity of *Listeria monocytogenes* small-plaque mutants defective for intracellular growth and cell-to-cell spread." *Infection and Immunity* 60 (4):1625-32.

(Continued)

*Primary Examiner*—Phuong Huynh
(74) *Attorney, Agent, or Firm*—Mark S. Cohen; Pearl Cohen Zedek Latzer, LLP

(57) ABSTRACT

The present invention provides recombinant polypeptides comprising an N-terminal fragment of an ActA protein or LLO protein fused to an antigen or a fragment thereof, nucleotides encoding same, recombinant vectors comprising same, and immunogenic and therapeutic methods utilizing same.

31 Claims, 28 Drawing Sheets

OTHER PUBLICATIONS

Bast et al. (1975) "Antitumor activity of bacterial infection. II. effect of *Listeria monocytogenes* on growth of a guinea pig hepatoma." *J Natl. Cancer Inst.*, 54(3): 757-761.

Bear (1986) "Tumor-specific suppressor T-cells which inhibit the in vitro generation of cytolytic T-cells from immune and early tumor-bearing host spleens." *Cancer Res.* Apr:46(4 Pt 1):1805-12.

Beatly, Dissertation Abstracts International, 2000, 61/10B:6224 Abstract Only.

Bernhard et al. (2002) "Vaccination against the HER-2/neu oncogenic protein." *Endocrine-Related Cancer*, 9:33-44.

Bielecki et al. (1990) "Bacillus subtilis expressing a haemolysin gene from *Listeria monocytogenes* can grow in mammalian cells" *Nature* 354:175-176.

Billington et al. (1997) "The Arcanobacterium (*Actinomyces*) pyogenes hemolysin, pyolysin, is a novel member of the thiol-activated cytolysin family," *J Bacteriol.* Oct.;179(19):6100-6.

Boomer at al. (1988) "Enhanced recognition of a modified peptide antigen by cytotoxic T cells specific for influenza nucleoprotein," Cell 52: 253-258.

Boon et al. (2006) "Human T cell responses against melanoma" *Annu Rev Immunol.* 24:175-208.

Bourquin et al. (2000) "Myelin oligodendrocyte glycoprotein-DNA vaccination induces antibody-mediated autoaggression in experimental autoimmune encephalomyelitis" *Eur J Immunol* 30:3663-3671.

Boyer et al. (2005) "DNA prime *Listeria* boost induces a cellular immune response to SIV antigens in the rhesus macaque model that is capable of limited suppression of SIV239 viral replication." *Virology.* Mar. 1;333(1):88-101.

Brasseur et al. (1992) "Human gene MAGE-1, which codes for a tumor-rejection antigen, is expressed by some breast tumors." *Int J Cancer* 52(5):839-841.

Brockstedt et al. (2004) "*Listeria*-based cancer vaccines that segregate immunogenictty from toxicity." *Proc Natl Aced Sci USA.* 101(38):13832-7.

Bron et al. (2004) "Identification of *Lactobacillus plantarum* genes that are induced in the gastrointestinal tract of mice." *J Bacterial.* Sep.;186(17):5721-9.

Brown et al. (1988) "Site-specific integration in *Saccharopolyspora erythraea* and multisite integration in Streptomyces lividans of actinomycete plasmid pSE101." *J. Bacteriology* 170: 2287-2295.

Bruhn et al. (2005) "Characterization of anti-self CD8 T-cell responses stimulated by recombinant *Listeria monocytogenes* expressing the melanoma antigen TRP-2." *Vaccine.* Jul. 21;23(33):4263-72.

Brundage et al. (1993) "Expression and phosphorylation of the *Listeria monocytogenes* ActA protein in mammalian cells." *Proc. Natl. Acad. Sci. USA* 90: 11890-11894.

Bubert et al. (1997) "The *Listeria monocytogenes* iap gene as an indicator gene for the study of PrfA-dependent regulation." *Mol Gen Genet.* Sep.;256(1):54-62.

Burnham (2003) "Bad bugs: good for cancer therapy?" *Drug Discovery Today* 8(2):54-55.

Calendar et al. Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=cink&cd=3&gl=us.

Camilli et al. (1993) "Dual roles of plcA in *Listeria monocytogenes* pathogenesis." *Mol. Microbiol.* 8:143-157.

Carbone (1989) "Induction of ovalbumin-specific cytotoxic T cells by in vivo peptide immunization." *J Exp Med* 169:603-612.

Carbone (1990) "Class I-restricted processing and presentation of exogenous cell-associated antigen in vivo." *J Exp Med* 171:377-387.

Chamberlain et al. (2000) "Innovations and strategies for the development of anticancer vaccines." *Expert Opinion on Pharmacatherapy* 1(4):603-614.

Courvalin et al. (1995) "Gene transfer from bacteria to mammalian cells," *C R Acad Sci III.* Dec;318(12):1207-12.

Cunto-Amesty et al. (2003) "Strategies in cancer vaccines development." *Int J Parasitol.* 33(5-6):597-613.

Dakappagari et al. (2000) "Prevention of mammary tumors with a chimeric HER-2 B-cell epitope peptide vaccine." *Cancer Res.* Jul. 15;60(14):3782-9.

Darji et al. (2003) "Induction of immune responses by attenuated isogenic mutant strains of *Listeria rnonocytogenes.*" *Vaccine* 1;21 Suppl 2:S102-9.

Darji et al. (1997) "Oral somatic transgene vaccination using attenuated *S. typhimurium*" *Cell* 91:765-775.

Darji et al. (1995) "Hyperexpression of listeriolysin in the nonpathogenic species *Listeria innocua* and high yield purification." *J Biotechnol.* Dec. 15;43(3):205-12.

Darji et al. (1995) "Listeriolysin generates a route for the presentation of exogenous antigens by major histocompatibility complex class I." *Eur J Imrnunol.* Oct;25(10):2967-71.

Darji et al. (1997) "TAP-dependent major histocompatibility complex class I presentation of soluble proteins using listeriolysin." *Eur J Immunol.* Jun;27(6):1353-9.

Decatur et al. (2000) "A PEST-like sequence in Listeriolysin O essential for *Listeria monocytogenes* pathogenicity" *Science* 290(5493):992-995.

Dermime et al. (2004) "Vaccine and antibody-directed T cell tumour immunotherapy." *Biochim Biophys Acta.* 1704(1):11-35.

Deshpande et al. (1997) "Isolation of a contect-dependent haemolysin from *Mycobacterium tuberculosis.*" *J Med Microbiol.* Mar;46(3):233-8.

Dietrich at al. (1998) "Delivery of antigen-encoding plasmid DNA into the cytosol of macrophages by attenuated suicide *Listeria monocytogenes*" *Nature Biotechnology* 15:181-185.

Dietrich et al. (2001) "From evil to good: a cytolysin in vaccine development." *Trends Microbiol.* Jan;9(1):23-8.

Dramsi at al. (1995) "Entry of *Listeria monocytogenes* into hepatocytes requires expression of InIB, a surface protein of the intemalin multigene family." *Mol Microbiol.* 16(2):251-61.

Dunn et al. (1991) "Selective radiation resistance of immunologically induced T cells as the basis for irradiation-induced T-cell-mediated regression of immunogenic tumor." *J Leukoc Biol.* 49(4): 388-396.

Ebert et al. (1990) "Selective immunosuppressive action of a factor produced by colon cancer cells." *Cancer Res.* 50(19): 6158-6161.

Ezzel (1995) "Cancer Vaccines: An Idea Whose Time Has Come?" J. NIH Res., 7:46-49.

Falk et al. (1991) "Identification of naturally processed viral nonapeptides allows their quantification in infected cells and suggests an allele-specific T cell epitope forecast" *J Exp Med.* 174(2):425-434.

Finn et al. (2003) "Cancer vaccines: between the idea and the reality." *Nature Reviews Immunology* 3:630-641.

Frankel et al. (1995) "Induction of cell-mediated immune responses to human immunodeficiency virus type 1 Gag protein by using *Listeria monocytogenes* as a live vaccine vector." *J. Immunol.* 155:4775-4782.

Frey (1993) "Rat adenocarcinoma 13762 expresses tumor rejection antigens but tumor-bearing animals exhibit tumor-specific immunosuppression." *Clin Immunol Immunopathol.* 69(2):223-233.

Friedman et al. (2000) "Induction of human immunodeficiency virus (HIV)-specific CD8 T-cell responses by *Listeria monocytogenes* and a hyperattenuated *Listeria* strain engineered to express HIV antigens." *J. Virology* 74 9987-9993.

Fu et al. (1990) "Expansion of immunoregulatory macrophages by granulocyte-macrophage colony-stimulating factor derived from a murine mammary tumor." *Cancer Res.* 50(2):227-234.

Fujii (1987) "Significance of suppressor macrophages for immunosurveillance of tumor-bearing mice." *J Natl Cancer Inst.* 78(3):509-517.

Furukawa (1993) "Nude mouse metastatic models of human stomach cancer constructed using orthotopic implantation of histologically intact tissue." *Cancer Res.* 53(5):1204-1208.

Galen et al. (2001) "Can a 'flawless' live vector vaccine strain be engineered?" *Trends Microbiol.* 9(13):372-6.

Gentschev et al. (1995) "Salmonella strain secreting active Listeriolysin changes its intracellular localization" *Infect. Immun.* 63:4202-4205.

Gentschev et al. (1996) "Development of antigen-delivery systems, based on the *Escherichia coli* hemolysin secreatiohn pathway." *Gene* 179:133-140.

Gilmore et al. (1989) "A *Bacillus cereus* cytolytic determinant, cereolysin AB, which comprises the phospholipase C and sphingomyelinase genes: nucleotide sequence and genetic linkage." *J Bacteriol.* Feb.;171(2):744-53.

Glomski et al. (2002) "The *Listeria monocytogenes* hemolysin has an acidic pH optimum to compartmentalize activity and prevent damage to infected host cells." *J Cell Biol.* Mar. 18;156(6):1029-38.

Goebel et al. (1993) "*Listeria monocytogenes*—a model system for studying the pathomechanisms of an intracellular microorganism." *Zbl. Bakt.* 278:334-347.

Goossens et al. (1992) "Induction of protective CD8+ T lymphocytes by an attenuated *Listeria monocytogenes* actA mutant." *Int Immunol.* Dec;4(12):1413-8.

Goossens et al. (1995) "Attenuated *Listeria monocytogenes* as a live vector for induction or CD8+ T cells in vivo: a study with the nucleoprotein of the lymphocytic choriomeningitis virus." *Int Immunol.* May;7(5):797-805.

Gregory et al. (1997) "Internalin B promotes the replication of *Listeria monocytogenes* in mouse hepatocytes", *Infect Immun.* 65(12):5137-41.

Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." *J Immunol.* 167(11) 6471-6479.

Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.

Gunn, Dissertation Abstracts International, 2001, 62/5B:2244 Abstract Only.

Gunn at al. (2001) "Listeriolysin—a useful cytolysln." Trends Microblo1.9(4):161-162.

Guzman et al. (1998) "Attenuated *Listeria monocytogenes* carrier strains can deliver an HIV-1 gp120 T helper epitope to MHC class II-restricted human CD4+ T cells" *European Journal of Immunology* 28:1807-1814.

Harty et al. (1996) "Primary and secondary immune responses to *Listeria monocytogenes*." *Curr Opin Immunol.* 8:526-530.

Hassan at al. (2004) "Mesothelin: a new target for immunotherapy." *Clin Cancer Res.* 10(12 Pt 1):3937-42.

Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation." *Proc Natl Acad Sci U S A.* Aug. 19;94(17):9394-9.

Hess et al. (1995) "*Listeria monocytogenes* p60 supports host cell invasion by and in vivo survival of attenuated *Salmonella typhimurium*." *Infect Immun.* May;63(5):2047-53.

Hess et al. (1996) "*Salmonella typhimurium* aroA- infection in gene-targeted immunodeficient mice: major role of CD4+ TCR-alpha beta cells and IFN-gamma in bacterial clearance independent of intracellular location." *J Immunol.* May 1;156(9):3321-6.

Hess et al. (1996) "Superior efficacy of secreted over somatic antigen display in recombinant *Salmonella* vaccine induced protection against listeriosis" *Proc. Nat. Acad. Sci.* 93:1458-1463.

Hess et al. (1997) "Protection against murine listeriosis by an attenuated recombinant *Salmonella typhimurium* vaccine strain that secretes the naturally somatic antigen superoxide dismutase." *Infect Immun.* Apr;65(4):1286-92.

Hess et al. (1998) "*Mycobacterium bovis* bacilli Calmette-Guerin strains secreting listeriolysin of *Listeria monocytogenes*." *Proc. Natl. Acad. Sci.* 95:5299-5304.

Higgins et al. (1998) "Bacterial delivery of DNA evolves." *Nat Biotechnol.* Feb;16(2):138-9.

Hodgson (2000) "Generalized transduction of serotype 1/2 and serotype 4b strains of *Listeria monocytogenes*." *Mol Microbiol.* 35(2):312-23.

Hu et al. (2004) "*Escherichia coli* expressing recombinant antigen and listeriolysin O stimulate class I-restricted CD8+ T cells following uptake by human APC." *J. Immunology* 172:1595-1601.

Huang at al. (1994) "Role of bone marrow-derived cells in presenting MHC class I-restricted tumor antigens." *Science* 264961-965.

Hussain et al. (2004) "CD4+CD25+ regulatory T cells that secrete TGFbeta and IL-10 are preferentially induced by a vaccine vector." *J Immunother.* Sep.-Oct.;27(5):339-46.

Ikonomidis at al. (1994) Abstract E-90, Abstracts, 94th General Meeting of the American Society for Microbiology. May 23-27.

Ikonomidis et al. (1994) "Delivery of a viral antigen to the class I processing and presentation oathway by *Listeria monocytogenes*" *Journal of Experimental Medicine* 180(6):2209-2218.

Jensen (1997) "Recombinant *Listeria monocytogenes* vaccination eliminates papillornsvirus-induced tumors and prevents papilloma formation from viral DNA." *J Virol.* 71(11):8467-8474.

Jensen et al. (1997) "Recombinant *Listeria monocytogenes* as a live vaccine vehicle and a probe for studying cell-mediated immunity" *Immunological Review* 158:147-157.

Jones et al. (1994) "Characterization of *Listeria monocytogenes* pathogenesis in a strain expressing perfringolysin O in place of listeriolysin O." *Infect. Immun.* 62:5608-5613.

Kaufman et al. (1999) "Impact of intracellular location of and antigen display by intracellular bacteria: implications for vaccine development" *J Immunol. Lett,* 65(1-2):81-84.

Kerksiek (1999) "T cell responses to bacterial infection" *Curr Opin. Immunol.* 1(4):400-405.

Kocks et al. (1992) "*L. monocytogenes*-induced actin assembly requires the ActA gene product" *Cell* 68(3):521-531.

Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.

Lampson et al. (1983) "Exploiting the IacZ reporter gene for quantitative analysis of disseminated tumor growth within the brain: use of the IacZ gene product as a tumor antigen, for evaluation of antigenic modulation, and to facilitate image analysis of tumor growth in situ." *Cancer Research* 53:176-182.

Lara-Tejero et al. (2004) "T cell responses to *Listeria monocytogenes*." *Curr Opin Microbiol.* 7(1):45-50.

Lasa et al. (1987) "Identification of two regions in the N-terminal domain of ActA involved in the actin comet tail formation by *Listeria monocytogenes*" *EMBO* 16(7):1531-40.

Lauer et al. (2002) "Construction, characterization, and use of two *Listeria monocytogenes* site-specific phage integration vectors." *J. Bacteriology* 184: 4177-4186.

Lauer et al. ASM Meeting. Abstract 1999.

Lebrun et al. (1996) "Internalin must be on the bacterial surface to mediate entry of *Listeria monocytogenes* into epithelial cells" *Molecular Microbiology* 21(3):579-592.

Leao et al. (1995) "A species-specific nucleotide sequence of *Mycobacterium tuberculosis* encodes a protein that exhibits hemolytic activity when expressed in *Escherichia coli*." *Infect Immun.* Nov;63 11:4301-6.

Lee et al. (1991) "Construction of single-copy integration vectors for *Staphylococcus aureus*." *Gene* 103:101-5.

Lehner et al. (1996) "Processing and delivery of peptides presented by MHC class I molecules." *Curr Opin Immunol.* 8(1):59-67.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant *Listeria monocytogenes* vaccination." *Cancer Res.* 62(8):2287-93.

Lin et al. (1996) "Treatment of established tumors with a novel vaccine that enhances Major Histocompatibility Class II presentation of tumor antigen" *Cancer Res.* 56:21-26.

Lin et al. (2002) "Oral vaccination with recombinant *Listeria monocytogenes* expressing human papillomavirus type 16 E7 can cause tumor growth in mice to regress." *Int. J Cancer.* Dec. 20;102(6):629-37.

Lingnau et al. (1995) "Expression of the *Listeria monocytogenes* EGD inlA and inlB genes, whose products mediate bacterial entry into tissue culture cell lines, by PrfA-dependent and—independent mechanisms." *Infect Immun.* Oct;63(10):3896-903.

Loeffler et al. (2006) "Comparison of different live vaccine strategies in vivo for delivery of protein antigen or antigen-encoding DNA and mRNA by virulence-attenuated *Listeria monocytogenes*." *Infect Immun.* Jul;740:3946-57.

Loessner at al. (1995) "Heterogeneous endolysins in *Listeria monocytogenes* bacteriophages: a new class of enzymes and evidence for conserved holin genes within the siphoviral lysis cassettes." *Mol Microbiol.* Jun;16(6):1231-41.

Loessner et al. (2000) "Complete nucleotide sequence, molecular analysis and genome structure of bacteriophage A118 of *Listeria monocytogenes*: implications for phage evolution." *Molecular Microbiology* 35(2):324-40.

Makela at al. (1987) Hand Book of Experimental Immunology, vol. 1, chapter 3, pp. 3.1-3.13.

Mandal at al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.

Manjili et al. (2003) "HSP110-HER2/neu chaperone complex vaccine induces protective immunity against spontaneous mammary tumors in HER-2/neu transgenic mice." *J Immunol.* Oct. 15;171(8):4054-61.

Marquis et al. (1997) "Proteolytic pathways of activation and degradation of a bacterial phospholipase C during intracellular infection by *Listeria monocytogenes.*" *J. Cell Biol.* 137:1381-1392.

Martin et al. (1986) "Nucleotide sequence of the tetM tetracycline resistance determinant of the streptococcal conjugative shuttle transposon Tn1545." *Nucleic Acid Res.* 14:7047-7058.

Marx et al. (2002) "Broad-host-range cre-lox system for antibiotic marker recycling in gram-negative bacteria." *Biotechniques.* Nov;33(5):1062-7.

McLaughlan et al. (1998) "Molecular characterization of an autolytic amidase of *Listeria monocytogenes* EGD." *Microbiology.* May:144(Pt 5):1359-67.

Mengaud et al. (1988) "Expression in *Escherichia coil* and sequence analysis of the Listeriolysin O determinant of *Listeria monocytogenes*" *Infection and Immunity* 56(4):766-772.

Mikayama et al. (1993) "Molecular cloning and functional expression of a CDNA encoding gycosylation-inhibiting factor" *Proc. Natl. Acad. Sci USA* 90:10056-10060.

Mlynarová et al. (2002) "The promiscuity of heterospecific lox sites increases dramatically in the presence of palindromIc DNA." *Gene.* Aug. 21;296(1-2)129-37.

Mollet et al. (1993) "Directed genomic integration, gene replacement, and integrative gene expression in *Streptococcus thermophilus*." *J. Bacteriology* 175:4316-4324.

Moriishi et al. (1998) "Sequence analysis of the actA gene of *Listeria monocytogenes* isolated from human" *Microbiol. Immunol.* 42(2):129-132.

Ngo et al. (1994) The Protein Folding Problem and Tertiary Structure Prediction 492-495.

Ochsenbein et al. (1999) "A comparison of T cell memory against the same antigen induced by virus versus intracellular bacteria." *Proc Natl Acad Sci U S A.* Aug. 3;96(16):9293-8.

Oscarsson et al. (1996) "Induction of haemolytic activity in *Escherichia coli* by the slyA gene product." *Mol Microbiol.* Apr;20(1)1191-9.

Paglia et al. (1997) "The defined attenuated *Listeria monocytogenes* delta mp12 mutant is an effective oral vaccine carrier to trigger a long-lasting immune response against a mouse fibrosarcoma" *Eur J Immunol* 27:1570-1575.

Palmeros et al. (2000) "A family of removable cassettes designed to obtain antibiotic-resistance-free genomic modifications of *Escherichia coli* and other bacteria." *Gene.* Apr. 18;247(1-2):255-64.

Pan (1999) "Regression of established B16F10 melanoma with a recombinant *Listeria monocytogenes* vaccine:" *Cancer Res* 59(20)5264-5269.

Pan et al. (1995) "A recombinant *Listeria monocytogenes* vaccine expressing a model tumour antigen protects mice against lethal tumour cell challenge and causes regression of established tumours." *Nature Med.* 1:471-477.

Pan et al. (1995) "Regression of established tumors in mice mediated by the oral administration of a recombinant *Listeria monocytogenes* vaccine" *Cancer Res* 55;4776-4779.

Parida et al. (1998) "Internalin B is essential for adhesion and mediates the invasion of *Listeria monocytogenes* into human endothelial cells." *Mol Microbiol.* Apr;28(1):81-93.

Paul at al. (1989) "Fundamental Immunology", Second Edition, Raven Press, 987-988.

Peng et al. (2004) "The ability of two *Listeria monocytogenes* vaccines targeting human papillomavirus-16 E7 to induce an antitumor response correlates with myeloid dendritic cell function." *J. Immunol.* 172:6030-6038.

Penichet et al. (2001) "Antibody-cytokine fusion proteins for the therapy of cancer." *J. Immunological Methods* 248:91-101.

Peters et al. (2003) "Tailoring host immune responses to *Listeria* by manipulation of virulence genes—the interface between innate and acquired immunity." *FEMS Immunol Med Microbiol.* Apr. 1;35(3):243-53.

Pfeifer et al. (1993) "Phagocytic processing of bacterial antigens for class I MHC presentation to T cells." *Nature.* Jan. 28;361(6410):359-62.

Pupa et al. (2001) "Prevention of spontaneous neu-expressing mammary tumor development in mice transgenic for rat proto-neu by DNA vaccination." *Gene Ther.* Jan;8(1):75-9.

Quénée et al. (2005) "Combined sacB-based negative selection and cre-lox antibiotic marker recycling for efficient gene deletion in pseudomonas aeruginosa." *Biotechniques.* Jan;38(1):63-7.

Radford et al. (2002) "A recombinant *E. coil* vaccine to promote MHC class I-dependent antigen presentation: application to cancer immunotherapy." *Gene Therapy* 9:1455-1463.

Radford at al. (2003) "Recombinant *E. coil* efficiently delivers antigen and maturation signals to human dendritic cells: presentation of MART1 to CD8+ T cells." *Int. J. Cancer* 105:811-819.

Raveneau et al. (1992) "Reduced virulence of a *Listeria monocytogenes* phospholipase-deficient mutant obtained by transposon insertion into the zinc metalloprotease gene." *Infect Immun.* 60: 916-921.

Realini et al. (1994) "KEKE motifs. Proposed roles in protein-protein association and presentation of peptides by MHC class I receptors" *FEBS Letters* 348:109-113.

Rechsteiner at al. (1996) "PEST sequences and regulation by proteolysis" *TIBS* 21:267-271.

Reiter et al. (1989) "Transfer RNA genes frequently serve as integration sites for prokaryotic genetic elements." *Nucleic Acids Research* 17(5)1907-14.

Renard et al. (2003) "HER-2 DNA and protein vaccines containing potent Th cell epitopes induce distinct protective and therapeutic antitumor responses in HER-2 transgenic mice." *J Immunol.* 171(3):1588-95.

Repique (1992) "Immunosuppression derived from human B-lymphoblastoid and melanoma cell lines." *Cancer Invest.* 10(3):201-208.

Roden et al. (2004) "Vaccination to prevent and treat cervical cancer." *Hum Pathol* 35(8):971-82.

Rüssmann et al. (1998) "Delivery of epitopes by the *Salmonella* type III secretion system for vaccine development." *Science.* Jul. 24;281(5376):565-8.

Safley et al. (1991) "Role of Listeriolysin-o (LLO) in the T Lymphocyte response to infection with *Listeria Monocytogenes*" *J Immunol.* 146(10):3604-3616.

Schafer et al. (1992) "Induction of a cellular immune response to a foreign antigen by a recombinant *Listeria monocytogenes* vaccine. "*J. Immunol.* 149(1):53-59.

Scheirlinck et al. (1989) "Integration and expression of alpha-amylase and endoglucanase genes in the *Lactobacillus plantarum* chromosome." *Appl Environ Microbiol* 55(9):2130-7.

Schmidt et al. (1995) "Molecular Analysis of the Plasmid-Encoded Hemolysin of *Escherichia coli* O157:H7 Strain EDL 933" *Infection and Immunity*, 63(3)1055-1061.

Scortti et al. (2007) "The PrfA virulence regulon." *Microbes Infect.* Aug;9(10):1196-207.

Sewell et al. (2004) "Regression of HPV-positive tumors treated with a new *Listeria monocytogenes* vaccine." *Arch Otolaryngol Head Neck Surg* 130:92-97.

Sewell et al. (2004) "Recombinant *Listeria* vaccines containing PEST sequences are potent immune adjuvants for the tumor-associated antigen human papillomavinis-16 E7." *Cancer Res.* Dec. 15;64(24):8821-5.

Shen et al. (1995) "Recombinant *Listeria monocytogenes* as a live vaccine vehicle for the induction of protective anti-viral cell-mediated immunity." *Proc Nat'l Acad Sci U S A.* 92(9):3987-91.

Shen at al. (1998) "*Listeria monocytogenes* as a probe to study cell-mediated immunity" *Curr. Opin. Immunol.* 10(4):450-458.

Shen et al. (1998) "Compartmentalization of bacterial antigens: differential effects on priming of CD8 T cells and protective immunity." *Cell.* Feb. 20;92(4):535-45.

Shetron-Rama et al. (2002) "Intracellular induction of *Listeria monocytogenes* actA expression." *Infect. Immun.* 70:1087-1096.

Shimizu et al. (1994) "Effects of CD4+ and CD8+ T cells in tumor-bearing mice on antibody production." *Cancer Immunol Immunother.* 38(4):272-276.

Singh et al. (2005) "Fusion to Listeriolysin O and delivery by *Listeria monocytogenes* enhances the immunogenicity of HER-2/neu and reveals subdominant epitopes in the FVB/N mouse." *J Immunol.* Sep. 15;175(6):3663-73.

Sirard et al. (1997) "Intracytoplasmic delivery of Listeriolysin 0 by a vaccinel strain of *Bacillus anthracis* induces CD8-mediated protection against *Listeria monocytogenes*" *J Immun.* 159:4435-4443.

Skoble, J. et al. (2000). "Three regions within acta promote arp2/3 complex-mediated actin nucleation and *Listeria monocytogenes* motility" *The Journal of Cell Biology* 150(3):527-537.

Skolnick et al. (2000) "From genes to protein structure and function: novel applications of computational approached in the genomic era" *Trends in Biotech.* 18(1):34-39.

Slifka et al. (1996) "Antiviral cytotoxic T-cell memory by vaccination with recombinant *Listeria monocytogenes*." *J. Virol.* 70(5):2902-10.

Smith et al. (1995) "The two distinct phospholipases C of *Listeria monocytogenes* have overlapping roles in escape from a vacuole and cell-to-cell spread." *Infect. Immun.* 63 4231-4237.

Smith et al. (1995) "Asymmetric Distribution of the *Listeria monocytogenes* ActA Protein is Required and Sufficient to Direct Actin-Based Motility" *Molecular Microbiology* 17:945-951.

Souders et al. (2006) "In vivo bactofection: *Listeria* can function as a DNA-cancer vaccine." *DNA Cell Biol.* Mar,25(3):142-51.

Stahl et al. (1984) "Replacement of the *Bacillus subtilis* subtilisin structural gene with an In vitro-derived deletion mutation." *J. Bacteriol* 158:411-418.

Starks et al. (2004) "*Listeria monocytogenes* as a vaccine vector: virulence attenuation or existing antivector immunity does not diminish therapeutic efficacy." *J. Immunology* 173:420-427.

Stitz et al. (1990) "Characterization and immunological properties of Influenza A virus nucleoprotein (NP): cell-associated NP isolated from infected cells or viral NP expressed by vaccinia recombinant virus do not confer protection." *J Gen Virol.* 71(Pt 5):1169-1179.

Strugnell et al. (1990) "Stable expression of foreign antigens from the chromosome of *Salmonella typhimurium* vaccine strains." *Gene* 88:57-63.

Stryer et al. (1998) Biochemistry, Third Edition, WH Freeman Company, New York, 31-33.

Sun et al. (1990) "Isolation of *Listeria monocytogenes* small-plaque mutants defective for intracellular growth and cell-to-cell spread." *Infect. Immun.* 58 3770-3778.

Tanabe et al. (1999) "Induction of Protective T Cells against *Listeria monocytogenes* in Mice by Immunization with a Listeriolysin O-Negative Avirulent Strain of Bacteria and Liposome-Encapsulated Listeriolysin O" *Infect. Immun.* 67(2):568-575.

Tilney et al. (1989) "Actin filaments and the growth, movement, and spread of the intracellular bacterial parasite, *Listeria monocytogenes*." *J Cell Biol.* Oct;109(4 Pt 1):1597-608.

Vasil et al. (1982) "Cloning of a phosphate-regulated hemolysin gene (phospholipase C) from *Pseudomonas aeruginosa*." *J Bacteriol.* Oct;152(1):431-40.

Vazquez-Boland et al. (1992) "Nucleotide sequence of the lecithinase operon of *Listeria monocytogenes* and possible role of lecithinase in cell-to-cell spread." *Infect. Immun.* 60:219-230.

Verch at al. (2004) "*Listeria monocytogenes*-based antibiotic resistance gene-free antigen delivery system applicable to other bacterial vectors and DNA vaccines." *Infect Immun.* Nov;72(11):6418-25.

Verma et al. (1995) "Delivery of class I and class II MHC-restricted T-cell epitopes of listeriolysin of *Listeria monocytogenes* by attenuated *Salmonella*", *Vaccine* 13(2):142-150.

Walker et al. (1994) "Tumor growth alters T cell and macrophage production of and responsiveness to granulocyte-macrophage colony-stimulating factor partial dysregulation through interleukin-10." *Cell Immunol.* 154(1):342-357.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Wei et al. (2005) "*Listeria monocytogenes* phosphatidylinositol-specific phospholipase C has evolved for virulence by greatly reduced activity on GPI anchors." *Proc. Natl. Acad. Sci. USA* 102:12927-12931.

Weidt et al. (1994) "CD8+ T lymphocyte-mediated antiviral immunity in mice as a result of injection of recombinant viral proteins." *J Immunol.* Sep. 15:153(6):2554-61.

Weiskirch et al. (1997) "*Listeria monocytogenes*: a potent vaccine vector for neoplastic and infectious disease." *Immunological Reviews* 158:159-169.

Welch et at. (1998) "Interaction of Human Arp2/3 Complex and the *Listeria monocytogenes* ActA Protein in Actin Filament Nucleation" *Science* 281:105-108.

Wirth et al. (1986) "Highly efficient protoplast transformation system for *Streptococcus faecalis* and a new *Escherichia coli-S. faecalis* shuttle vector." *J Bacteriol.* 165(3):831-6.

Wu et al. (1995) "Engineering an intracellular pathway for major histocompatibility complex class II presentation of antigens" *Cancer Res.* 56:21-26.

Young et al. (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in *Bacteriophage lysis*." *FEMS Microbiol Rev.* Aug;17(1-2):191-205.

Zhang et al. (1993) "Functional replacement of the hemolysin A transport signal by a different primary sequence." *Proc Natl Acad Sci U S A.* May 1:90(9):4211-5.

* cited by examiner

1: Liver
2: Spleen
3: Thyroid
4: Thymus
5. Cathepsin S
6. E7
7. Actin
8. Negative Control pGG5

Bacteria strain: XFL7 (PrfA)
- deletion of the transcription factor PrfA
-> hly = LLO expression is regulated by PrfA

A.

B.

COMPOSITIONS AND METHODS FOR ENHANCING THE IMMUNOGENICITY OF ANTIGENS

CROSS REFERENCE TO RELATED APPLICATIONS

This application is a Continuation-in-Part of co-pending U.S. application Ser. No. 10/835,662, filed Apr. 30, 2004, which is hereby incorporated in its entirety by reference herein.

GOVERNMENT INTERESTS

This invention was supported in part by funds from the U.S. government (National Cancer Institute Grant No. CA69632). The U.S. Government may have certain rights in this invention.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4 T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class I antigen presentation of listerial antigens. This escape is dependent upon the pore-forming sulfhydryl-activated cytolysin, listeriolysin O (LLO).

ActA is a surface-associated Listerial protein, and acts as a scaffold in infected host cells to facilitate the polymerization, assembly and activation of host actin polymers in order to propel the *Listeria* organism through the cytoplasm. Shortly after entry into the mammalian cell cytosol, *L. monocytogenes* induces the polymerization of host actin filaments and uses the force generated by actin polymerization to move, first intracellularly and then from cell to cell. A single bacterial protein, ActA is responsible for mediating actin nucleation and actin-based motility. The ActA protein provides multiple binding sites for host cytoskeletal components, thereby acting as a scaffold to assemble the cellular actin polymerization machinery. The $NH_2$ terminus of ActA binds to monomeric actin and acts as a constitutively active nucleation promoting factor by stimulating the intrinsic actin nucleation activity. ActA and hly are both members of the 10-kb gene cluster regulated by the transcriptional activator PrfA, and is upregulated approximately 226-fold in the mammalian cytosol.

There exists a long-felt need to develop compositions and methods to enhance the immunogenicity of antigens, especially antigens useful in the prevention and treatment of tumors and intracellular pathogens.

SUMMARY OF THE INVENTION

The present invention provides recombinant polypeptides comprising an N-terminal fragment of an ActA protein or LLO protein fused to an antigen or a fragment thereof, nucleotides encoding same recombinant vectors comprising same, and immunogenic and therapeutic methods utilizing same.

In one embodiment, the present invention provides a recombinant polypeptide comprising an N-terminal fragment of an ActA protein fused to an antigen or a fragment thereof, wherein the antigen is a self antigen.

In another embodiment, the present invention provides a recombinant polypeptide comprising an N-terminal fragment of a listeriolysin O (LLO) protein fused to an antigen or a fragment thereof, wherein the antigen is a self antigen.

In another embodiment the present invention provides a method of killing a cell of a HPV-transformed or Her-2-transformed tumor, comprising administering a vaccine, immunogenic composition, or vector comprising a recombinant polypeptide of the present invention, thereby killing a cell of a HPV-transformed or Her-2-transformed tumor. In another embodiment, the cell expresses an antigen present in the recombinant polypeptide. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant polypeptide of the present invention, thereby reducing a size of a HPV-transformed or Her-2-transformed tumor. In another embodiment, a cell of the tumor expresses an antigen present in the recombinant polypeptide. Each possibility represents a separate embodiment of the present invention.

In another embodiment, the present invention provides a method of treating a subject having a HPV-transformed or Her-2-transformed cancer, comprising administering a vaccine, immunogenic composition, or vector comprising a recombinant polypeptide of the present invention, whereby the vaccine elicits an immune response against the cell, thereby treating a subject having a HPV-transformed or Her-2-transformed cancer. In another embodiment, the cell expresses an antigen present in the recombinant polypeptide. Each possibility represents a separate embodiment of the present invention.

In another embodiment, the present invention provides a recombinant nucleotide encoding a recombinant polypeptide of the present invention.

In another embodiment, the present invention provides a method of killing a cell of a HPV-transformed or Her-2-transformed tumor, comprising administering a vaccine, immunogenic composition, or vector comprising a recombinant nucleotide of the present invention, thereby killing a cell of a HPV-transformed or Her-2-transformed tumor. In another embodiment, the cell expresses an antigen present on the recombinant polypeptide. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant nucleotide of the present invention, thereby reducing a size of a HPV-transformed or Her-2-transformed tumor. In another embodiment, the cell expresses an antigen present on the recombinant polypeptide. Each possibility represents a separate embodiment of the present invention.

In another embodiment, the present invention provides a method of treating a subject having, a HPV-transformed or Her-2-transformed cancer, comprising administering a vaccine, immunogenic composition, or vector comprising a recombinant nucleotide of the present invention, whereby the vaccine elicits an immune response against a cell of the tumor, thereby treating a subject having a HPV-transformed or Her-2-transformed cancer. In another embodiment, the cell expresses an antigen present on the recombinant polypeptide. Each possibility represents a separate embodiment of the present invention.

In another embodiment, the present invention provides a recombinant *Listeria* strain comprising a recombinant polypeptide of the present invention. In another embodiment, the present invention provides a recombinant *Listeria* strain comprising a recombinant nucleotide encoding a recombinant polypeptide of the present invention. In another embodiment, the *Listeria* vaccine strain is the species *Listeria monocytogenes* (LM). Each possibility represents a separate embodiment of the present invention.

In another embodiment, the present invention provides a method of killing a cell of a HPV-transformed or Her-2-transformed tumor, comprising administering a vaccine, immunogenic composition, or vector comprising a recombinant *Listeria* strain of the present invention, thereby killing a cell of a HPV-transformed or Her-2-transformed tumor. In another embodiment, the cell expresses an antigen present in the recombinant *Listeria* strain. In another embodiment, the cell expresses an antigen associated with the recombinant *Listeria* strain. In another embodiment, the cell expresses an antigen encoded by a gene or plasmid of the recombinant *Listeria* strain. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant *Listeria* strain of the present invention, thereby reducing a size of a HPV-transformed or Her-2-transformed tumor. In another embodiment, the cell expresses an antigen associated with the recombinant *Listeria* strain. In another embodiment, the cell expresses an antigen encoded by a gene or plasmid of the recombinant *Listeria* strain. Each possibility represents a separate embodiment of the present invention.

In another embodiment, the present invention provides a method of treating a subject having a HPV-transformed or Her-2-transformed cancer tumor, comprising administering a vaccine, immunogenic composition, or vector comprising a recombinant *Listeria* strain of the present invention, whereby the vaccine elicits an immune response against a cell of the cancer (tumor), thereby treating a subject having a HPV-transformed or Her-2-transformed cancer tumor. In another embodiment, the cell expresses an antigen associated with the recombinant *Listeria* strain. In another embodiment, the cell expresses an antigen encoded by a gene or plasmid of the recombinant *Listeria* strain. Each possibility represents a separate embodiment of the present invention.

In another embodiment, the present invention provides a method for overcoming an immune tolerance of a subject to an antigen-expressing HPV-transformed or Her-2-transformed tumor, comprising administering to the subject either: (a) a composition comprising a recombinant polypeptide comprising an N-terminal fragment of an ActA protein fused to the antigen or a fragment thereof; or (b) a composition comprising a recombinant nucleotide encoding the recombinant polypeptide, whereby the subject mounts an immune response against the antigen-expressing tumor, thereby overcoming an immune tolerance of a subject to an antigen-expressing HPV-transformed or Her-2-transformed tumor.

In another embodiment, the present invention provides a method of suppressing a formation of a HPV-transformed or Her-2-transformed tumor, comprising administering an effective amount of a vaccine comprising either: (a) a recombinant polypeptide comprising an N-terminal fragment of an ActA protein fused to the antigen or a fragment thereof; or (b) a recombinant nucleotide encoding the recombinant polypeptide, whereby the subject mounts an immune response against the antigen-expressing tumor, thereby suppressing a formation of a HPV-transformed or Her-2-transformed tumor.

In another embodiment, the present invention provides a method for overcoming an immune tolerance of a subject to an antigen-expressing cervical, head and neck, or breast tumor, comprising administering to the subject either: (a) a composition comprising a recombinant polypeptide comprising an N-terminal fragment of a listeriolysin O (LLO) protein fused to the antigen or a fragment thereof; or (b) a composition comprising a recombinant nucleotide encoding the recombinant polypeptide, whereby the subject mounts an immune response against the antigen-expressing tumor, thereby overcoming an immune tolerance of a subject to an antigen-expressing cervical, head and neck, or breast tumor.

In another embodiment, the present invention provides a method of suppressing a formation of a HPV-transformed or Her-2-transformed tumor, comprising administering an effective amount of a vaccine comprising a recombinant polypeptide comprising an N-terminal fragment of an LLO protein fused to the antigen or a fragment thereof, whereby the subject mounts an immune response against the antigen-expressing tumor, thereby suppressing a formation of a HPV-transformed or Her-2-transformed tumor.

In another embodiment, the present invention provides a method of suppressing a formation of a HPV-transformed or Her-2-transformed tumor, comprising administering an effective amount of a vaccine comprising either a recombinant nucleotide encoding a recombinant polypeptide, the recombinant polypeptide comprising an N-terminal fragment of an LLO protein, whereby the subject mounts an immune response against the antigen-expressing tumor, thereby suppressing a formation of a HPV-transformed or Her-2-transformed tumor.

In another embodiment, the present invention provides a method for overcoming an immune tolerance of a subject to an antigen-expressing cervical, head and neck, or breast tumor, comprising administering to the subject either: (a) a composition comprising a recombinant polypeptide comprising a PEST-like amino acid sequence derived from a prokaryotic organism, fused to the antigen or a fragment thereof, or (b) a composition comprising a recombinant nucleotide encoding the recombinant polypeptide, whereby the subject mounts an immune response against the antigen-expressing tumor, thereby overcoming an immune tolerance of a subject to an antigen-expressing cervical, head and neck, or breast tumor.

In another embodiment, the present invention provides a method of suppressing a formation of a thyroid tumor, comprising administering an effective amount of a vaccine comprising either: (a) a recombinant polypeptide comprising a PEST-like amino acid sequence derived from a prokaryotic organism, fused to the antigen or a fragment thereof, or (b) a recombinant nucleotide encoding the recombinant polypeptide, whereby the subject mounts an immune response against the antigen-expressing tumor, thereby suppressing a formation of a thyroid tumor.

DETAILED DESCRIPTION OF THE INVENTION

Figure 1:
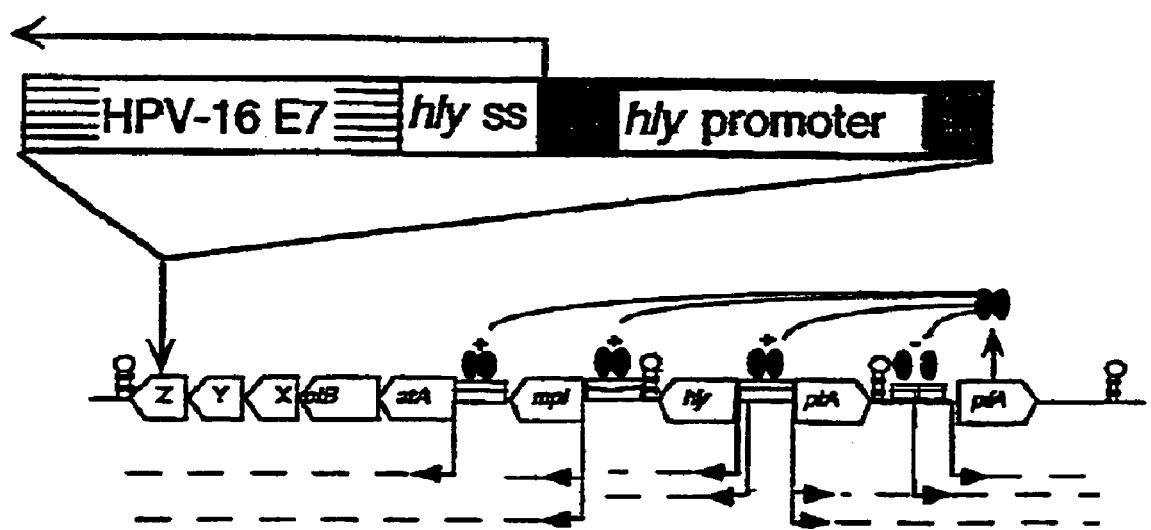
FIG. 1 is a diagram of an HPV-LLO-E7 chromosomal expression system constructed by integrating an E7 gene into the *Listeria* chromosome.

The present invention provides recombinant polypeptides comprising an N-terminal fragment of an ActA protein or LLO protein fused to an antigen or a fragment thereof, nucleotides encoding same, recombinant vectors comprising same, and immunogenic and therapeutic methods utilizing same.

In one embodiment, the present invention provides a recombinant polypeptide comprising an N-terminal fragment of an ActA protein fused to an antigen or a fragment thereof, wherein the antigen is a self antigen.

In another embodiment, the present invention provides a recombinant polypeptide comprising an N-terminal fragment of a listeriolysin O (LLO) protein fused to an antigen or a fragment thereof, wherein the antigen is a self antigen.

"Self antigen" refers, in another embodiment, to an antigen expressed on a non-tumor cell of the host. In another embodiment, the term refers to an antigen expressed on a non-embryonic, non-tumor cell of the host. In another embodiment, the term refers to an antigen expressed at a detectable level on a non-tumor cell of the host. In another embodiment, the term refers to an antigen expressed at a detectable level on a non-tumor cell of the host at any stage of development. In another embodiment, the term refers to an antigen to which the host has developed a peripheral tolerance. In another embodiment, the term refers to an antigen that has been expressed in the host at a low level, thus resulting in tolerance. In another embodiment, the term refers to an antigen that has been expressed in the host at a low level for an extended period of time, thus resulting in tolerance. Each at a possibility represents a separate embodiment of the present invention.

"Low level" refers, in another embodiment, to a level of antigen expression that is not detectable by standard antigen assays. In another embodiment, the term refers to a level that is insufficient to activate a cellular immune response. In another embodiment, the term refers to a level that is tolerogenic. In another embodiment, the term refers to a level that is similar to a level exhibited by a lysogenic virus. In another embodiment, the term refers to a level that is similar to a level exhibited by a cancer cell that has low MHC molecule expression levels. Each possibility represents another embodiment of the present invention.

"Extended period of time" refers, in another embodiment, to expression for over 2 weeks. In another embodiment, the term refers to expression for over 3 weeks. In another embodiment, the term refers to expression for over 1 month. In another embodiment, the term refers to expression for over 2 months. In another embodiment, the term refers to expression for over 3 months. In another embodiment, the term refers to expression for over 6 months. Each possibility represents another embodiment of the present invention.

In another embodiment, the present invention provides a method of killing a cell of a HPV-transformed or Her-2-transformed tumor, comprising administering a vaccine, immunogenic composition, or vector comprising a recombinant polypeptide of the present invention, thereby killing a cell of a HPV-transformed or Her-2-transformed tumor. In another embodiment, the cell expresses an antigen present in the recombinant polypeptide. In another embodiment, the cell expresses a self antigen. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant polypeptide of the present invention, thereby reducing a size of a HPV-transformed or Her-2-transformed tumor. In another embodiment, a cell of the tumor expresses an antigen present in the recombinant polypeptide. In another embodiment, the cell expresses a self antigen. Each possibility represents a separate embodiment of the present invention.

"HPV-transformed" or "Her-2 transformed" refer, in another embodiment, to a tumor dependent on HPV, a protein thereof, or Her-2 for transformed phenotype. In another embodiment, the terms refer to a tumor for which HPV, a protein thereof, or Her-2 played a significant role in oncogenic transformation. In another embodiment, the terms refer to a tumor for which HPV, a protein thereof, or Her-2 plays a significant role in maintenance of uncontrolled growth, invasiveness, or another aspect of a malignant phenotype. Each possibility represents a separate embodiment of the present invention.

In another embodiment, the present invention provides a method of treating a subject having a HPV-transformed or Her-2-transformed cancer, comprising administering a vaccine, immunogenic composition, or vector comprising a recombinant polypeptide of the present invention, whereby the vaccine elicits an immune response against the cell, thereby treating a subject having a HPV-transformed or Her-2-transformed cancer. In another embodiment, the cell expresses an antigen present in the recombinant polypeptide. In another embodiment, the cell expresses a self antigen. Each possibility represents a separate embodiment of the present invention.

In another embodiment, the present invention provides a method of killing a cell of a cervical, head and neck, or breast tumor, comprising administering a vaccine, immunogenic composition, or vector comprising a recombinant polypeptide of the present invention, thereby killing a cell of a cervical, head and neck, or breast tumor. In another embodiment, the cell expresses an antigen present in the recombinant polypeptide. In another embodiment, the cell expresses a self antigen. Each possibility represents a separate embodiment of the present invention. HPV-transformed or Her-2-transformed tumor.

In another embodiment, the present invention provides a method of reducing a size of a cervical, head and neck, or breast tumor, comprising administering a vaccine, immunogenic composition, or vector comprising a recombinant polypeptide of the present invention, thereby reducing a size of a cervical, head and neck, or breast tumor. In another embodiment, a cell of the tumor expresses an antigen present in the recombinant polypeptide. In another embodiment, the cell expresses a self antigen. Each possibility represents a separate embodiment of the present invention.

In another embodiment, the present invention provides a method of treating a subject having a cervical, head and neck, or breast cancer, comprising administering a vaccine, immunogenic composition, or vector comprising a recombinant polypeptide of the present invention, whereby the vaccine elicits an immune response against the cell, thereby treating a subject having a cervical, head and neck, or breast cancer. In another embodiment, the cell expresses an antigen present in the recombinant polypeptide. In another embodiment, the cell expresses a self antigen. Each possibility represents a separate embodiment of the present invention.

In another embodiment, the present invention provides a recombinant nucleotide encoding a recombinant polypeptide of the present invention.

"Avidity" refers, in another embodiment, to the sensitivity of a responding $CD8^+$ T cell to a peptide/MHC I complex. In another embodiment, the term refers to affinity of a TCR of a T cell to a peptide/MHC I complex. In another embodiment, avidity is measured using techniques exemplified in the Examples herein. In another embodiment, avidity is measured using any other suitable method known in the art. Each possibility represents a separate embodiment of the present invention.

In another embodiment, the present invention provides a recombinant vaccine vector comprising a recombinant polypeptide of the present invention. In another embodiment, the present invention provides a recombinant vaccine vector comprising a recombinant nucleotide of the present invention. Each possibility represents a separate embodiment of the present invention.

In another embodiment, the present invention provides a method of killing a cell of a HPV-transformed or Her-2-transformed tumor, comprising administering a vaccine, immunogenic composition, or vector comprising a recombinant nucleotide of the present invention, thereby killing a cell of a HPV-transformed or Her-2-transformed tumor. In another embodiment, the cell expresses a self antigen. In another embodiment, the cell expresses an antigen present on the recombinant polypeptide. In another embodiment, the cell expresses a self antigen. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant nucleotide of the present invention, thereby reducing a size of a HPV-transformed or Her-2-transformed tumor. In another embodiment, the cell expresses an antigen present on the recombinant polypeptide. In another embodiment, the cell expresses a self antigen. Each possibility represents a separate embodiment of the present invention.

In another embodiment, the present invention provides a method of treating a subject having a HPV-transformed or Her-2-transformed cancer, comprising administering a vaccine, immunogenic composition, or vector comprising a recombinant nucleotide of the present invention, whereby the vaccine elicits an immune response against a cell of the tumor, thereby treating a subject having a HPV-transformed or Her-2-transformed cancer. In another embodiment, the cell expresses an antigen present on the recombinant polypeptide. In another embodiment, the cell expresses a self antigen. Each possibility represents a separate embodiment of the present invention.

In another embodiment, the present invention provides a method of killing a cell of a cervical, head and neck, or breast tumor, comprising administering a vaccine, immunogenic composition, or vector comprising a recombinant nucleotide of the present invention, thereby killing a cell of a cervical, head and neck, or breast tumor. In another embodiment, the cell expresses a self antigen. In another embodiment, the cell expresses an antigen present on the recombinant polypeptide. In another embodiment, the cell expresses a self antigen. Each possibility represents a separate embodiment of the present invention.

In another embodiment, the present invention provides a method of reducing a size of a cervical, head and neck, or breast tumor, comprising administering a vaccine, immunogenic composition, or vector comprising a recombinant nucleotide of the present invention, thereby reducing a size of a cervical, head and neck, or breast tumor. In another embodiment, the cell expresses an antigen present on the recombinant polypeptide. In another embodiment, the cell expresses a self antigen. Each possibility represents a separate embodiment of the present invention.

In another embodiment, the present invention provides a method of treating a subject having a cervical, head and neck, or breast cancer, comprising administering a vaccine, immunogenic composition, or vector comprising a recombinant nucleotide of the present invention, whereby the vaccine elicits an immune response against a cell of the tumor, thereby treating a subject having a cervical, head and neck, or breast cancer. In another embodiment, the cell expresses an antigen present on the recombinant polypeptide. In another embodiment, the cell expresses a self antigen. Each possibility represents a separate embodiment of the present invention.

In another embodiment, the present invention provides a recombinant *Listeria* strain comprising a recombinant polypeptide of the present invention. In another embodiment, the present invention provides a recombinant *Listeria* strain comprising a recombinant nucleotide encoding a recombinant polypeptide of the present invention. In another embodiment, the *Listeria* vaccine strain is the species *Listeria monocytogenes* (LM). Each possibility represents a separate embodiment of the present invention.

In another embodiment, the present invention provides a method of killing a cell of a HPV-transformed or Her-2-transformed tumor, comprising administering a vaccine, immunogenic composition, or vector comprising a recombinant *Listeria* strain of the present invention, thereby killing a cell of a HPV-transformed or Her-2-transformed tumor. In another embodiment, the cell expresses an antigen present in the recombinant *Listeria* strain. In another embodiment, the cell expresses an antigen associated with the recombinant

*Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method of reducing a size of a HPV-transformed or Her-2-transformed tumor, comprising administering a vaccine, immunogenic composition, or vector comprising a recombinant *Listeria* strain of the present invention, thereby reducing a size of a HPV-transformed or Her-2-transformed tumor. In another embodiment, the cell expresses an antigen associated with the recombinant *Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method of treating a subject having a HPV-transformed or Her-2-transformed cancer, comprising administering a vaccine, immunogenic composition, or vector comprising a recombinant *Listeria* strain of the present invention, whereby the vaccine elicits an immune response against a cell of the tumor, thereby treating a subject having a HPV-transformed or Her-2-transformed cancer. In another embodiment, the cell expresses an antigen associated with the recombinant *Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method of killing a cell of a cervical, head and neck, or breast tumor, comprising administering a vaccine, immunogenic composition, or vector comprising a recombinant *Listeria* strain of the present invention, thereby killing a cell of a cervical, head and neck, or breast tumor. In another embodiment, the cell expresses an antigen present in the recombinant *Listeria* strain. In another embodiment, the cell expresses an antigen associated with the recombinant *Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method of reducing a size of a cervical, head and neck, or breast tumor, comprising administering a vaccine, immunogenic composition, or vector comprising a recombinant *Listeria* strain of the present invention, thereby reducing a size of a cervical, head and neck, or breast tumor. In another embodiment, the cell expresses an antigen associated with the recombinant *Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method of treating a subject having a cervical, head and neck, or breast cancer, comprising administering a vaccine, immunogenic composition, or vector comprising a recombinant *Listeria* strain of the present invention, whereby the vaccine elicits an immune response against a cell of the tumor, thereby treating a subject having a cervical, head and neck, or breast cancer. In another embodiment, the cell expresses an antigen associated with the recombinant *Listeria* strain. In another embodiment, the cell expresses an antigen encoded by a gene or plasmid of the recombinant *Listeria* strain. In another embodiment, the cell expresses a self antigen. Each possibility represents a separate embodiment of the present invention.

In another embodiment, the present invention provides a method for overcoming an immune tolerance of a subject to an antigen-expressing cervical, head and neck, or breast tumor, comprising administering to the subject either: (a) a composition comprising a recombinant polypeptide comprising an N-terminal fragment of an ActA protein fused to the antigen or a fragment thereof, or (b) a composition comprising a recombinant nucleotide encoding the recombinant polypeptide, whereby the subject mounts an immune response against the antigen-expressing tumor, thereby overcoming an immune tolerance of a subject to an antigen-expressing cervical, head and neck, or breast tumor.

"Tolerance" refers, in another embodiment, to a lack of responsiveness of the host to an antigen. In another embodiment, the term refers to a lack of detectable responsiveness of the host to an antigen. In another embodiment, the term refers to a lack of immunogenicity of an antigen in a host. In another embodiment, tolerance is measured by lack of responsiveness in an in vitro CTL killing assay. In another embodiment, tolerance is measured by lack of responsiveness in a delayed-type hypersensitivity assay. In another embodiment, tolerance is measured by lack of responsiveness in any other suitable assay known in the art. In another embodiment, tolerance is determined or measured as depicted in the Examples herein. Each possibility represents another embodiment of the present invention.

"Overcome" refers, in another embodiment, to a reversible of tolerance by a vaccine. In another embodiment, the term refers to conferment of detectable immune response by a vaccine. In another embodiment, overcoming of immune tolerance is determined or measured as depicted in the Examples herein. Each possibility represents another embodiment of the present invention.

In another embodiment, the antigen present on a recombinant polypeptide, recombinant nucleotide, or recombinant *Listeria* strain of the present invention is HPV-E7. In another embodiment, the antigen is HPV-E6. In another embodiment, the antigen is Her-2. In another embodiment, the antigen is NY-ESO-1. In another embodiment, the antigen is telomerase. In another embodiment, the antigen is SCCE. In another embodiment, the antigen is HMW-MAA. In another embodiment, the antigen is a tumor-associated antigen. In another embodiment, the antigen is an infectious disease antigen.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Muc1, or pSA.

In other embodiments, the antigen is associated with one of the following diseases; cholera, diphtheria, Haemophilus, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

In other embodiments, the antigen is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, gp100, a MART1 antigen associated with melanoma, or the PSA antigen associated with prostate cancer.

In another embodiment, an antigen of methods and compositions of the present invention is required for a tumor phenotype. In another embodiment, the antigen is necessary for transformation of a tumor cell. In another embodiment, tumor cells that lose expression of the antigen lose their uncontrolled growth, invasiveness, or another feature of malignancy. Each possibility represents a separate embodiment of the present invention.

In another embodiment, an antigen of methods and compositions of the present invention shares complete homology with the antigen expressed by the Listerial vector. In another embodiment, the antigen is highly homologous to the antigen expressed by the Listerial vector. "Highly homologous" refers, in another embodiment, to a homology of greater than 90%. In another embodiment, the term refers to a homology of greater than 92%. In another embodiment, the term refers to a homology of greater than 93%. In another embodiment, the term refers to a homology of greater than 94%. In another embodiment, the term refers to a homology of greater than 95%. In another embodiment, the term refers to a homology of greater than 96%. In another embodiment, the term refers to a homology of greater than 97%. In another embodiment, the term refers to a homology of greater than 98%. In another embodiment, the term refers to a homology of greater than 99%. In another embodiment, the term refers to a homology of 100%. Each possibility represents a separate embodiment of the present invention.

In another embodiment, a fragment of one of the above antigens is present on a recombinant polypeptide, recombinant nucleotide, or recombinant Listeria strain of the present invention.

The skilled artisan will appreciate that methods and compositions of the present invention can utilized any of the above antigens. Each of the above antigens represents a separate embodiment of the present invention.

In another embodiment, the N-terminal fragment of an ActA protein has the sequence set forth in SEQ ID NO:23:

```
MRAMMVVFITANCITINPDIIFAATDSEDSSLNTDEWEEEEKTEEQPSEVN
TGPRYETAREVSSRDIKELEKSNKVRNTNKADLIAMLKEKAEKGPNINNNN
SEQTENAAINEEASGADRPAIQVERRHPGLPSDSAAEIKKRRKAIASSDSE
LESLTYPDKPTKVNKKKVAKESVADASESDLDSSMQSADESSPQPLKANQQ
PFFPKVFKKIKDAGKWVRDKIDENPEVKKAIVDKSAGLIDQLLTKKKSEEV
NASDFPPPPTDEELRLALPETPMLLGFNAPATSEPSSFEFPPPPTDEELRL
ALPETPMLLGFNAPATSEPSSFEFPPPPTEDELEIIRETASSLDSSFTRGD
LASLRNAINRHSQNFSDFPPIPTEEELNGRGGRP.
```

In another embodiment, the N-terminal fragment of an ActA protein has the sequence set forth in SEQ ID NO: 23. In another embodiment, the ActA fragment is any other ActA fragment known in the art. Each possibility represents a separate embodiment of the present invention.

In another embodiment, the recombinant nucleotide of the present invention comprises the nucleotide sequence encoding the amino acid sequence set forth in SEQ ID NO:24. In

```
Atgcgtgcgatgatggtggttttcattactgccaattgcattacgattaa
ccccgacataatatttgcagcgacagatagcgaagattctagtctaaaca
cagatgaatgggaagaagaaaaaacagaagagcaaccaagcgaggtaaat
acgggaccaagatacgaaactgcacgtgaagtaagttcacgtgatattaa
agaactagaaaaatcgaataaagtgagaaatacgaaccaaagcagacctaa
tagcaatgttgaaagaaaaagcagaaaaaggtccaaatatcaataataac
aacagtgaacaaactgagaatgcggctataaatgaagaggcttcaggagc
cgaccgaccagctatacaagtggagcgtcgtcatccaggattgccatcgg
atagcgcagcggaaattaaaaaaagaaggaaagccatagcatcatcggat
agtgagcttgaaagccttacttatccggataaaccaacaaaagtaaataa
gaaaaaagtggcgaaagagtcagttgcggatgcttctgaaagtgacttag
attctagcatgcagtcagcagatgagtcttcaccacaacctttaaaagca
aaccaacaaccattttccctaaagtatttaaaaaaataaaagatgcggg
gaaatgggtacgtgataaaatcgacgaaaatcctgaagtaaagaaagcga
ttgttgataaaagtgcagggttaattgaccaattattaaccaaaaagaaa
agtgaagaggtaaatgcttcggacttcccgccaccacctacggatgaaga
gttaagacttgctttgccagagacaccaatgcttcttggttttaatgctc
ctgctacatcagaaccgagctcattcgaatttccaccaccacctacggat
gaagagttaagacttgctttgccagagacgccaatgcttcttggttttaa
tgctcctgctacatcggaaccgagctcgttcgaatttccaccgcctccaa
cagaagatgaactagaaatcatccgggaaacagcatcctcgctagattct
agttttacaagaggggatttagctagtttgagaaatgctattaatcgcca
tagtcaaaatttctctgatttcccaccaatcccaacagaagaagagttga
acgggagaggcggtagacca.
``` another embodiment, the recombinant nucleotide comprises any other sequence that encodes a fragment of an ActA protein. Each possibility represents a separate embodiment of the present invention.

In another embodiment, the present invention provides a method of suppressing a formation of a HPV-transformed or Her-2-transformed tumor, comprising administering an effective amount of a vaccine comprising either: (a) a recombinant polypeptide comprising an N-terminal fragment of a protein fused to the antigen or a fragment thereof, or (b) a recombinant nucleotide encoding the recombinant polypeptide, whereby the subject mounts an immune response against the antigen-expressing tumor, thereby suppressing a formation of a HPV-transformed or Her-2-transformed tumor.

In another embodiment, the present invention provides a method of suppressing a formation of a thyroid tumor, comprising administering an effective amount of a vaccine comprising either: (a) a recombinant polypeptide comprising an N-terminal fragment of a protein fused to the antigen or a fragment thereof; or (b) a recombinant nucleotide encoding the recombinant polypeptide, whereby the subject mounts an immune response against the antigen-expressing tumor, thereby suppressing a formation of a thyroid tumor.

In another embodiment, the present invention provides a method for overcoming an immune tolerance of a subject to an antigen-expressing cervical, head and neck, or breast tumor, comprising administering to the subject either: (a) a composition comprising a recombinant polypeptide comprising an N-terminal fragment of a listeriolysin O (LLO) protein fused to the antigen or a fragment thereof, or (b) a composition comprising a recombinant nucleotide encoding the recombinant polypeptide, whereby the subject mounts an immune response against the antigen-expressing tumor, thereby overcoming an immune tolerance of a subject to an antigen-expressing cervical, head and neck, or breast tumor.

The LLO protein utilized to construct vaccines of the present invention has, in another embodiment, the sequence:

```
MKKIMLVFITLILVSLPIAQQTEAKDASAFNKENSISSMAPPASPPASPK
TPIEKKHADEIDKYIQGLDYNKNNVLVYHGDAVTNVPPRKGYKDGNEYIVVEKKKK
SINQNNADIQVVNAISSLTYPGALVKANSELVENQPDVLPVKRDSLTLSIDLPGMT
NQDNKIVVKNATKSNVNNAVNTLVERWNEKYAQAYPNVSAKIDYDDEMAYSESQLI
AKFGTAFKAVNNSLNVNFGAISEGKMQEEVISFKQIYYNVNVNEPTRPSRFFGKAV
TKEQLQALGVNAENPPAYISSVAYGRQVYLKLSTNSHSTKVKAAFDAAVSGKSVSG
DVLTNIIKNSSFKAVIYGGSAKDEVQIIDGNLGDLRDILKKGATFNRETPGVPIAY
TTNFLKDNELAVIKNNSEYIETTSKAYTDGKINIDHSGGYVAQFNISWDEVNYDPE
GNEIVQHKNWSENNKSKLAHFTSSIYLPGNARNINVYAKECTGLAWEWWRTVIDDR
NLPLVKNRNISIWGTTLYPKYSNKVDNPIE
```

(GenBank Accession No. P13128; SEQ ID NO: 24; nucleic acid sequence is set forth in GenBank Accession No. X15127). The first 25 amino acids of the proprotein corresponding to this sequence are the signal sequence and are cleaved from LLO when it is secreted by the bacterium. Thus, in this embodiment, the full length active LLO protein is 504 residues long.

In another embodiment, the N-terminal fragment of an LLO protein utilized in compositions and methods of the present invention has the sequence:

```
Mkkimlvfitlilvslpiaqqteakdasafnkensi   (SEQ ID NO:25)
ssvappasppaspktpiekkhadeidkyiqgldynk
nnvlvyhgdavtnvpprkgykdgneyivvekkkksi
nqnnadiqvvnaissltypgalvkanselvenqpdv
lpvkrdsltlsidlpgmtnqdnkivvknatksnvnn
avntlverwnekyaqaysnvsakidyddemaysesq
liakfgtafkavnnslnvnfgaisegkmqeevisfk
qiyynvnvneptrpsrffgkavtkeqlqalgvnaen
ppayissvaygrqvylklstnshstkvkaafdaavs
gksvsgdveltniiknssfkaviyggsakdevqiid
gnlgdlrdilkkgatfnretpgvpiayttnflkdne
laviknnseyiettskaytdgkinidhsggyvaqfn
iswdevnyd.
```

In another embodiment, the LLO fragment has the sequence:

```
Mkkimlvfitlilvslpiaqqteakdasafnkensi   (SEQ ID NO:23)
ssvappasppaspktpiekkhadeidkyiqgldynk
nnvlvyhgdavtnvpprkgykdgneyivvekkkksi
nqnnadiqvvnaissltypgalvkanselvenqpdv
lpvkrdsltlsidlpgmtnqdnkivvknatksnvnn
avntlverwnekyaqaysnvsakidyddemaysesq
liakfgtafkavnnslnvnfgaisegkmqeevisfk
qiyynvnvneptrpsrffgkavtkeqlqalgvnaen
ppayissvaygrqvylklstnshstkvkaafdaavs
gksvsgdveltniiknssfkaviyggsakdevqiid
gnlgdlrdilkkgatfnretpgvpiayttnflkdne
laviknnseyiettskaytd.
```

In another embodiment, the LLO fragment is any other LLO fragment known in the art. Each possibility represents a separate embodiment of the present invention.

In another embodiment, the present invention provides a method of suppressing a formation of a HPV-transformed or Her-2-transformed tumor, comprising administering an effective amount of a vaccine comprising a recombinant polypeptide comprising an N-terminal fragment of an LLO protein fused to the antigen or a fragment thereof, whereby the subject mounts an immune response against the antigen-expressing tumor, thereby suppressing a formation of a HPV-transformed or Her-2-transformed tumor.

In another embodiment, the present invention provides a method of suppressing a formation of a HPV-transformed or Her-2-transformed tumor, comprising administering an effective amount of a vaccine comprising either a recombinant nucleotide encoding a recombinant polypeptide, the recombinant polypeptide comprising an N-terminal fragment of an LLO protein, whereby the subject mounts an immune response against the antigen-expressing tumor, thereby suppressing a formation of a HPV-transformed or Her-2-transformed tumor.

In another embodiment, the present invention provides a method of suppressing a formation of a thyroid tumor, comprising administering an effective amount of a vaccine comprising a recombinant polypeptide comprising an N-terminal fragment of an LLO protein fused to the antigen or a fragment thereof, whereby the subject mounts an immune response against the antigen-expressing tumor, thereby suppressing a formation of a thyroid tumor.

In another embodiment, the present invention provides a method of suppressing a formation of a thyroid tumor, comprising administering an effective amount of a vaccine comprising either a recombinant nucleotide encoding a recombinant polypeptide, the recombinant polypeptide comprising an N-terminal fragment of an LLO protein, whereby the subject mounts an immune response against the antigen-expressing tumor, thereby suppressing a formation of a thyroid tumor.

In another embodiment, the present invention provides a method for overcoming an immune tolerance of a subject to an antigen-expressing cervical, head and neck, or breast tumor, comprising administering to the subject either: (a) a composition comprising a recombinant polypeptide comprising a PEST-like amino acid sequence derived from a prokaryotic organism, fused to the antigen or a fragment thereof, or (b) a composition comprising a recombinant nucleotide encoding the recombinant polypeptide, whereby the subject mounts an immune response against the antigen-expressing tumor, thereby overcoming an immune tolerance of a subject to an antigen-expressing cervical, head and neck, or breast tumor.

The PEST-like amino acid sequence has, in another embodiment, a sequence selected from SEQ ID NO:2-7. In another embodiment, the PEST-like sequence is any other PEST-like sequence known in the art. Each possibility represents a separate embodiment of the present invention.

In another embodiment, the present invention provides a method of suppressing a formation of a thyroid tumor, comprising administering an effective amount of a vaccine comprising either: (a) a recombinant polypeptide comprising a PEST-like amino acid sequence derived from a prokaryotic organism, fused to the antigen or a fragment thereof, or (b) a recombinant nucleotide encoding the recombinant polypeptide, whereby the subject mounts an immune response against the antigen-expressing tumor, thereby suppressing a formation of a thyroid tumor.

As provided herein, vaccines of the present invention were shown to be efficacious in a mouse model of head and neck cancer on the C57Bl/6 background that expresses the HPV-16 tumor associated antigens, E6 and E7. HPV-16 is, in another embodiment, the primary causative agent of cervical cancer. In another embodiment, HPV-16 is has been strongly associated with certain forms of head and neck cancer. Thus, in another embodiment, methods of the present invention have utility in treating, inhibiting formation of, and suppressing growth of cervical tumors. In another embodiment, methods of the present invention have utility in treating, inhibiting formation of, and suppressing growth of head-and-neck tumors. Each possibility represents a separate embodiment of the present invention.

Her-2, another antigen utilized in the Examples herein, is expressed, in another embodiment, in breast cancer, ovarian cancer, and cancers of the alimentary canal, stomach, and pancreas. Thus, in another embodiment, methods of the present invention have utility in treating, inhibiting formation of, and suppressing growth of breast cancer (in another embodiment, breast carcinoma) tumors, ovarian cancer, and cancers of the alimentary canal, stomach, and pancreas. Each possibility represents a separate embodiment of the present invention.

T cells of high avidity to self antigen are, under the conditions utilized herein, deleted by negative selection during the formation of the T cell repertoire in the thymus. Under the conditions utilized herein, it is probable that E7, as it is expressed in the thymic stromal tissue, results in a loss of the high avidity RAHYNTIVTF specific CD8$^+$ T cells present in the C57Bl/6 wild type mouse. In another embodiment, vaccines of the present invention overcome central tolerance by expanding the low avidity antigen-specific CD8$^+$ T cells that are not negatively selected out during thymopoesis. In another embodiment, these low avidity CD8$^+$ T cells that are elicited are capable of inducing the regression of solid tumors. Each possibility represents a separate embodiment of the present invention.

In another embodiment, fusion proteins of the present invention need not be expressed by LM, but rather can be expressed and isolated from other vectors and cell systems used for protein expression and isolation.

In another embodiment, the present invention provides a recombinant Listeria vaccine strain comprising a fusion protein comprising an ActA protein, or fragment thereof, fused to an antigen. As demonstrated by the data disclosed herein, a recombinant Listeria vaccine strain comprising a fusion protein comprising ActA and an antigen, when administered to an animal, results in the destruction of existing tumors and the induction of antigen specific lymphocytes capable of infiltrating tumors and other diseases where a cellular immune response is beneficial. The present invention also encompasses a method for eliciting an enhanced immune response to an antigen by administering a composition comprising a Listeria vaccine strain comprising, inter alia, an antigen fused to an ActA protein, or fragment thereof. This is because, as demonstrated by the data disclosed herein, administering such a composition to an animal results in, among other things, a clearing of tumors, and the superior induction of lymphocytes specific for tumor antigens when compared to the administration of antigen that is not fused to an ActA protein, or fragment thereof. Further, the present invention comprises a method for enhancing the immunogenicity of an antigen. That is, as demonstrated by the data disclosed herein, fusing an ActA protein, or fragment thereof, to an antigen, results in, among other things, an improved clearance of tumors in animals and an enhanced antigen-specific immune response.

In another embodiment, "homology" refers to identity to an ActA, LLO, PEST-like-, or antigen sequence of greater than 70%. In another embodiment, "homology" refers to identity to a sequence of greater than 72%. In another embodiment, "homology" refers to identity of greater than 75%. In another embodiment, "homology" refers to identity to a sequence of greater than 78%. In another embodiment, "homology" refers to identity of greater than 80%. In another embodiment, "homology" refers to identity of greater than 82%. In another embodiment, "homology" refers to identity to a sequence of greater than 83%. In another embodiment, "homology" refers to identity of greater than 85%. In another embodiment, "homology" refers to identity of greater than 87%. In another embodiment, "homology" refers to identity to a sequence of greater than 88%. In another embodiment, "homology" refers to identity of greater than 90%. In another embodiment, "homology" refers to identity of greater than 92%. In another embodiment, "homology" refers to identity to a sequence of greater than 93%. In another embodiment, "homology" refers to identity of greater than 95%. In another embodiment, "homology" refers to identity to a sequence of greater than 96%. In another embodiment, "homology" refers to identity of greater than 97%. In another embodiment, "homology" refers to identity of greater than 98%. In another embodiment, "homology" refers to identity of greater than 99%. In another embodiment, "homology" refers to identity of 100%. Each possibility represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitoiy RNA (siRNA), micro RNA (mRNA) and ribozymes. The use of siRNA and mRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In one embodiment, "fusion protein" refers to a protein comprising two or more proteins linked together by peptide bonds or other chemical bonds. In another embodiment, the proteins are linked together directly by a peptide or other chemical bond. In another embodiment, the proteins are linked together with one or more amino acids (e.g. a "spacer") between the two or more proteins. Each possibility represents a separate embodiment of the present invention.

In another embodiment, the ActA or LLO fragment is attached to the antigen or fragment thereof by chemical conjugation. In another embodiment, paraformaldehyde is used for the conjugation. In another embodiment, the conjugation is performed using any suitable method known in the art. Each possibility represents another embodiment of the present invention.

In another embodiment, the cancer treated by a method of present invention is a cervical cancer tumor. In another embodiment, the cancer is a head and neck cancer tumor. In another embodiment, the cancer is a breast cancer tumor. In another embodiment, the cancer is an ano-genital cancer tumor.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma. Each possibility represents a separate embodiment of the present invention.

Each of the above types of cancer represents a separate embodiment of the present invention.

Enhanced cell mediated immunity was demonstrated for fusion proteins comprising an antigen and truncated LLO containing the PEST-like amino acid sequence, SEQ ID NO: 1: KENSISSMAPPASPPASPKTPIEKKHADEIDK. The .DELTA.LLO used in some of the Examples was 416 amino acids long, as 88 residues from the amino terminus which is inclusive of the activation domain containing cystine 484 were truncated. In other experiments (e.g. Example 16) a truncated LLO containing 441 AA of LLO was utilized. However, it is believed that other .DELTA.LLOs without the activation domain, and in particular cysteine 484, will also be effective. More particularly, it is believed that fusion of an antigen to any .DELTA.LLO including the PEST-like amino acid sequence, SEQ ID NO: 1, can enhance cell mediated and anti-tumor immunity of the antigen.

As provided herein, fusion of an antigen to a non-hemolytic truncated form of listeriolysin O (LLO) enhanced immunogenicity. Specifically, experiments have been performed demonstrating that an LM vector that expresses and secretes a fusion product of Human Papilloma Virus (HPV) strain 16 E7 and listeriolysin, which comprises the PEST-like amino acid sequence SEQ ID NO: 1, is a more potent cancer immunotherapeutic for HPV immortalized tumors than a strain of LM that secretes the E7 protein alone. Experiments were also performed demonstrating that a recombinant vaccinia virus that carries the gene for the fusion protein LLO-E7 which contains the PEST-like amino acid sequence of SEQ ID NO: 1 is a much more potent cancer immunotherapeutic for HPV immortalized tumors than an isogenic strain of vaccinia that carries the gene for E7 protein alone. In comparison, a short fusion protein Lm-AZ/-E7 comprising the E7 antigen fused to the promoter, signal sequence and the first 7 amino acid residues of LLO was an ineffective anti-tumor immunotherapeutic. This short fusion protein terminates directly before the PEST-like sequence and does not contain it.

In another embodiment, the present invention provides an antigen fused to a truncated ActA protein, truncated LLO protein, or fragment thereof. As demonstrated by the data disclosed herein, an antigen fused to a truncated ActA protein, truncated LLO protein, or fragment thereof, when administered to an animal, results in clearing of existing tumors and the induction of antigen specific $CD8^+$ cells capable of infiltrating infected or tumor cells. Therefore, as demonstrated by the data disclosed herein, ActA has the function or activity of enhancing the immunogenicity of an antigen. Thus the present invention includes a fusion protein comprising an antigen fused to a truncated ActA protein, truncated LLO protein, or fragment thereof. Fusion proteins comprising an antigen may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments are then ligated, in another embodiment, to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is then ligated into a plasmid.

In another embodiment, the truncated ActA protein, truncated LLO protein, or fragment thereof, and the antigen is conjugated by any of a number of means well known to those of skill in the art. In another embodiment, the antigen is conjugated, either directly or through a linker (spacer), to the ActA protein or LLO protein. In another embodiment, wherein both the antigen and the ActA protein or LLO protein are polypeptides the chimeric molecule is recombinantly expressed as a single-chain fusion protein.

In another embodiment, wherein the ActA protein or LLO protein and/or the antigen is relatively short (i.e., less than about 50 amino acids) they are synthesized using standard chemical peptide synthesis techniques. Where both molecules are relatively short, in another embodiment, the chimeric molecule is synthesized as a single contiguous polypeptide. In another embodiment, the ActA protein or LLO protein and the antigen may be synthesized separately and then fused by condensation of the amino terminus of one molecule with the carboxyl terminus of the other molecule thereby forming a peptide bond. In another embodiment, the ActA protein or LLO protein and antigen are each condensed with one end of a peptide spacer molecule, thereby forming a contiguous fusion protein.

In another embodiment, the peptides and proteins of the present invention are readily prepared by standard, well-established solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin coupled peptide can be treated with 20% acetic anhydride in acetonitrile. The N-blocked peptide product can then be cleaved from the resin, deprotected and subsequently isolated.

In another embodiment, to ensure that the peptide obtained from either chemical or biological synthetic techniques is the desired peptide, analysis of the peptide composition is conducted. In another embodiment, amino acid composition analysis is conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

In another embodiment, prior to its use, the peptide is purified to remove contaminants. In this regard, it will be appreciated that the peptide will be purified so as to meet the standards set out by the appropriate regulatory agencies and guidelines. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Solid phase synthesis in which the C-terminal amino acid of the sequence is attached to an insoluble support followed by sequential addition of the remaining amino acids in the sequence is used, in another embodiment, for the chemical synthesis of the polypeptides of this invention. Techniques for solid phase synthesis are described by Barany and Merrifield in Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In another embodiment, the chimeric fusion proteins of the present invention are synthesized using recombinant DNA methodology. Generally this involves creating a DNA sequence that encodes the fusion protein, placing the DNA in an expression cassette, such as the plasmid of the present invention, under the control of a particular promoter/regulatory element, and expressing the protein.

DNA encoding the fusion protein (e.g. truncated ActA/antigen) of the present invention may be prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. Tetra. Lett., 22: 1859-1862); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences may be obtained by the ligation of shorter sequences.

In another embodiment, the present invention provides an isolated nucleic acid encoding a truncated ActA molecule, or a fragment thereof, fused to an antigen, wherein the nucleic acid is at least about 80% homologous, more preferably at least about 90% homologous with a nucleic acid having the sequence of SEQ ID NO:24. Preferably, the nucleic acid is at least about 95% homologous, more preferably at least about 96% homologous with a nucleic acid having the sequence of SEQ ID NO:24, more preferably at least about 97% homologous with a nucleic acid having the sequence of SEQ ID NO:24, more preferably at least about 98% homologous with a nucleic acid having the sequence of SEQ ID NO:24, more preferably at least about 99% homologous with a nucleic acid having the sequence of SEQ ID NO:24, most preferably, about 99.9% homologous to SEQ ID NO:24, disclosed herein. Even more preferably, the nucleic acid is SEQ ID NO:24. The isolated nucleic acid of the invention should be construed to include an RNA or a DNA sequence encoding an ActA protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Such modifications are detailed elsewhere herein. Any and all combinations of modifications of the nucleotide sequences are contemplated in the present invention.

In another embodiment, the present invention provides an isolated nucleic acid encoding a truncated ActA protein and an isolated nucleic acid encoding an antigen operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, expression of a truncated ActA protein and an antigen, either alone or fused to a detectable tag polypeptide in a cell or mammal is accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding a truncated ActA protein and an antigen may be accomplished by placing the nucleic acid encoding a truncated ActA protein and an antigen, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing a truncated ActA protein and an antigen using a vector allows the isolation of large amounts of recombinantly produced protein. It is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides a vector comprising an isolated nucleic acid encoding a truncated ActA protein and an antigen. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the nucleic acids encoding a truncated ActA protein and an antigen may be cloned into a plasmid vector.

Once armed with the present invention, it is readily apparent to one skilled in the art that other nucleic acids encoding an ActA protein filsed to an antigen can be obtained by following the procedures described herein in the experimental details section for the generation of other ActA/antigen fusion proteins as disclosed herein (e.g., site-directed mutagenesis, frame shift mutations, and the like), and procedures that are well-known in the art or to be developed.

Methods for the generation of derivative or variant forms of fusion proteins are well known in the art, and include, inter alia, using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York), and elsewhere herein.

In another embodiment, the present invention provides a nucleic acid encoding an ActA/antigen fusion protein wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding an ActA/antigen fusion protein. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The skilled artisan will recognize that the ActA protein of the present invention need not be that which is set forth exactly in SEQ ID NO:23, but rather that other alterations, modifications, or changes can be made that retain the functional characteristics of an ActA protein fused to an antigen as set forth elsewhere herein.

In another embodiment, peptides of the present invention can incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

In another embodiment, other modifications are incorporated without adversely affecting the activity. In another embodiment, such modifications include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

In another embodiment, acid addition salts peptides of the present invention are utilized as functional equivalents thereof. In another embodiment, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of truncated ActA or LLO, or fragments thereof, proteins or peptides. Analogs can differ from naturally occurring proteins or peptides by conservative amino acid sequence differences or by modifications which do not affect sequence, or by both.

In another embodiment, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

In another embodiment polypeptides are modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another embodiment, the present invention provides an antigen with enhanced immunogenicity. That is, as the data disclosed herein demonstrate, an antigen fused to a truncated ActA protein, truncated LLO protein, or fragment thereof, when administered to an animal, results in a clearance of existing tumors and the induction of antigen specific cytotoxic lymphocytes capable of infiltrating tumor or infected cells. When armed with the present disclosure, and the methods and compositions disclosed herein, the skilled artisan will readily realize that the present invention in amenable to treatment and/or prevention of a multitude of diseases.

In another embodiment, the antigen fused to the truncated ActA protein, truncated LLO protein, or fragment thereof is an antigen derived from a tumor. In another embodiment, the antigen is derived from or an infectious organism.

Figure 2:
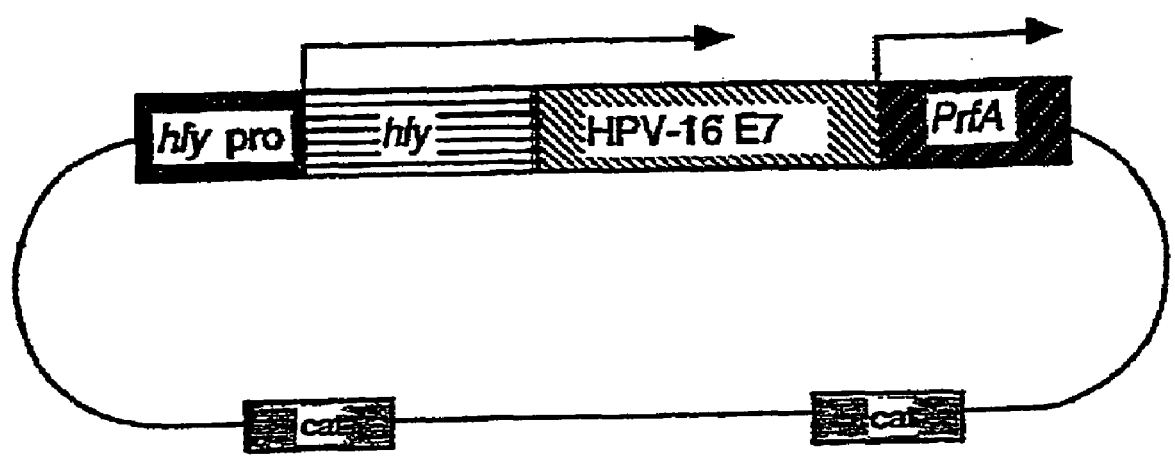
FIG. 2 is a diagram of a multi-copy plasmid containing prfa and E7 fused to a truncated form of the hly gene (.DELTA.hly) that produced .DELTA.LLO.

In a first set of experiments, the HPV-E7 antigen was expressed in E7 as a fusion protein with a truncated form of LLO. A plasmid was constructed as shown in FIG. 2 that was used to complement a prfA(−) mutant of Lm. Bacteria were delivered intra-peritoneally on days 7 and 14 following tumor challenge. Table 1 provides details for optimized anti-tumor effects observed in this model in three different, HPV-16, E7 expressing tumor cell lines, TC-1, C3 and EL-4/E7.

TABLE 1

Survival in animals vaccinated with Lm-LLO-E7.

| Treatment | Number of tumor free animals versus total in study (number survived) | | |
|---|---|---|---|
| | $10^5$ TC-1 on Day 60 | $10^6$ C3 on Day 42 | $5 \times 10^5$ EL-4/E7, Day 40 |
| $10^8$ Lm-LLO-E7 | 3/8 (5) | 4/8 (8) | 4/8 (6) |
| $10^8$ Lm-Gag (ZY-18; irrelevant antigen) | 2/8 (2) | 0/8 (0) | 2/8 (0) |
| Naive | 0/8 (0) | 0/8 (0) | 1/8 (0) |

Animals administered TC-1 or EL-4/E7 tumor cells that were tumor free were re-challenged on day 60 with TC-1 or day 40 EL-4/E7, respectively. The two animals in each group that had been immunized with Lm-Gag grew tumors whereas the animals immunized with Lm-E7 remained tumor free until termination of the experiment (day 124 in the case of TC-1 and day 54 for EL-4/E7).

A second LM vaccine that expresses a E7 fusion protein, referred to as Lm-LLO-E7, was prepared by complementing a prfA-deletion mutant with a plasmid containing a copy of the prfA gene and a copy of the E7 gene fused to a form of the hly gene truncated to eliminate the hemolytic activity of the enzyme, .DELTA.LLO (see FIG. 2). Functional LLO was maintained by the organism via the endogenous chromosomal copy of hly. The expression and secretion of the fusion protein was verified by Western blot.

The ability of the Lm-LLO-E7 and Lm-E7 (e.g. LM expressing E7, without the LLO fragment) vaccines to induce anti-tumor immunity was then compared in a regression model. As shown in Table 2, Lm-LLO-E7 was found to be more effective than Lm-E7. This difference in efficacy is believed to be due to the presence of the PEST-like sequence, SEQ ID NO:1, in Lm-LLO-E7.

TABLE 2

Number of mice cured of TC-1 tumor at conclusion of experiment. An additional experiment.

| Treatment | Mice TC-1 free at Day 45 | Mice alive at day 45 | Mice alive at day 134 |
|---|---|---|---|
| Naive | 0/8 | 0/8 | 0/8 |
| Lm-LL0-E7 | 4/8 | 8/8 | 4/8 |
| Lm-E7 | 0/8 | 7/8 | 0/8 |

Thus, expression of the foreign gene as a fusion protein with .DELTA.LLO enhances the immunogenicity of the antigen.

Figure 3:
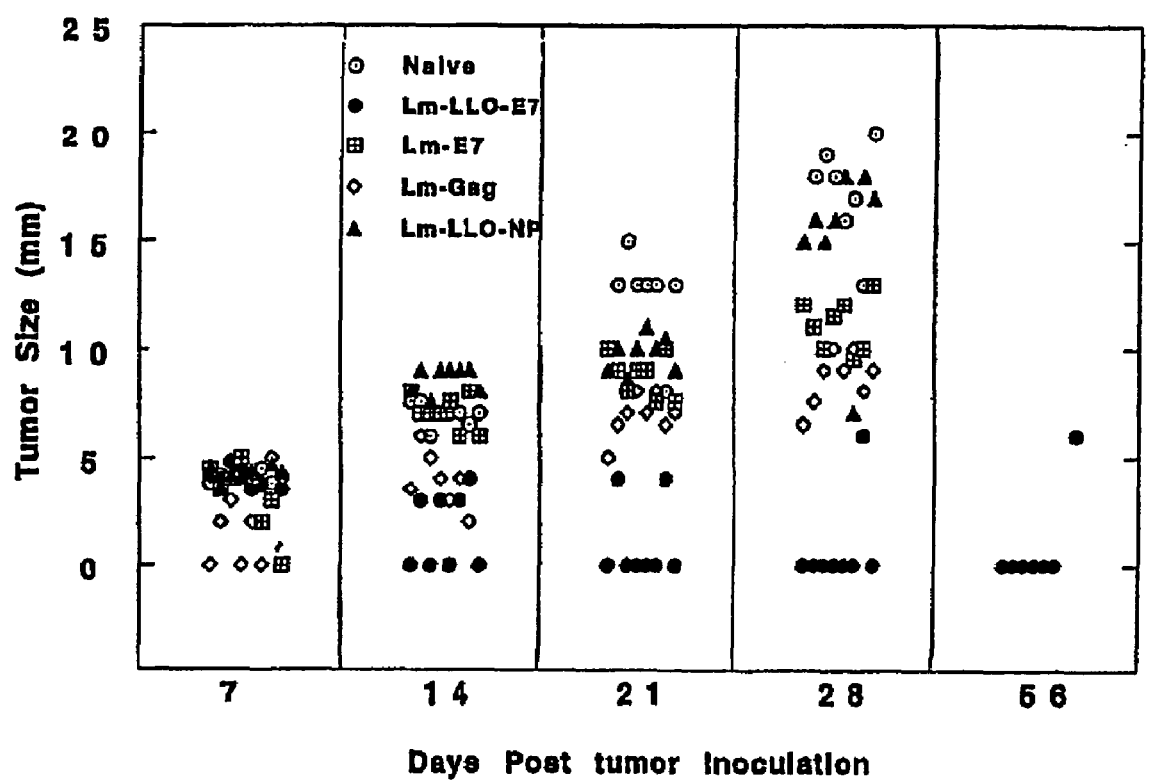
FIG. 3 is a graph showing tumor immunotherapeutic efficacy of E7 antigen expressed in LM. Tumor size in millimeters in mice is shown at 7, 14, 21, 28 and 56 days post tumor-inoculation. Naive mice are depicted by an open-circle; mice administered Lm-LLO-E7 are depicted by a filled circle; mice administered Lm-E7 are depicted by a square; mice administered Lm-Gag are depicted by an open diamond; and mice administered Lm-LLO-NP are depicted by a filled triangle.
Figure 4:
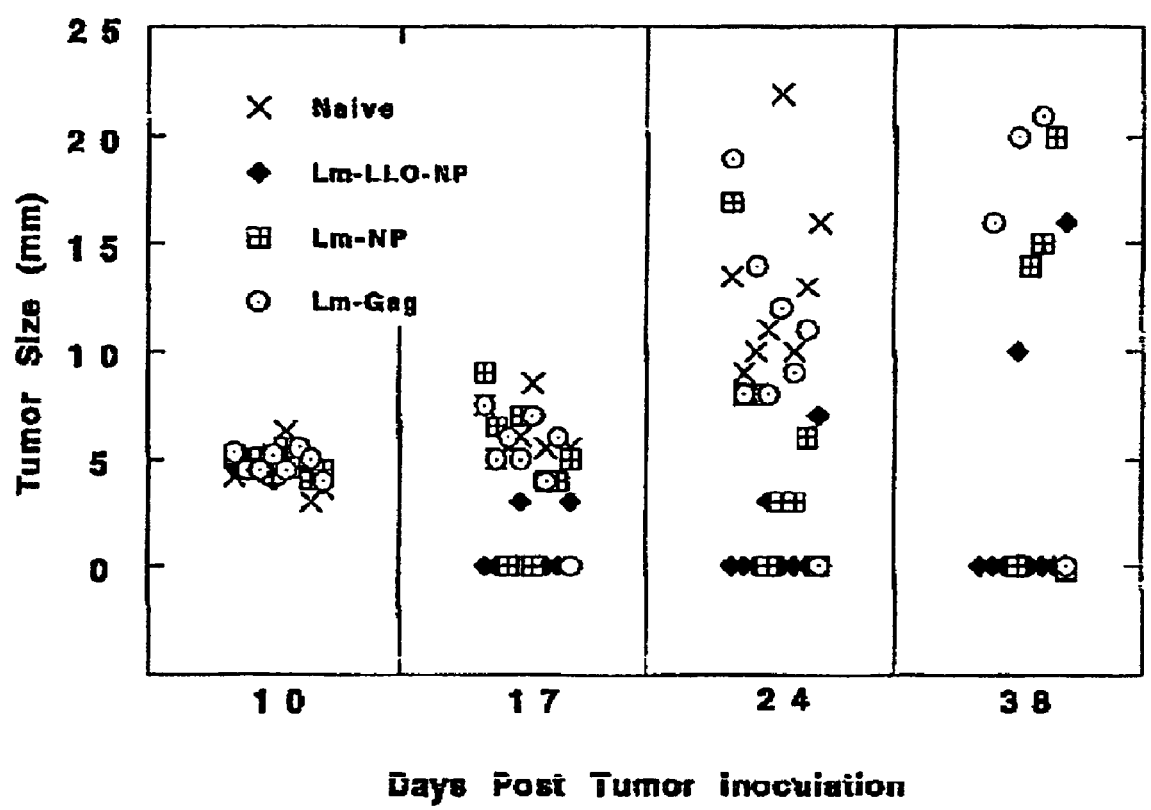
FIG. 4 is a graph showing tumor immunotherapeutic efficacy of NP antigen expressed in LM. Tumor size in millimeters in mice is shown at 10, 17, 24, and 38 days post tumor-inoculation. Naive mice are depicted by an X; mice administered Lm-LLO-NP are depicted by a filled diamond; mice administered Lm-NP are depicted by a square; and mice administered Lm-Gag are depicted by an open circle.

Additional experiments were performed to compare the ability of Lm-E7 with Lm-LLO-E7 to induce the regression of established subcutaneous HPV-16 immortalized tumors from C57Bl/6 mice. Results from these experiments are depicted in FIG. 3. In these experiments, mice were immunized i.p. with 0.1 $LD_{50}$ with one of four constructs, Lm-E7, Lm-Gag (isogenic with Lm-E7 except for the antigen expressed), Lm-LLO-E7 or Lm-LLO-NP. Lm-LLO-NP is isogenic with Lm-LLO-E7 but expresses influenza antigen. A second immunization was performed on day 14. As can be seen in FIG. 3, 6 of 8 mice immunized with Lm-LLO-E7 were cured of their tumors and remained tumor free. None of the other animals demonstrated any regression of the established tumors. Similar results have been achieved for Lm-LLO-E7 under different immunization protocols. Further, just one immunization has been demonstrated to cure mice of established TC-1 of 5 mm diameter. In order to confirm the generality of the finding that fusing LLO to an antigen confers enhanced immunity, a version of Lm-NP similar to Lm-E7 was constructed. This recombinant was prepared as depicted in FIG. 1 except that influenza nucleoprotein replaced E7 as the antigen. The ability of the new Lm-NP was compared with Lm-LLO-NP (described in U.S. Pat. No. 5,830,702 and prepared as depicted in FIG. 2). Results from these experiments are depicted in FIG. 4. In these experiments, 32 BALB/c mice were inoculated with $5 \times 10^5$ RENCA-NP tumor cells. RENCA-NP is a renal cell carcinoma retrovirally transduced with influenza nucleoprotein NP (described in U.S. Pat. No. 5,830,702). After palpable macroscopic tumors had grown on day 10, eight animals in each group were immunized i.p. with 0.1 $LD_{50}$ with one of three constructs, Lm-NP, Lm-Gag (isogenic with Lm-NP except for the antigen expressed) and Lm-LLO-NP. The animals received a second immunization one week later. Eight animals were left untreated. At the end of the experiment on day 40, all the mice in the naive group had large tumors or had died. Only one mouse in the group that received Lm-Gag and two mice in the group that received Lm-NP were tumor free. This experiment demonstrates that fusing an antigen to LLO is not restricted to E7 and that the form of the antigen is not important.

Additional experiments were performed to confirm the enhanced therapeutic efficacy of a fusion protein comprising the E7 antigen and a truncated form of LLO. In these experiments, a vaccinia vector that expresses E7 as a fusion protein with a non-hemolytic truncated form of LLO was constructed. The WR strain of vaccinia was used as the recipient and the fusion gene was excised from the listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition, SC11 allows the selection of recombinant viral plaques to TK selection and beta-galactosidase screening.

Figure 5:
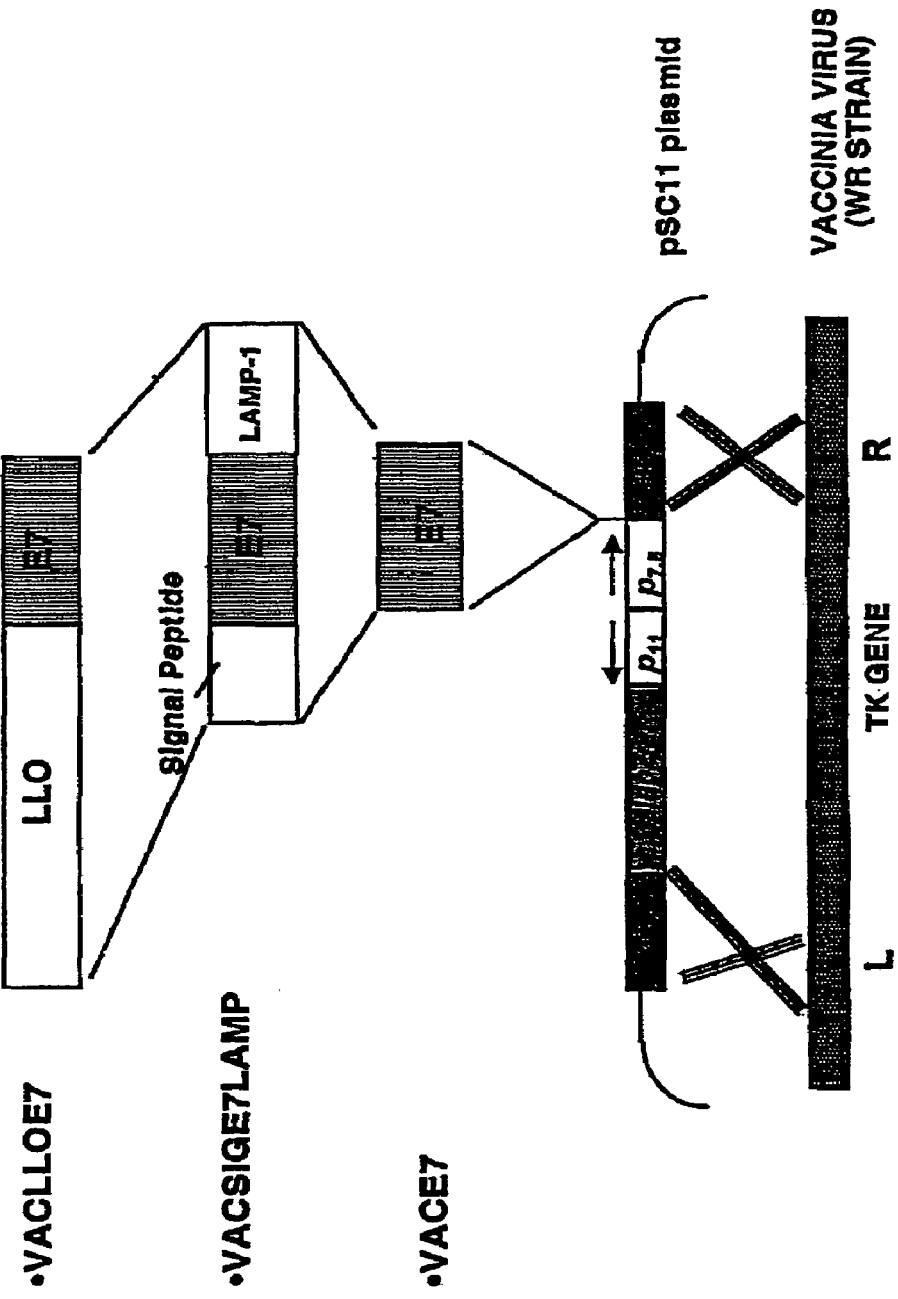
FIG. 5 is a diagram of various Vaccinia virus constructs expressing different forms of HPV16 E7 protein.

FIG. 5 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1 (Lin et al. Proc. Natl. Acad. Sci. USA 1995 92:11671-5; Wu et al. Cancer Res. 1996 56:21-6). It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC1 1-E7 construct was used to transfect the TK-ve cell line CV1 that had been infected with the wildtype vaccinia strain, WR. Cell lysates obtained from this co-infection/transfection step contain vaccinia recombinants that were plaque purified 3 times. Expression of the LLO-E7 fusion product by plaque purified vaccinia was verified by Western blot using an antibody directed against the LLO protein sequence. In addition, the ability of Vac-LLO-E7 to produce $CD8^+$ T cells specific to LLO and E7 was determined using the LLO (91-99) and E7 (49-57) epitopes of Balb/c and C57/BL6 mice, respectively. Results were confirmed in a chromium release assay.

Figure 6:
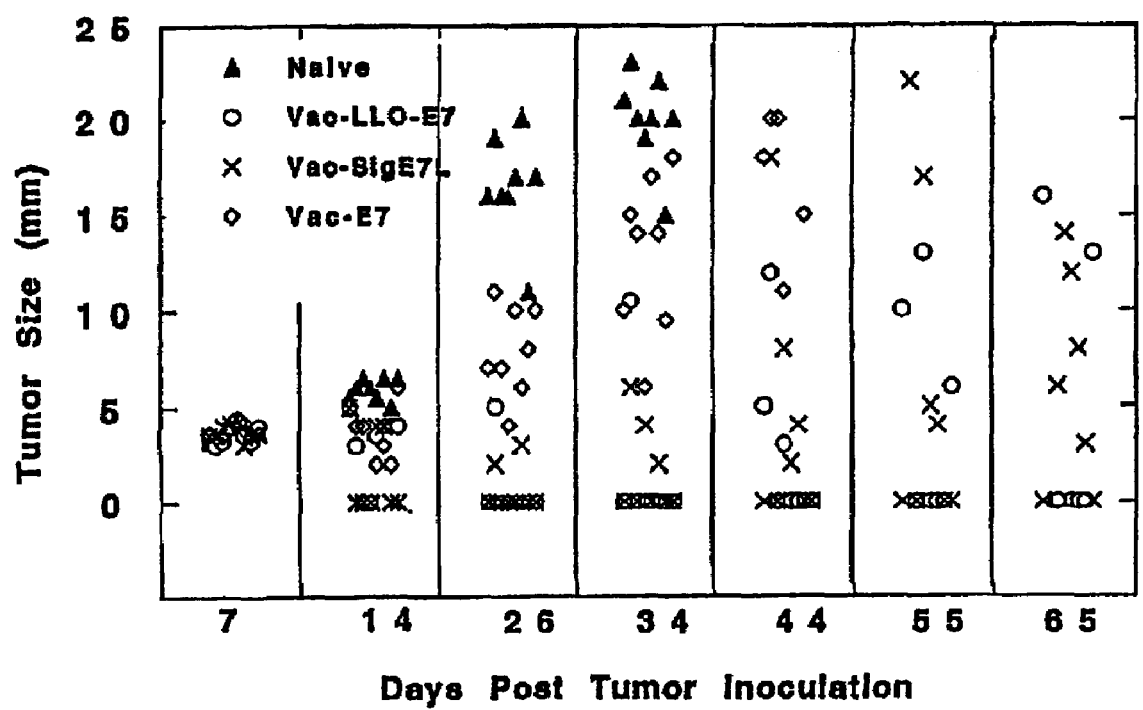
FIG. 6 is a graph showing tumor immunotherapeutic efficacy of antigens expressed by Vaccinia. Tumor size in millimeters in mice is shown at 7, 14, 26, 34, 44, 55 and 65 days post tumor-inoculation. Naive mice are depicted by a filled triangle; mice administered Vac-LLO-E7 are depicted by an open circle; mice administered Vac-SigE7L are depicted by an X; and mice administered Vac-E7 are depicted by an open diamond.

Tumor rejection studies were performed with TC-1 following the same protocol as described herein. Two experiments were performed with differing delays before treatment was started. In one experiment, treatments were initiated when the tumors were about 3 mm in diameter (see FIG. 6). As of day 76, 50% of the Vac-LLO-E7 treated mice are tumor free and 25% of the Vac-SigE7Lamp mice were tumor free.

In a second experiment, TC-1 tumors were grown to a larger size (5 to 6 mm). The LLO-E7 fusion protein based vectors were then compared against various Vaccinia virus constructs. Although some of the vaccine groups showed significant temporary regression of TC-1, by day 65 the data demonstrates that Lm-LLO-E7 and Vac-LLO-E7 were the most effective vaccines with respect to the ability to permanently induce the regression of established TC-1. Only 12% of the Vac-SigE7Lamp treated mice were tumor free while 37% of the Vac-LLO-E7 and Lm-LLO-E7 mice were tumor free. All other mice were dead.

Thus, expression of the antigen as a fusion protein with a non-hemolytic truncated form of LLO or ActA in host cell systems in *Listeria* and host cell systems other than *Listeria* results in enhanced immunogenicity of the antigen. While comparative experiments were performed with vaccinia, a multitude of other plasmids and expression systems which can be used to express these fusion proteins are known. For example, bacterial vectors useful in the present invention include, but are not limited to *Salmionella* sp., *Shigella* sp., BCG, *L. monocytogenes* and *S. gordonii*. In addition the fusion proteins can be delivered by recombinant bacterial vectors modified to escape phagolysosomal fusion and live in the cytoplasm of the cell. Viral vectors useful in the present invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. Naked DNA vectors can also be used.

In another embodiment, a commercially available plasmid is used in the present invention. Such plasmids are available from a variety of sources, for example, Invitrogen (La Jolla, Calif.), Stratagene (La Jolla, CA.), Clontech (Palo Alto, CA.), or can be constructed using methods well known in the art. A commercially available plasmid such as pCR2.1 (Invitrogen, La Jolla, CA.), which is a prokaryotic expression vector with an prokaryotic origin of replication and promoter/regulatory elements to facilitate expression in a prokaryotic organism.

The present invention further comprises transforming such a *Listeria* strain with a plasmid comprising, an isolated nucleic acid encoding a truncated ActA protein, truncated LLO protein, or fragment thereof, and an antigen. As a non-limiting example, if an LM vaccine strain comprises a deletion in the prfA gene or the actA gene, the plasmid can comprise a prfA or actA gene in order to complement the mutation, thereby restoring function to the *L. monocytogenes* vaccine strain. As described elsewhere herein, methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.).

The plasmid of the present invention comprises a promoter/regulatory sequence operably linked to a gene encoding a fusion protein, antigen, amino acid metabolism gene, or combinations thereof.

Plasmids and other expression vectors useful in the present invention are described elsewhere herein, and can include such features as a promoter/regulatory sequence, an origin of replication for gram negative and/or gram positive bacteria, and an isolated nucleic acid encoding a fusion protein. Further, the isolated nucleic acid encoding a fusion protein will have its own promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of bacteriophage lambda ($P_L$ and $P_R$), the trp, recA, lacZ, lacd, and gal promoters of E. coli, the alpha-amylase (Ulmanen et al, 1985. J. Bacteriol. 162:176-182) and the S28-specific promoters of B. subtilis (Gilman et al, 1984 Gene 32:11-20), the promoters of the bacteriophages of Bacillus (Gryczan, 1982, In: The Molecular Biology of the Bacilli, Academic Press, Inc., New York), and Streptomyces promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter (GenBank Acc. No. Y07639), the Listerial hly promoter (GenBank Acc. No. X15127), and the Listerial p60 promoter (GenBank Acc. No. AY126342), or fragments thereof.

Proper expression in a prokaryotic cell utilizes, in another embodiment, a ribosome binding site upstream of the gene-encoding sequence. Such ribosome binding sites are disclosed, for example, by Gold, L., et al (1981, Ann. Rev. Microbiol. 35:365-404).

In another embodiment, the present invention provides methods for enhancing the immunogenicity of a self antigen via fusion of the antigen to a non-hemolytic truncated form of listeriolysin O or .DELTA.LLO. In one embodiment, the antigen is fused to the PEST-like amino acid sequence, SEQ ID NO:1, of LLO. The present invention further provides methods and compositions for enhancing the immunogenicity of a self antigen by fusing the antigen to a truncated ActA protein, truncated LLO protein, or fragment thereof. As demonstrated by the data disclosed herein, an antigen fused to an ActA protein, when administered to an animal elicts an immune response that clears existing tumors and results in the induction of antigen specific cytotoxic lymphocytes.

The present invention also provides methods for enhancing cell mediated and anti-tumor immunity and compositions with enhanced immunogenicity which comprise a PEST-like amino acid sequence derived from a prokaryotic organism fused to or embedded within an antigen. The PEST-like sequence can be fused to either the amino terminus or the carboxy terminus of the antigen. As demonstrated herein, fusion of an antigen to the PEST-like sequence of LM enhanced cell mediated and anti-tumor immunity of the antigen. It is believed that fusion of an antigen to other PEST-like sequences derived from other prokaryotic organisms will also enhance immunogenicity of the antigen. PEST-like sequence of other prokaryotic organism can be identified routinely in accordance with methods such as described by, for example Rechsteiner and Rogers (1996, Trends Biochem. Sci. 21:267-271) for LM. Alternatively, PEST-like amino acid sequences from other prokaryotic organisms can also be identified based by this method. Other prokaryotic organisms wherein PEST-like amino acid sequences would be expected to include, but are not limited to, other Listeria species. For example, the LM protein ActA contains four such sequences. These are KTEEQPSEVNTGPR (SEQ ID NO:2), KASVTDTSEGDLDSSMQSADEST PQPLK (SEQ ID NO:3), KNEEVNASDFPPPPTDEELR (SEQ ID NO:4), and RGGIPTSEEFSSLNSGDFTDDENSETTEEEIDR (SEQ ID NO:5). Also Streptolysin O from Streptococcus sp. contain a PEST-LIKE sequence. For example, Streptococcus pyogenes Streptolysin O comprises the PEST-like sequence KQNTASTETTTTEQPK (SEQ ID NO:6) at amino acids 35-51 and Streptococcus equisimilis Streptolysin O comprises the PEST-like sequence KQNTANTETTTTNEQPK (SEQ ID NO:7) at amino acids 38-54. Further, the PEST-like sequence can be embedded within the antigenic protein. Thus, for purposes of the present invention, by "fusion" it is meant that the antigenic protein comprises both the antigen and the PEST-like amino acid sequence either linked at one end of the antigen or embedded within the antigen.

In another embodiment, fusion proteins of the present invention are produced recombinantly via a plasmid which encodes either a truncated form of the LLO comprising the PEST-like amino acid sequence of L. monocytogenes or a PEST-like amino acid sequence derived from another prokaryotic organism and the antigen. However, the antigen may also be chemically conjugated to the truncated form of listeriolysin O comprising the PEST-like amino acid sequence of L. monocytogenes or a PEST-like amino acid sequence derived from another prokaryotic organism. For purposes of the present invention, by "antigen" it is meant to include the native antigen gene or gene product or truncated versions of these that include identified T cell epitopes. These fusion proteins can then be incorporated into vaccines for administration to animals, preferably humans, to invoke an enhanced immune response against the antigen of the fusion protein. In one embodiment, the fusion proteins of the present invention are delivered as DNA vaccines, RNA vaccines or replicating RNA vaccines. As will be obvious to those of skill in the art upon this disclosure, vaccines comprising the fusion proteins of the present invention are particularly useful in the prevention and treatment of infectious and neoplastic diseases.

In another embodiment, a vaccine of the present invention further comprises an adjuvant. Examples of adjuvants useful in these vaccines include, but are not limited to, unmethylated CpG, quill glycosides, CFA, QS21, monophosphoryl lipid A, liposomes, and bacterial mitogens and toxins.

The present invention further comprises administering to an animal or human an effective amount of a composition comprising a vaccine of the present invention. The construction of such strains is detailed elsewhere herein. The composition comprises, among other things, a pharmaceutically acceptable carrier. In another embodiment, the composition includes a Listeria vaccine strain comprising a truncated ActA protein, truncated LLO protein, or fragment thereof, fused to an antigen, and a pharmaceutically acceptable carrier.

In another embodiment, the present invention provides various kits which comprise a compound, including a Listeria vaccine strain comprising an antigen fused to a truncated LLO protein, truncated ActA protein, or a fragment thereof, an antigen fused to a truncated ActA protein or truncated LLO protein, or a fragment thereof, an applicator, and an instructional material which describes use of the compound to perform the methods of the invention. Although model kits are described below, the contents of other useful kits will be apparent to the skilled artisan in light of the present disclosure. Each of these kits is contemplated within the present invention.

In another embodiment, the present invention provides a kit for eliciting an enhanced immune response to an antigen, the kit comprising an antigen fused to a truncated ActA protein, truncated LLO protein, or fragment thereof, and a pharmaceutically acceptable carrier, said kit further comprising an applicator, and an instructional material for use thereof.

In another embodiment, the present invention provides a kit for eliciting an enhanced immune response to an antigen. The kit is used in the same manner as the methods disclosed herein for the present invention. Briefly, the kit may be used to administer a *Listeria* vaccine strain comprising an antigen fused to a truncated ActA protein or LLO protein. Additionally, the kit comprises an applicator and an instructional material for the use of the kit. These instructions simply embody the examples provided herein.

In another aspect, the invention includes a kit for eliciting an enhanced immune response to an antigen. The kit is used in the same manner as the methods disclosed herein for the present invention. Briefly, the kit may be used to administer an antigen fused to a truncated ActA protein or truncated LLO protein. Additionally, the kit comprises an applicator and an instructional material for the use of the kit. These instructions simply embody the examples provided herein.

EXPERIMENTAL EXAMPLES

Example 1

Tumor Cell Lines

TC-1 is a lung epithelial cell from C57BL/6 mice immortalized by HPV-16 E6 and E7 and transformed by pVEJB expressing activated human c-HA-ras. C3 is a mouse embryo cell frp, C57BL/6 mice immortalized with the complete genome of HPV 16 and transformed with pEJ-ras. EL-4/E7 is the thymoma EL-4 retrovirally transduced with E7.

Example 2

Comparison of Efficacy of Lm-GG/E7, Lm-AZ/E7 and Vac-SigE7Lamp

TC-1 ($1 \times 10^5$) or C-3 ($5 \times 10^5$) tumor cells were implanted subcutaneously in mice and allowed to grow for 7 to 9 days by which time they were palpable (about 5 mm in size). Mice were then immunized i.p. with one of three constructs, Vac-SigE7Lamp ($10^7$ PFU), Lm-E7 ($10^6$ CFU) or Lm-LLO-E7 ($10^7$ CFU). Animals received Lm-LLO-E7 and LM-E7 on days 7 and 14. Surviving mice were re-challenged with $10^5$ TC-1 on day 43.

Example 3

Comparison of Efficacy of Vac-LLO-E7, Vac-E7 and Vac-SigE7Lamp

Four groups of 8 mice were implanted with $10^5$ cells of TC-1. After 7 days the tumors were approximately 4 mm in size. One group of mice was untreated. Each of the other groups received $10^7$ PFU of either Vac-E7, Vac-LLO-E7 or Vac-Sig-E7-lamp 7. A booster dose was administered on day 14.

Example 4

Comparison of Efficacy of Vac-LLO-E7 and Lm-LLO-E7 with Various Other Vectors

TC-1 tumor cells ($2 \times 10^5$) were implanted s.c. on the left flank in 96 C57BL/6 mice and allowed to grow for 7 days. The mice were divided into groups of 8 mice and each group was treated with one of the following vaccine: naive (no vaccine); Vac SigE7Lamp, $10^7$ PFU, i.p.; Vac-LLO-E7, $10^7$ PFU, i.p.; or Lm-LLO-E7, $10^7$ PFU, i.p. The animals received a booster immunization one week later. Tumor growth was followed every two days by caliper measurement and recorded as the average of the narrowest and longest surface length. Immune parameters were also determined.

Example 5

Construction of Lm-LLOPEST-E7

The LLO-PEST-E7 fragment can be constructed via SOEing PCR. In Step 1 of this method, PCR reaction 1 uses primer pair GG-36/GG-78 or GG-77/AZ-9 with pGG-55 for the template. PCR reaction 2 uses LLO-PEST and E7 products from the first reaction as templates and the primers GG-36 and AZ-9.

```
GG-36:  5'-GCTAGCCCTCCTTTGATTAGTATATT  (SEQ ID NO:8)
        C-3',

GG-77:  5'-GCGGATGAAATCGATAAGCATGGAGA  (SEQ ID NO:9)
        TACACCTACA-3',

GG-78:  3'-CGCCTACTTTAGCTATTCGTACCTCT  (SEQ ID NO:10)
        ATGTGGATGT-5'

AZ-9:   3'-GAGTCTTTGGTATTGGGCCC-5'.    (SEQ ID NO:11)
```

In step 2, the final SOEing PCR product of 0.7 Kb is ligated into the TA vector pCR2.1.

In step 3, the LLO-PEST-E7 is digested from the plasmid with the enzyme NheI for 2 hours followed by ethanol precipitation and the enzyme XmaI overnight. The prfA fragment from pGG-49 is digested with the enzyme SalI for 2 hours followed by ethanol precipitation and XmaI overnight. pDP-2028 is digested with SalI and XbaI for 2 hours followed by ethanol precipitation and resuspension in Tris:EDTA (TE). The fragment can be stored overnight at 4.degree. C.

In step 4, the 0.7 Kb LLO-PEST-E7, 1.0 Kb prfA and the 9.7 Kb plasmid are ligated. This plasmid is then used to transform XFL-7. Secretion of a 15 Kb fragment can be verified via Western blot. Efficacy is verified against TC-1 tumors.

In other experiments, a chromosomal integrant is generated by amplifying the LLO-PEST-E7 fragment using the primer AZ-B (5'-GCTCTAGATTATGGTTTCT GAG-3'; SEQ ID NO:12) to install a 3' XbaI site and primer ZY-3 (5'-GGGGTACCCT CCTTTGATTAGTATAT-3'; SEQ ID NO:13) to install a 5' KpnI site. pZY-37 and the LLO-PEST-E7 fragment are digested with KpnI and XbaI separately or in NEB buffer 2+BSA overnight. The fragment is ligated into pZY-37 and the following protocol for chromosomal integration is followed. Secretion and efficacy are verified as described above.

Example 6

Construction of Lm-actA-E7

LM strain XFL7 (a prfA negative *L. monocytogenes* 10403s provided by Dr. Jeff Miller, University of California Los Angeles, Los Angeles, CA.) was the organism used in the cloning studies of the construct Lm-actA-E7. Lm-actA-E7 is a recombinant strain of LM, comprising a plasmid that express the E7 protein fused to a truncated version of the actA protein.

Figure 7:
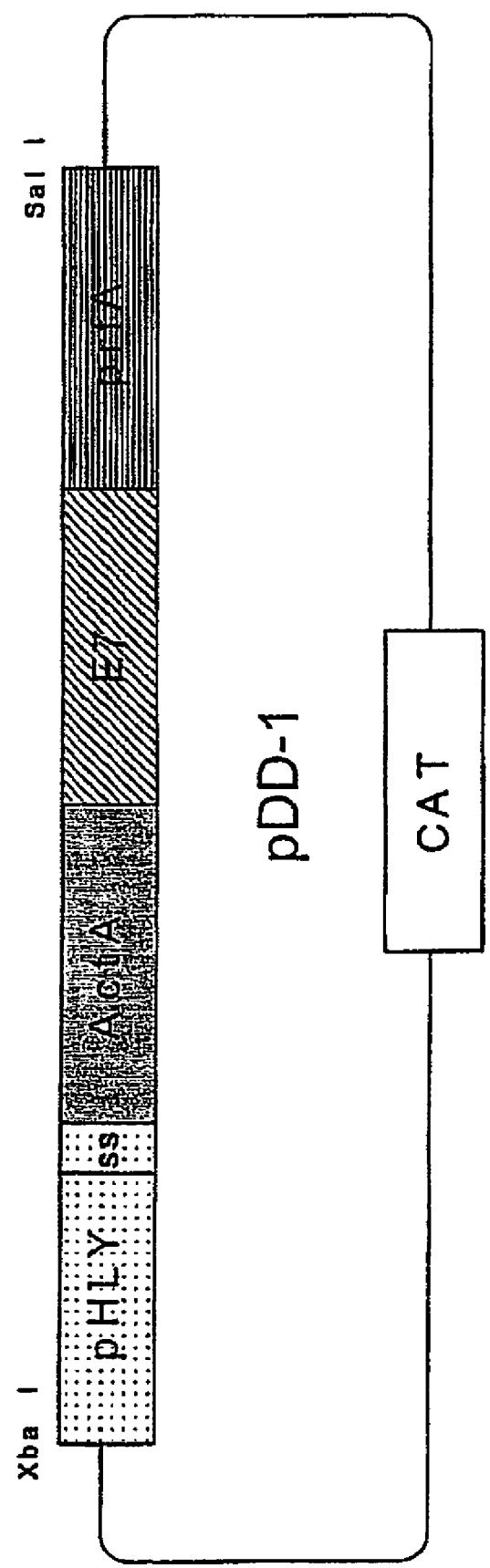
FIG. 7 depicts a schematic representation of the pActA-E7 expression system used to express and secrete E7 from recombinant Listeria bacteria The hly promoter (pHLY) drives expression, the prfA gene is used to select retention of the plasmid by recombinant Listeria in vivo.

Lm-actA-E7 was generated by introducing a plasmid vector pDD-1 constructed by modifying pDP-2028 (Ikonomidis et al., 1994, J. Exp. Med. 180:2209-2218) into LM. The pDD-1 plasmid comprises an expression cassette expressing a copy of the 310 bp hly promoter and the hly signal sequence (ss), (this gene drives the expression and secretion of the actA-E7 gene product), 1170 bp of the actA gene that comprises four PEST sequences (SEQ ID NO:24) (the truncated ActA polypeptide consists of the first 390 amino acids of the molecule, SEQ ID NO:23), a copy of the 300 bp E7 gene (HPV tumor protein), a copy of the 1019 bp prfA gene (controls expression of the virulence genes) and a copy of the CAT gene (chloramphenicol resistance gene) for selection of transformed bacteria clones. (FIG. 7) (Sewell et al. (2004, Arch. Otolaryngol. Head Neck Surg., 130: 92-97).

The hly promoter (pHly) and gene fragment were PCR amplified from pGG55 (pLLO-E7, Gunn et al., 2001, J. Immunol. 167:6471-6479) using primer 5'-GGGGTCTA-GACCTCCTTTGATTAGTATATTC-3' (Xba I site is underlined) (SEQ ID NO:14) and primer 5'-ATCTTCGCTATCT-GTCGCCGCGGCGCGTGCTTCAGTTGTTGCGC-'3 (Not I site is underlined. The first 18 nucleotides are the ActA gene overlap) (SEQ ID NO: 15). The actA gene was PCR amplified from the *Listeria monocytogenes* 10403s wildtype genome using primer 5'-GCGCAACAAA CTGAAGCAGCGGC-CGCGGCGACAGATAGCGAAGAT-3' (SEQ ID NO:16) and primer 5'-TGTAGGTGTATCTCCATGCTC-GAGAGCTAGGCGATCAATTTC-3' (SEQ ID NO:17). The E7 gene was PCR amplified from pGG55 (pLLO-E7) using primer 5'-GGAATTGATCGCCTAGCTCTCGAGCATG-GAGATACACCTACA-3' (SEQ ID NO:18) and primer 5'-AAACGGATTTATTTAGATCCCGGGTTATG GTTTCTGAGAACA-3' (SEQ ID NO:19). The prfA gene was PCR amplified from the *Listeria monocytogenes* 10403s wildtype genome using primer 5'-TGTTCTCA GAAAC-CATAACCCGGGATCTAAATAAATCCGT-TT-3' (SEQ ID NO:20) and primer 5'-GGGGGTCGACCAGCTCTTCTTG-GTGAAG-3' (SEQ ID NO:21). The hly promoter was fused to the actA gene (pHly-actA) was PCR generated and amplified from purified pHly DNA and purified actA DNA using the pHly primer (upstream) 5'-GGGGTCTAGACCTC-CTTTGATTAGTATATTC-3' (SEQ ID NO:14) and acta primer (downstream) 5'-TGTAGGTGTATCTCCATGCTC-GAGAG-CTAGGCGATCAATTTC-3' (SEQ ID NO: 17).

The E7 gene fused to the prfA gene (E7-prfA) was PCR generated and amplified from purified E7 DNA and purified prfA DNA using the E7 primer (upstream) GGAAT-TGATCGCCTAGCTCTCGAGCATG-GAGATACACCTACA-3' (SEQ ID NO: 18) and prfA gene primer (downstream) 5'-GGGGGTCGACCAGCTCT-TCTTG GTGAAG-3' (SEQ ID NO:21).

The pHly-actA fusion product fused to the E7-prfA fusion product is PCR generated and amplified from purified fused pHly-actA DNA product and purified fused E7-prfA DNA product using the pHly primer (upstream) 5'-GGGGTCTA-GACCTCCTT TGATTAGTATATTC-3' (SEQ ID NO:14) and prfA gene primer (downstream) 5'-GGGGGTCGAC-CAGCTCTTCTTGGTGAAG-3' (SEQ ID NO:21) and ligated into pCRII (Invitrogen, La Jolla, Calif.). Competent *E. coli* (TOP10'F, Invitrogen, La Jolla, CA.) were transformed with pCRII-ActAE7. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the pHly primer (upstream) 5'-GGGGTCTAGACCTCCTTTGATTAGTATATTC-3' (SEQ ID NO:14) and the prfA gene primer (downstream) 5'-GGGGGTCGACCAGC TCTTCTTGGTGAAG-3' (SEQ ID NO:21).

The pHly-ActA-E7-PrfA DNA insert was excised from pCRII by double digestion with Xba I and Sal I and ligated into pDP-2028 also digested with Xba I and Sal I. After transforming TOP10'F competent *E. coli* (Invitrogen, La Jolla, CA.) with expression system pActAE7, chloramphenicol resistant clones were screened by PCR analysis using the pHly primer (upstream) 5'-GGGGTCTAGACCTC-CTTTGATT AGTATATTC-3' (SEQ ID NO:14) and the prfa gene primer (downstream) 5'-GGGGGTCGACCAGCTCT-TCTTGGTG-AAG-3' (SEQ ID NO:21). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a midiprep DNA purification system kit (Promega, Madison, Wis.). A prfA-negative strain of penicillin-treated *Listeria* (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37.degree. C. Bacteria were frozen in aliquots at −80.degree. C.

Example 7

Immunoblot Verification of Antigen Expression

Figure 8:
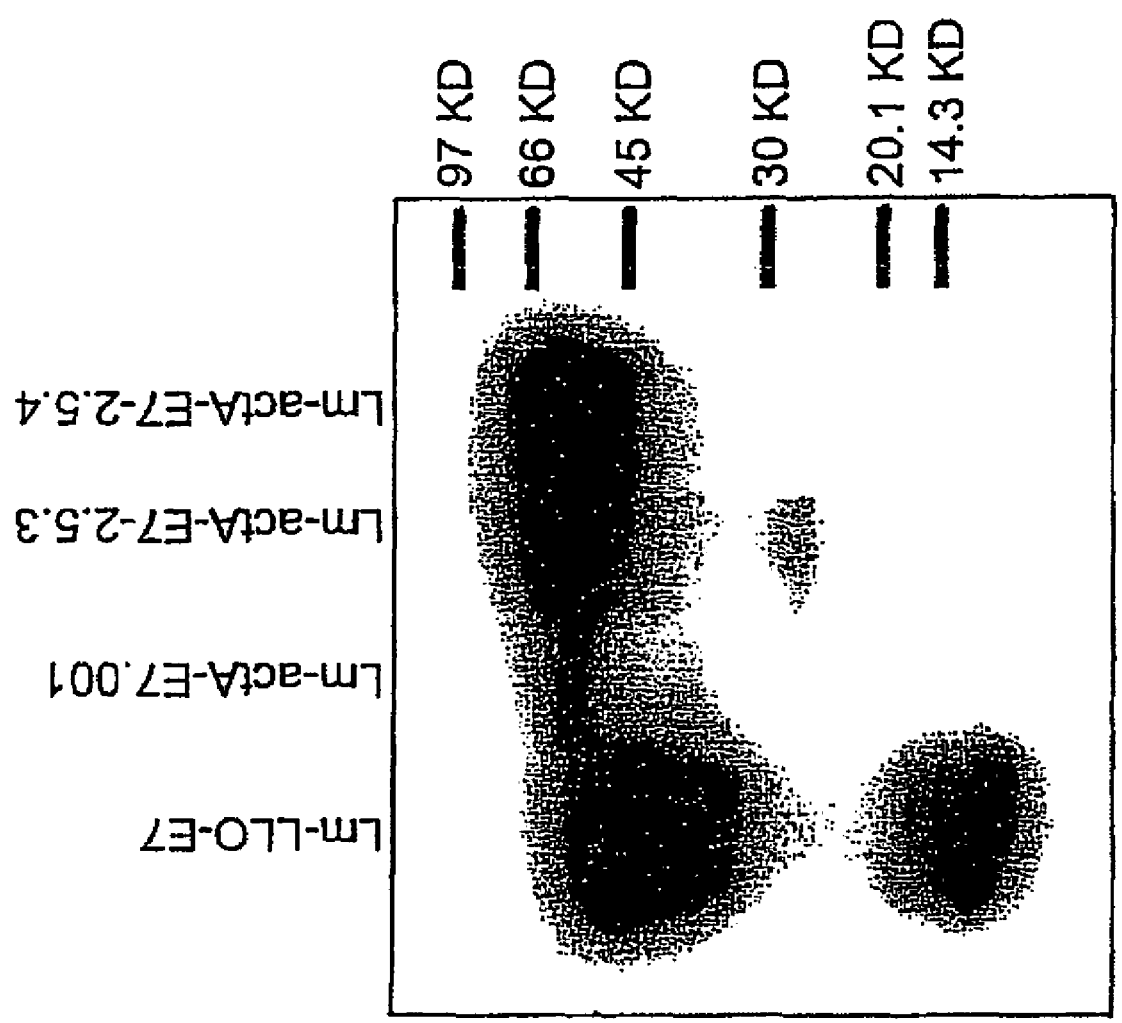
FIG. 8 depicts a Western blot demonstrating that Lm-ActA-E7 secretes E7. Lane 1 depicts Lm-LLO-E7, lane 2 depicts Lm-ActA-E7.001, lane 3 depicts Lm-ActA-E7-2.5.3, lane 4 depicts Lm-ActA-E7-2.5.4.

In order to verify that Lm-ActA-E7 secretes a fusion protein of the correct molecular weight (about 64 kD), recombinant bacteria were grown overnight at 37.degree. C in Luria-Bertoni broth and pelleted. About 18 milliliters of supernatant from each culture was TCA precipitated and E7 expression was analyzed by Western blot. Specifically, clones 0.001, 2.5.3, and 2.5.4 were grown in Luria-Bertoni medium (Difco, Detroit, Mich.) at 37.degree. C. Supernatants were TCA precipitated and resuspended in 1× sample buffer with 0.1N NaOH. Identical amounts of each TCA precipitated supernatant were loaded on 4-20% Tris-glycine SDS-PAGE gel (NOVEX, San Diego, Calif.). The gel was transferred to polyvinylidene difluoride membrane and probed with anti-E7 mAb at a dilution of 1:2500 (Zymed Laboratories, South San Francisco, Calif.). The secondary Ab was HRP-conjugated anti-mouse IgG, diluted 1:5000 (Amersham Pharmacia Biotech, Little Chalfont, U.K.). Blots were developed with Amersham ECL detection reagents and exposed to Hyperfilm (Amersham Pharmacia Biotech) (FIG. 8).

Example 8

Anti-Tumor Immunity of Lm-ActA-E7

Figure 9:
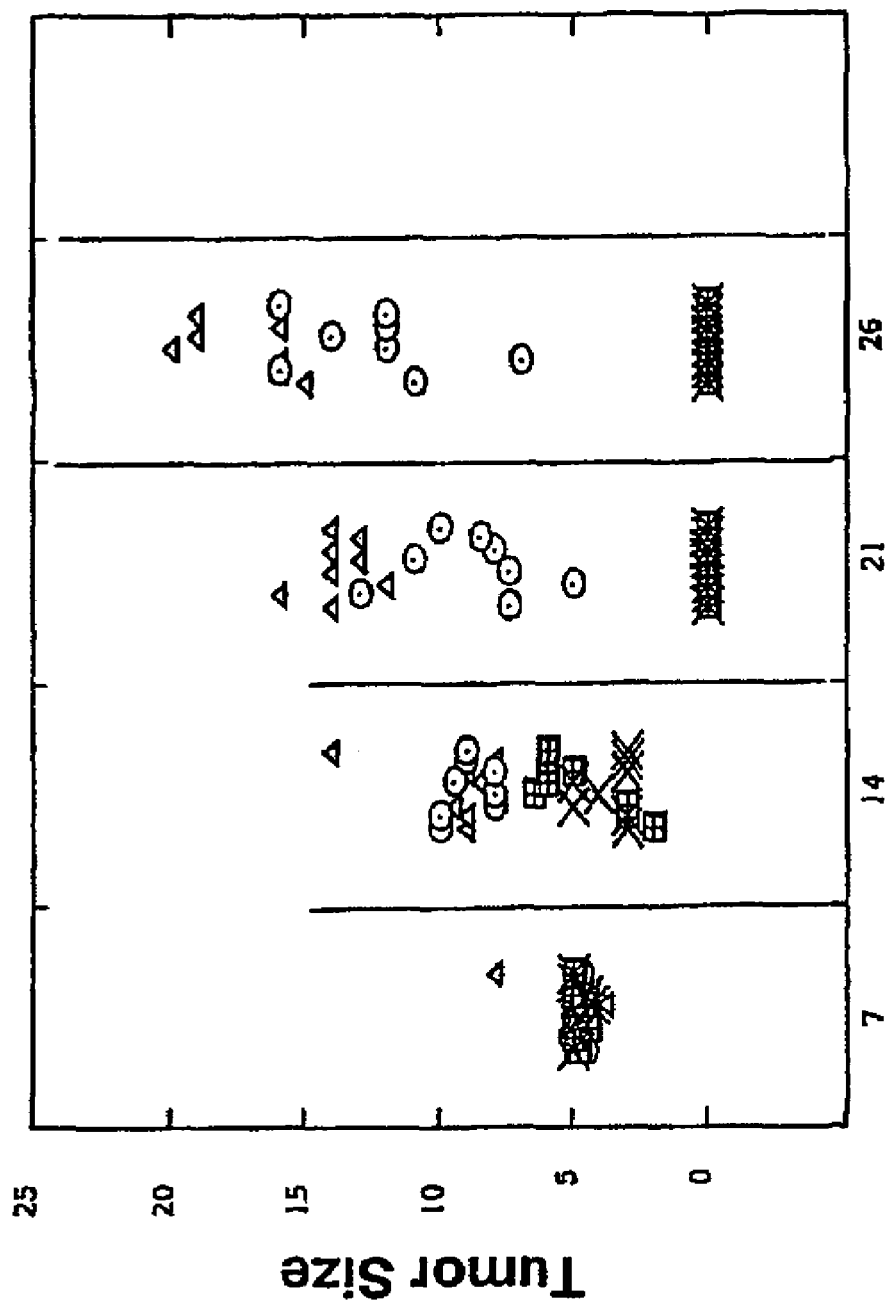
FIG. 9 is a graph depicting tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7 and Lm-E7, $2 \times 10^5$ TC-1 tumor cells were implanted subcutaneously in mice and allowed to grow for 7 days by which time they were palpable (approximately 5 millimeters in size). Mice were then immunized intraperitoneally with one $LD_{50}$ of either Lm-ActA-E7 ($5 \times 10^8$ CFU), (crosses) Lm-LLO-E7 ($10^8$ CFU) (squares) or Lm-E7 ($10^6$ CFU) (circles) on days 7 and 14 following TC-1 cell implantation. Tumor growth was measured periodically with calipers. By day 26, all of the animals in the Lm-LLO-E7 and Lm-ActA-E7 were tumor free and remained so whereas all of the naive animals (triangles) and the animals that were immunized with Lm-E7 grew large tumors (FIG. 9).

Example 9

Ability of Lm-ActA-E7 to Enhance E7 Specific Immunity

To analyze the ability of Lm-ActA-E7 to enhance antigen specific immunity, 500 mcl (microliter) of MATRIGEL™, comprising 100 mcl of 2×10⁵ TC-1 tumor cells in phosphate buffered saline plus 400 mcl of MATRIGEL™ (BD Biosciences, Franklin Lakes, N.J.) were implanted subcutaneously on the left flank of 12 C57BL/6 mice. The mice were divided into 4 groups, 3 mice per group. On day 7, 14 and 21 each group of mice was administered (intraperitoneally) either naive (untreated), Lm-LLO-E7 (1×10⁷ CFU), Lm-E7 (1×10⁶ CFU), or Lm ActA E7 (2×10⁸ CFU). Spleens and tumors were harvested 7 days following the last immunization on day 21. Tumor MATRIGELs were removed from the mice and placed in tubes containing 2 milliliters of RP 10 medium on ice and incubated at 4° C. overnight. The tumors were then minced with forceps, cut into 2 millimeter blocks and treated with 3 ml of enzyme mixture (0.2 mg/ml collagenase-P, 1 mg/ml DNAse-1 in PBS) and incubated at 37° C. for 1 hour. The tissue suspension was then filtered through nylon mesh, washed with 5% fetal bovine serum +0.05% of $NaN_3$ in PBS for tetramer and IFN-gamma staining.

Figure 10:
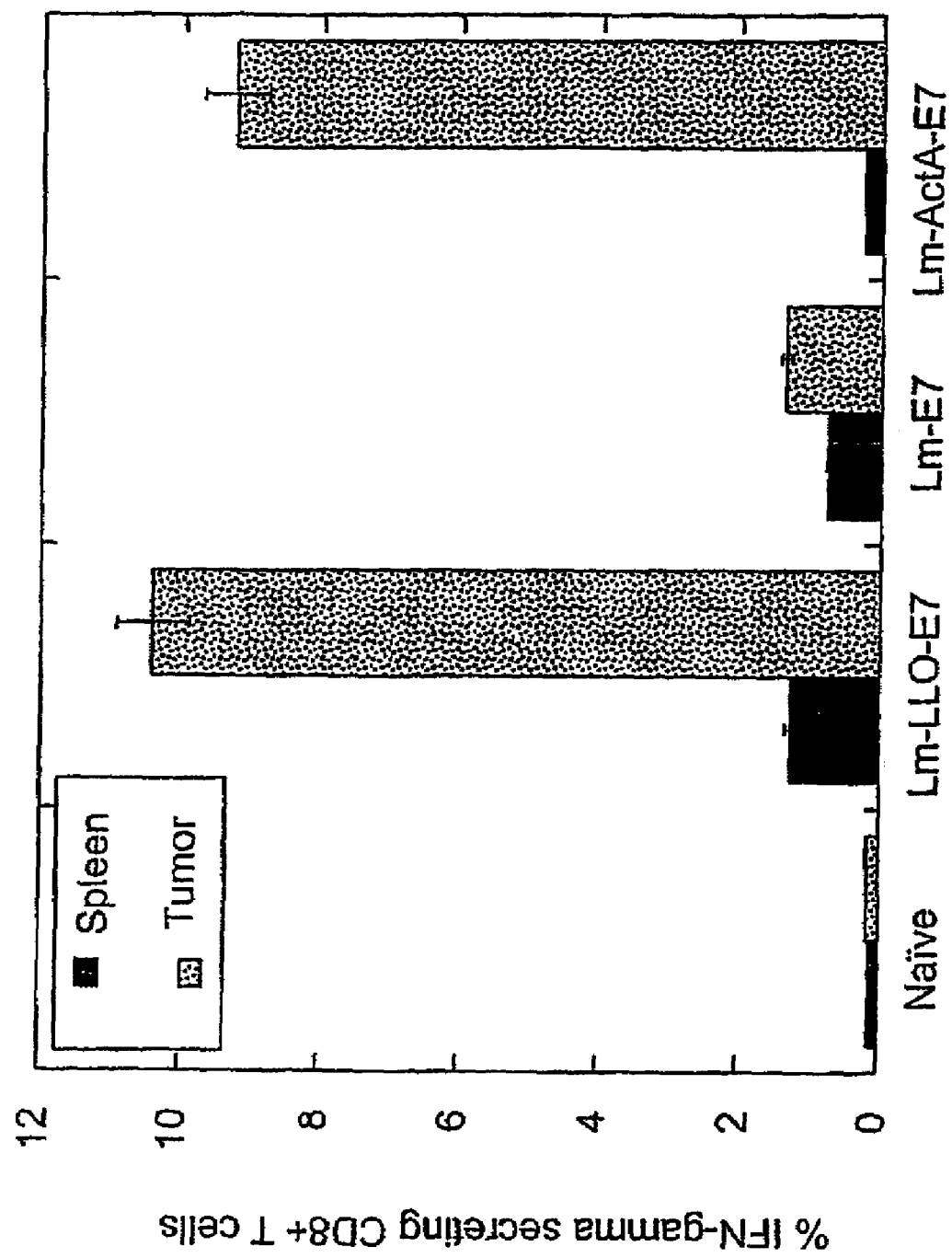
FIG. 10 is a graph depicting the induction of E7 specific IFN-gamma secreting CD8+ T cells in the spleens and tumors of mice administered TC-1 tumor cells and subsequently administered Lm-E7, Lm-LLO-E7, Lm-ActA-E7 or no vaccine (naive).

Splenocytes and tumor cells were incubated with 1 mcm E7 peptide for 5 hours in the presence of the Golgi transport inhibitor brefeldin A at a density of $10^7$ cells/ml. Cells were washed twice and incubated in 50 mcl of anti-mouse Fc receptor supernatant (2.4 G2) for 1 hour or overnight at 4.degree. C. Cells were stained for surface molecules CD8 and CD62L, permeabilized, fixed using the permeabilization kit Golgi-stop or Golgi-Plug (Pharmingen, San Diego, Calif.) and then stained for IFN-gamma. Typically, 500,000 events were acquired using two-laser flow cytometer FACS Calibur and analyzed using Cellquest Software (Becton Dickinson, Franklin Lakes, N.J.). The percentage of IFN-gamma secreting cells within the activated (CD62L low) CD8⁺ T cells was calculated. CD8⁺ T cells secreting IFN-gamma infiltrate the tumors of mice administered Lm-LLO-E7 and Lm-ActA-E7 to a much greater degree than in mice administered Lm-E7 or naive mice (FIG. 10).

Figure 11:
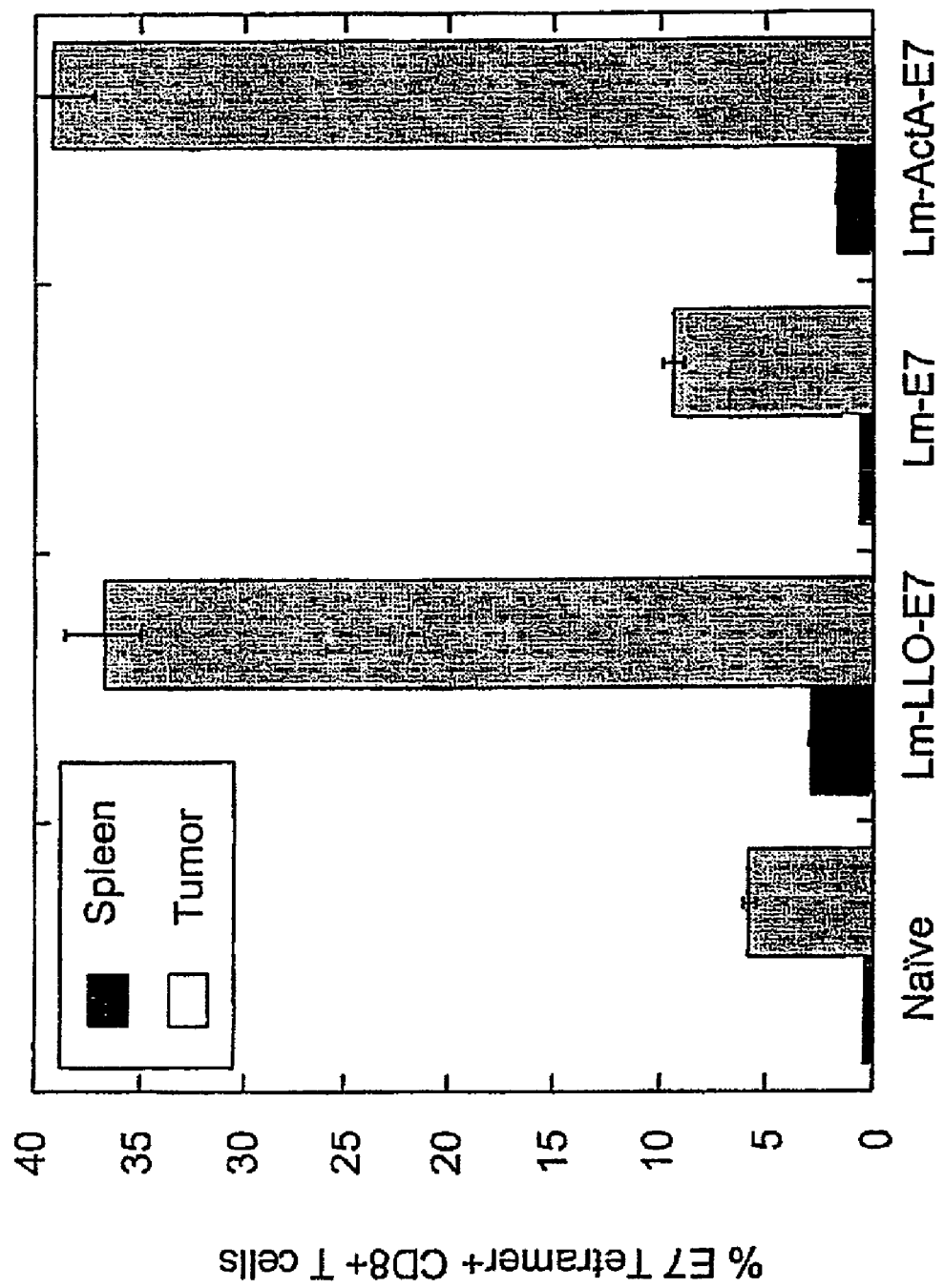
FIG. 11 is a graph depicting the induction and penetration of E7 specific CD8+ cells in the spleens and tumors of mice administered TC-1 cells and subsequently administered a recombinant Listeria vaccine (naive, Lm-LLO-E7, Lm-E7, Lm-ActA-E7).

For tetramer staining, H-2D$^b$ tetramer was loaded with phycoerythrin (PE) conjugated E7 peptide (RAHYNIVTF, SEQ ID NO:22) and stained at room temperature for 1 hour and then stained with anti-allophycocyanin (APC) conjugated MEL-14 (CD62L) and FITC-conjugated CD8.beta. on ice for 30 min. Cells were analyzed comparing tetramer⁺ CD8⁺ CD62L$^{low}$ cells generated by the different recombinant Listeria in the spleen and in the tumor. Lm-ActA-E7 immunized mice produce a greater number of tumor-infiltrating E7 tetramer specific CD8⁺ cells than mice administered Lm-LLO-E7, and a far greater number of tumor-infiltrating E7 tetramer specific CD8⁺ cells than mice administered Lm-E7 and naive mice (FIG. 11).

The data disclosed herein demonstrate a distinct correlation between the numbers of CD8⁺ T cells infiltrating the tumors and the ability of the constructs to kill the tumor. Thus, Lm-LLO-E7 and Lm-ActA-E7 are equally effective at inducing the regression of TC-1 and also induce the largest number of infiltrating CD8⁺ T cells measured as E7 specific IFN-gamma secreting cells or as E7 specific tetramer positive cells.

Example 10

E6/E7 Transgenic Mouse Phenotype

Figure 12:
FIG. 12. E6/E7 transgenic mice develop tumors in their thyroid, where the E7 gene is expressed. Mice were sacrificed at 3 months and had their thyroids removed, sectioned, and stained by h/e. A. Left panel: normal thyroid at 20× magnification. Follicles are of normal size and lined with cuboidal cells with abundant pink cytoplasm (arrow). Right panel: E6/E7 transgenic mouse thyroid. Note the greatly enlarged follicles because of the increased production of colloid. The cuboidal cells lining the follicles are smaller with very little cytoplasm.
Figure 12:

E6/E7 transgenic mouse began to develop thyroid hyperpasia at 8 weeks and palpable goiters at 6 months. By 6 to 8 months, most mice exhibited thyroid cancer. In FIG. 12, transgenic mice were sacrificed at 3 months of age the thyroid demonstrated typical de-differentiation of the normal thyroid architecture, indicative of an early stage of cancer. The enlarged, de-differentiated cells were filled with colloid, where thyroid hormones accumulate (FIG. 12).

Example 11

E7 Message is Detected in Medullary Thymic Epithelial Cells

Figure 13A:
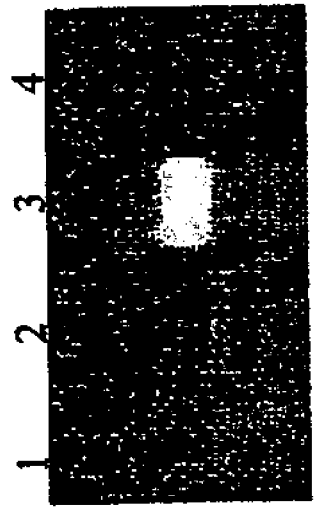
FIG. 13. E7 message is expressed in the thyroid and medullary thymic epithelial cells of the E6/E7 transgenic mouse. A. Tissue-specific expression of the E7 transgene is detected in the thyroid only but not the liver, spleen, or whole thymus. Lane 1: Liver; Lane 2: Spleen; Lane 3: Thyroid; Lane 4: Whole Thymus. B. Medullary thymic epithelial cells (mTECs) express E7; RT-PCR results are as shown for equivalent amounts of cDNA loaded for 40 cycles. Lane 5: Cathepsin S; Lane 6: E7; Lane 7: Actin; and Lane 8: Negative Control.

To determine whether or not E7 was expressed in the thymus, liver, spleen, thymus and thyroid were examined for the expression of the transgene in 6 to 8 week old mice. Abundant E7 message was found in the thyroid but not in other tissues (FIG. 13). The absence of E7 message in whole thymus preparations was not indicative of lack of expression in the thymus, since the level of message of a peripherally expressed, organ-specific antigen, including thyroglobulin, has been shown to be too low to detect in whole thymocyte preparations (Derbinski, J., A. Schulte, B. Kyewski, and L. Klein. 2001. Promiscuous gene expression in medullary thymic epithelial cells mirrors the peripheral self. Nat Immunol 2:1032).

Tolerance to peripheral antigens in the thymus, including thyroglobulin, is mediated by the transient expression of these genes by the autoimmune regulator (AIRE) in thymic medullary epithelial cells (mTECs), with peak expression occurring prior to birth. AIRE is a transcription factor that maintains tolerance to self. To determine whether E7 expression in the transgenic mice followed the same pattern, mTECs from E6/E7 thymi of young mice (3-5 weeks) were examined for E7 expression.

Figure 13B:
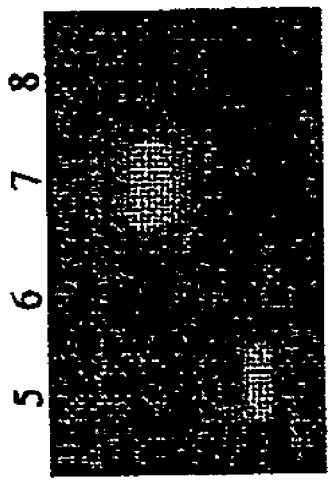

The mTECs expressed E7 message, and also expressed Cathepsin S, which is known to be expressed in mTECs (FIG. 13B). Thus, E7 is expressed in the thymus of the transgenic mice, showing that these mice exhibit tolerance to the E7 antigen.

Example 12

Figure 14:
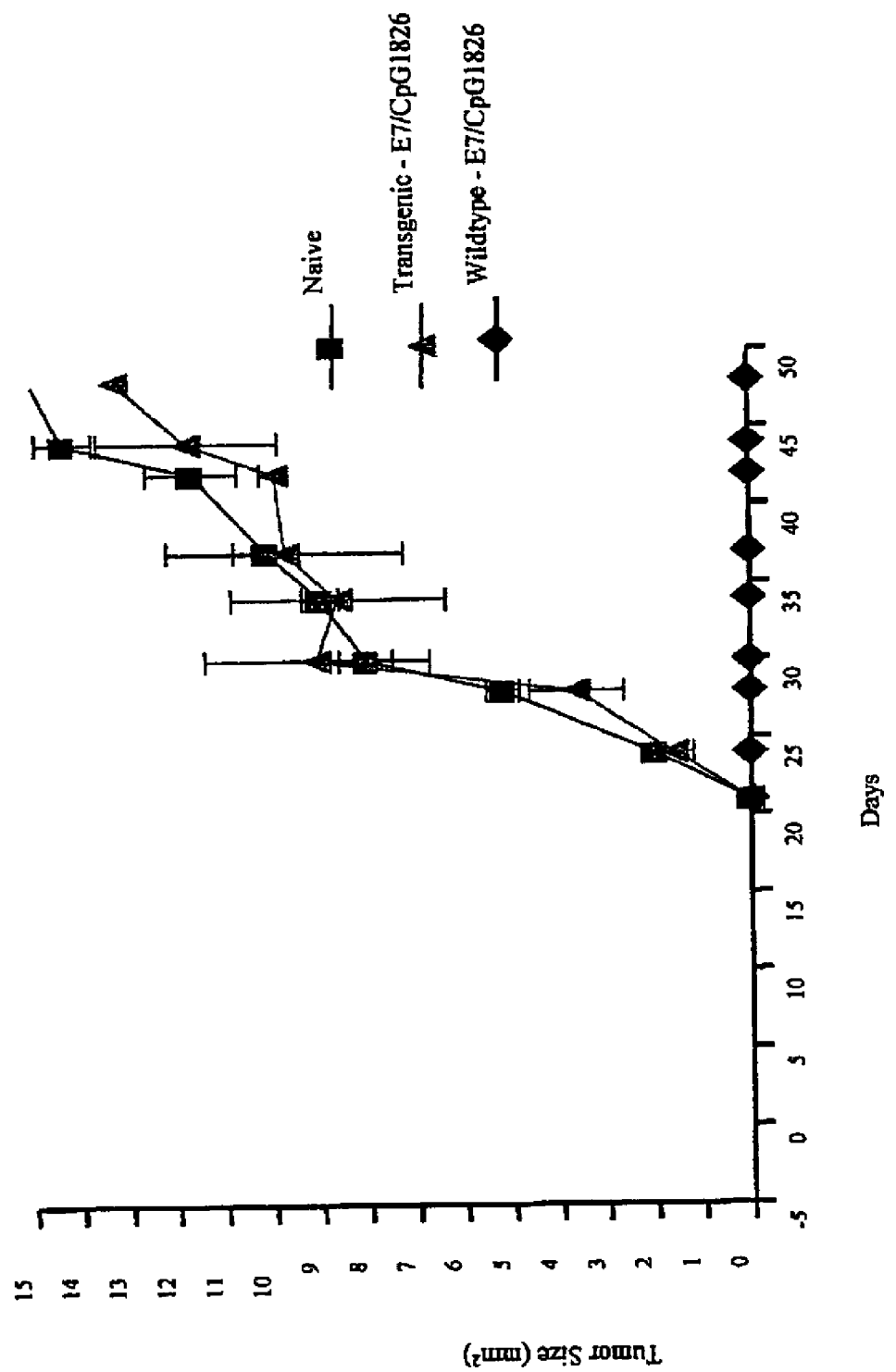
FIG. 14. RAHYNIVTF peptide plus CpG adjuvant fails to protect against TC-1 challenge in E6/E7 transgenic mice. Two groups of transgenic mice received either E7 peptide plus adjuvant or PBS. A third group of wild type C57Bl/6 control mice received E7 peptide plus adjuvant. The mice were vaccinated twice intraperitoneally (i.p.), seven days apart and then challenged with $5 \times 10^4$ TC-1 cells seven days later. Tumors were measured every five days until it was necessary to sacrifice the unimmunized mice. Error bars represent standard deviations from the mean value.

Peptide Based Vaccines are Incapable at Protecting Against Tumor Challenge in the E6/E7 Transgenic Mice As a measure of the impact of the self expression of E7 on vaccine efficacy the E6/E7 transgenic mouse was tested in a classical tumor protection experiment using an E7 peptide (RAHYNIVTF)-based vaccine, along with the immunostimulatory CpG sequence 1826 (Krieg, A. M., A. K. Yi, S. Matson, T. J. Waldschmidt, G. A. Bishop, R. Teasdale, G. A. Koretzky, and D. M. Klinman. 1995. CpG motifs in bacterial DNA trigger direct B-cell activation. Nature 374:546) While the peptide based vaccine was able to protect all the wild type mice from tumor challenge, it had no impact on tumor challenge in the transgenic mouse (FIG. 14). Thus, the E6/E7 mice exhibit reduced ability to reject tumor challenge, providing further evidence that they are tolerant to E7.

Example 13

Figure 15A:
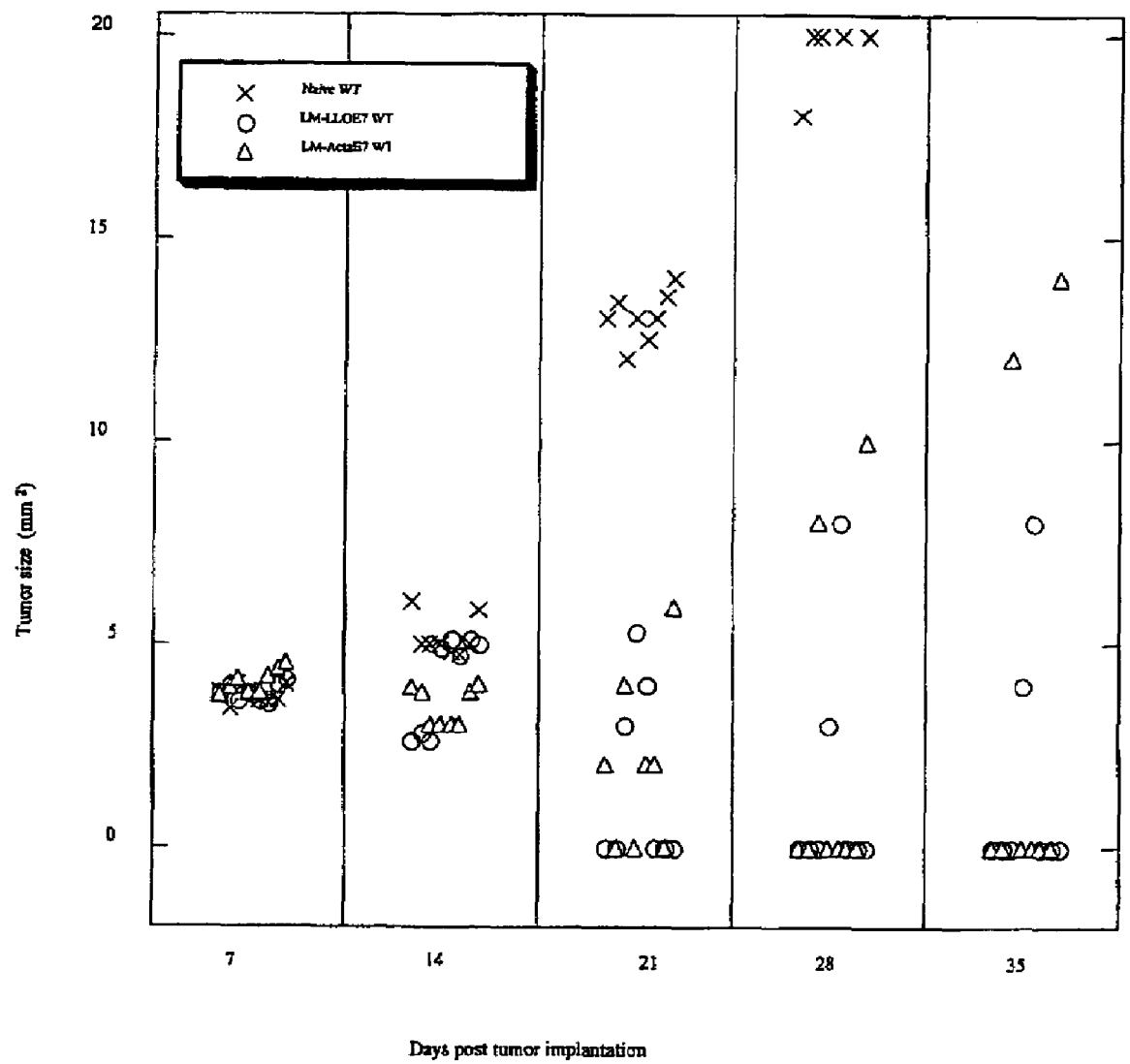
FIG. 15. Vaccines of the present invention induce regression of solid tumors in the E6/E7 transgenic mice in wild-type mice (A) and transgenic mice (B). $1 \times 10^5$ TC-1 tumor cells were implanted s.c. at day 0. When palpable tumors formed seven days later, mice were i.p. immunized with $1 \times 10^8$ LM-LLO-E7, $2.5 \times 10^8$ LM-ActA-E7, left naïve, or treated with LM-NP as a control. Mice were boosted with the same vaccine on day 14. Every seven days, tumors were measured using a caliper in two dimensions, then plotting the average of those values. Depicted are results from 1 of 2 experiments; very similar results were obtained in the repetition.
Figure 15B:
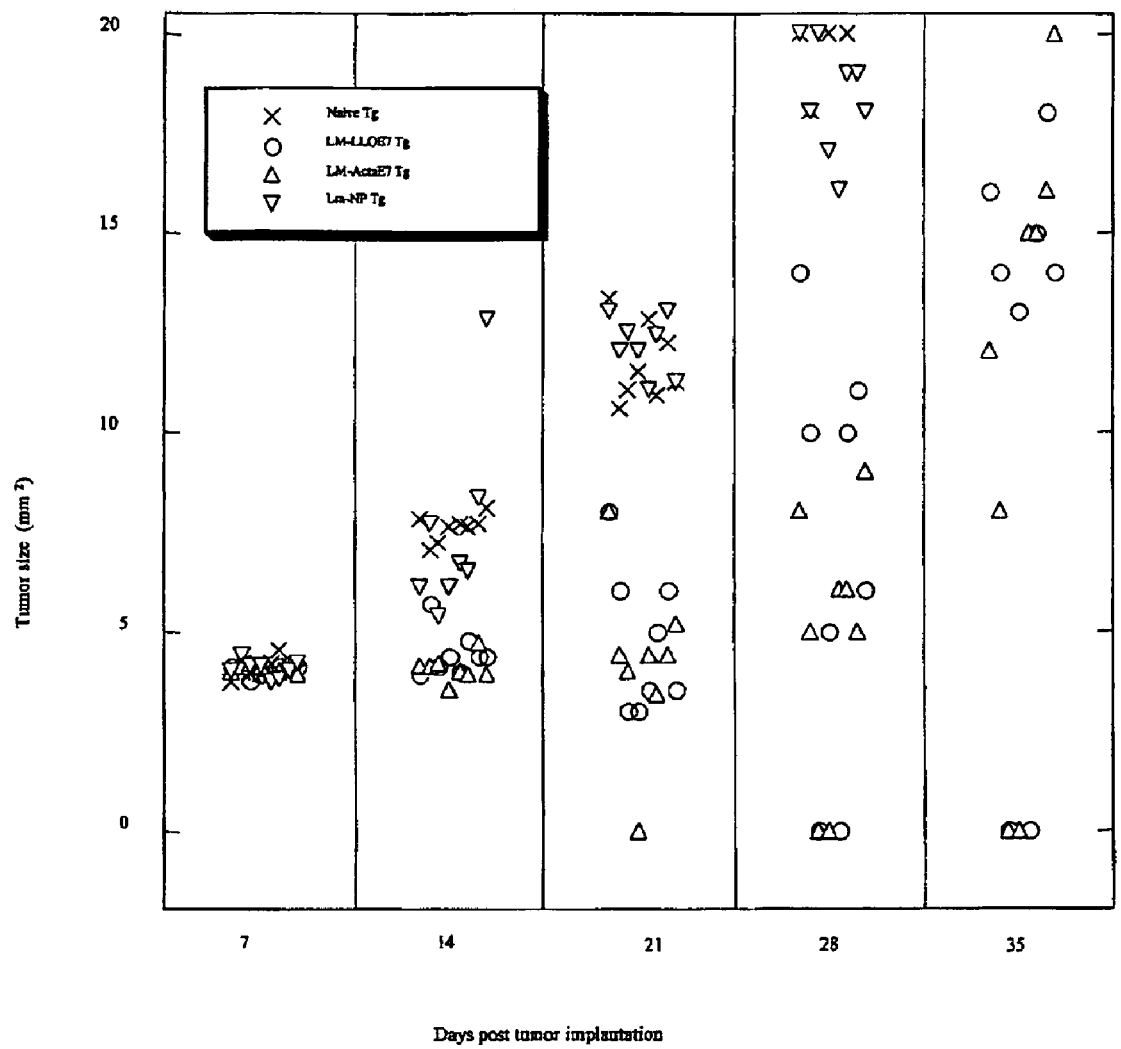

Vaccines of the Present Invention Overcome Immune Tolerance of E6/E7 Transgenic Mice to E7-Expressing Tumors To examine the ability of vaccines of the present invention to overcome the immune tolerance of E6/E7 transgenic mice to E7-expressing tumors, TC-1 cells were implanted subcutaneously (s.c.) and allowed to form solid tumors in 6-8 week old wild type (FIG. 15A) and transgenic mice (FIG. 15B). Seven days and fourteen days later, mice were immunized with LM-NP, LM-LLO-E7, or LM-ActA-E7, or left unimmunized. Naïve mice and mice immunized with LM-NP had large tumor burden, as anticipated, and were sacrificed by day 28 or 35 due to tumors of over 2 cm. By contrast, by day 35, administration of either LM-LLO-E7 or LM-ActA-E7 resulted in complete tumor regression in ⅚ of the wild type C57Bl/6 mice and ⅔ of the transgenic mice, further confirming that E6/E7 transgenic mice exhibit tolerance to E7-expressing tumors. Even in the transgenic mice that did not exhibit complete tumor regression, a marked slowing of tumor growth was observed relative to the naïve and LM-NP-treated mice. The effectiveness of vaccines of the present invention in inducing complete tumor regression in some E6/E7 transgenic and slowing tumor growth in the other transgenic mice is in marked contrast to the inefficacy of the peptide-based vaccine (FIG. 14). Thus, vaccines of the present invention were able to overcome immune tolerance of E6/E7 transgenic mice to E7-expressing tumors.

Example 14

Figure 16:
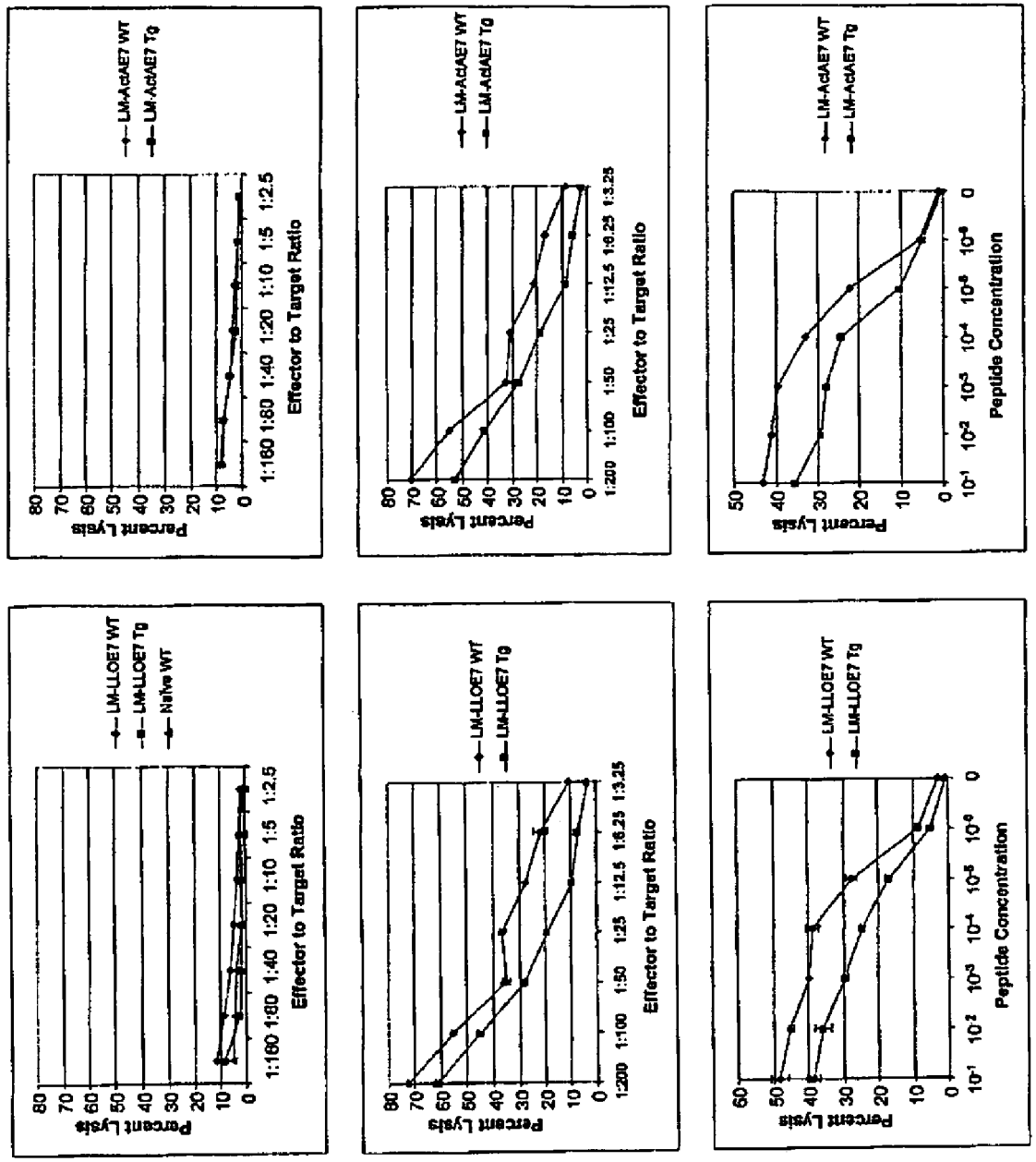
FIG. 16. CTL responses generated in E6/E7 transgenic mice vs. wild-type C57Bl/6 mice. Mice were immunized with $1 \times 10^8$ LM-LLO-E7 or $2.5 \times 10^8$ LM-ActA-E7 on days 0 and 7. On day 14, splenocytes were removed and cultured with irradiated TC-1 cells for 5 days. Following this culture step, splenocytes were used in a $^5$Cr release assay after a 4-hour incubation. Top panel: EL4 alone; middle panel: EL4 pulsed with 1 µM of peptide with differing effector cell: target cell (E:T) ratios; bottom panel: EL4 plus differing concentrations of peptide with an E:T ratio of 50:1. Triplicate wells were performed; the mean number is plotted, and error bars represent the standard deviation. Depicted are results from an experiment representative of 3 experiments.

Vaccines of the Present Invention Overcome Relatively Low CTL Avidity and Smaller CTL Responses Accompanying Tolerance to Self Antigens To compare the avidity of the anti-E7 cytotoxic CD8+ T lymphocytes (CTL) response of the E6/E7 transgenic mouse vs. the wild-type mouse, target cell killing was utilized as a marker of functional avidity. Splenocytes were isolated from immunized transgenic or age-matched wild type mice and expanded in culture for 5 days in the presence of TC-1 feeder cells and IL-2. Cytolytic activity was then measured in a standard $^{51}$Cr release assay, using the syngeneic EL4 cells as targets. A small amount of nonspecific killing was observed in both strains of mice in the absence of E7 peptide. In the presence of peptide, a CTL response capable of target cell killing was elicted in both strains of mice, but the CTL produced in the E6/E7 transgenic mouse killed a smaller fraction of the target cells at any given effector: target ratio (FIG. 16). Similarly, at a constant effector: target ratio, CTL from the E6/E7 transgenic mice required a higher concentration of peptide to display equivalent amount specific lysis. Thus, CTL in the repertoire of E6/E7 transgenic mice exhibit a lower functional avidity compared to the WT mouse.

In addition, using ex vivo tetramer staining, it was shown that lower numbers of CD8+ CD62L$^{low}$ tetramer+ cells were induced by the LLO-E7 and ActA-E7 vaccines in the transgenic mice (about 2 to 4%) compared to wild type mice (about 8 to 12%). Thus, the magnitude of CTL responses is lower in E6/E7 transgenic mice compared to WT mice.

Thus, CTL in the repertoire of E6/E7 transgenic mice exhibit a lower functional avidity compared to WT mice. The ability of vaccines of the present invention to cause regression of and inhibit growth of E7-expressing tumors in the E6/E7 transgenic mouse (Example 13) shows that these vaccines exhibit the ability to overcome lower CTL avidity and smaller CTL responses accompanying tolerance to self antigens.

Example 15

Figure 17A:
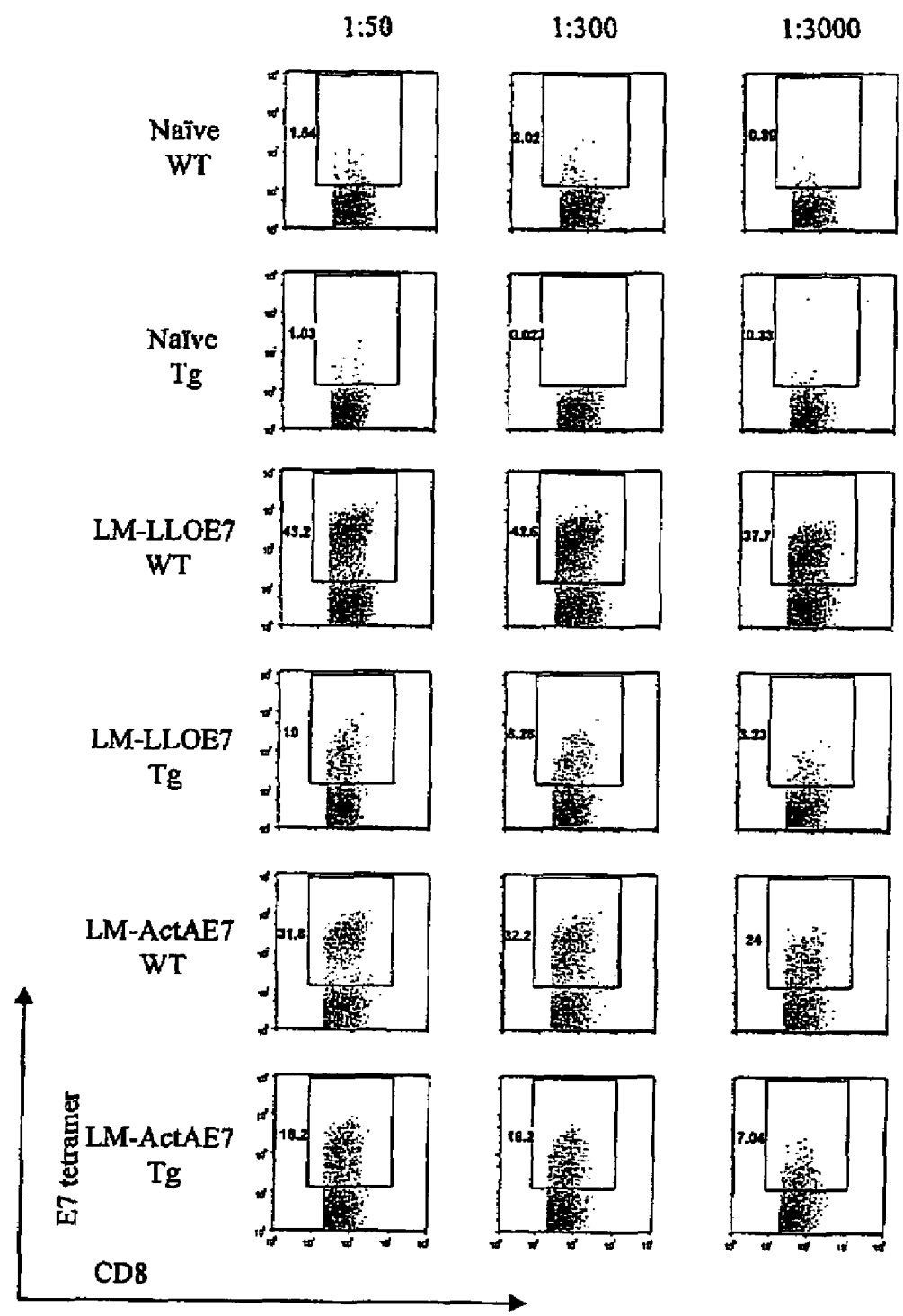
FIG. 17. Titration of the RAHYNIVTF-loaded tetramer demonstrates that the TILS induced in the C57Bl/6 mice have a higher avidity than those in the E6/E7 transgenic mouse. $1 \times 10^5$ TC-1 tumor cells in Matrigel® were implanted subcutaneously (s.c.) for both C57Bl/6 and E6/E7 transgenic mice. Seven days later, when palpable tumors about 5 mm in size formed, mice were immunized i.p. with $1 \times 10^8$ LM-LLO-E7, $2.5 \times 10^8$ LM-ActA-E7, or left untreated. Mice were boosted on day 14 with the same vaccine dose. On day 21, mice were sacrificed, and each group had tumors pooled together, digested with collagenase, crushed, filtered, and made into a single cell suspension. Cells were stained for CD62L, CD8a, CD11b, and the H-2 Db tetramer loaded with RAHYNIVTF peptide at the indicated dilutions. 7AAD was used as a viability dye. A. Cells depicted were positive for CD8a and the E7 tetramer, were negative for 7AAD and CD11b, and were low for CD62L. B. Histograms depicted were gated from the data in (A) and overlaid, with the MFI depicted in Table 3. Depicted are results from 1 of 2 experiments; very similar results were obtained in the repetition.
Figure 17B:
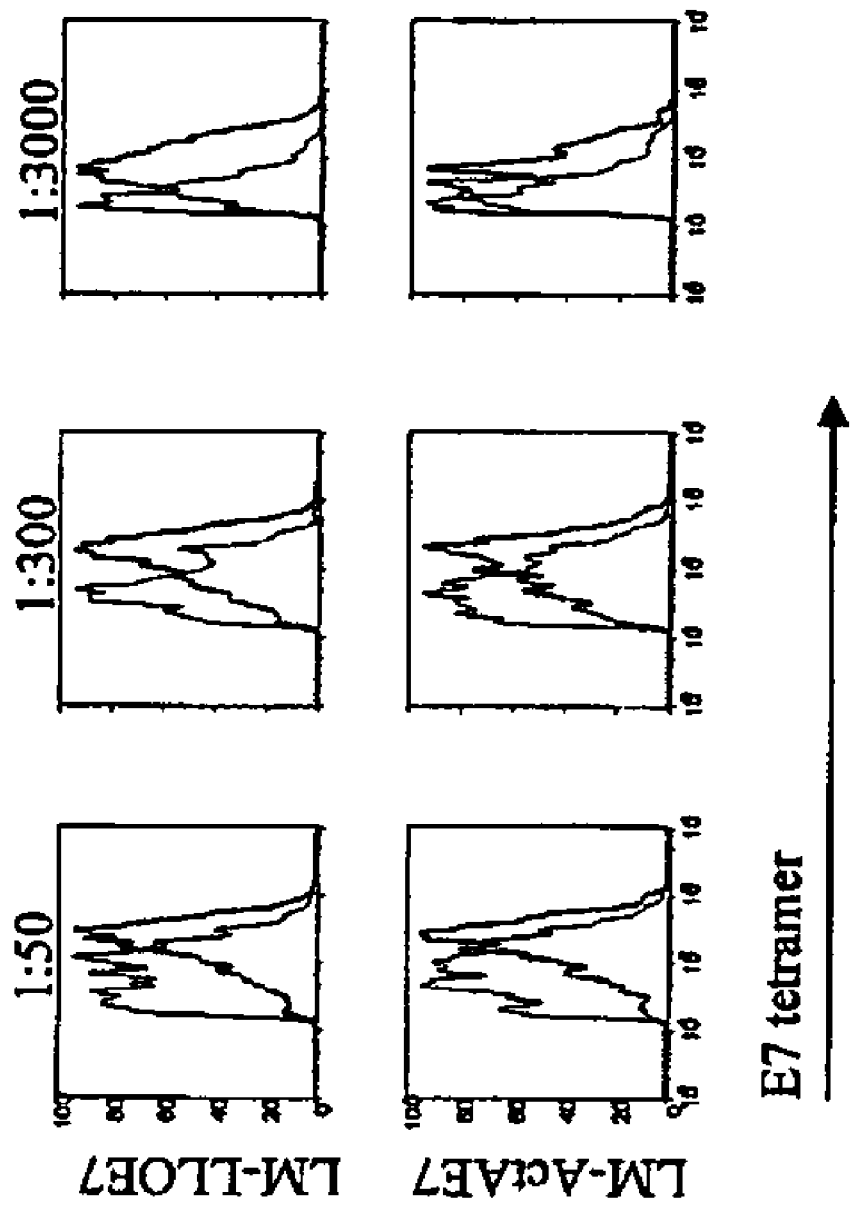

Tumor Infiltrating Lymphocytes in E6/E7 Mice are of a Lower Avidity than Wild-Type C57Bl/6 Mice Next, the avidity of tumor-infiltrating lymphocytes (TIL) was determined by flow cytometry in the E6/E7 and syngenic wild-type mice. Following vaccination with either LM-LLO-E7 or LM-ActA-E7, effector CD8+ T cells were present at a higher frequency in the wild type mice vs. the transgenic mouse at each concentration of tetramer, while TILS from naïve mice exhibited only background levels of staining (FIG. 17A). In addition, at the highest concentration of tetramer (1:50), TIL from the wild-type mice bound the tetramer with a two-fold higher mean channel fluorescence intensity (MFI) than the transgenic mice (Table 3), indicating that the TIL induced in the wild-type mice were of higher avidity. Similar results were observed at 1:300 and 1:3000 dilutions. Table 3 is a summary of FIG. 17B, in which the CD8+ CD62L$^-$ tetramer+ T cells were displayed as a histogram.]. Thus, the TIL generated in the E6/E7 mice are of lower avidity compared wild-type C57Bl/6 mice.

TABLE 3

Mean fluorescent intensity of tetramer staining of CD8+ TILs from normal and transgenic mice vaccinated with Lm-LLO-E7 or Lm-ActA-E7.

| | | Tetramer dilution | | |
|---|---|---|---|---|
| Lm E7 vaccine | Mouse | 1:50 | 1:300 | 1:3000 |
| Lm-LLO-E7 | Wild-type | 248 | 186 | 98 |
| Lm-LLO-E7 | E6/E7 transgenic | 111 | 86 | 38 |
| Lm-ActA-E7 | Wild-type | 255 | 169 | 77 |
| Lm-ActA-E7 | E6/E7 transgenic | 128 | 89 | 45 |

Thus, TIL induced in E6/E7 transgenic mice exhibit a lower functional avidity compared to WT mice. The ability of vaccines of the present invention to infiltrate (present Example) and control tumor growth of (Example 13) E7-expressing tumors in the E6/E7 transgenic mouse shows that these vaccines exhibit the ability to overcome lower avidity of TIL accompanying tolerance to self antigens.

Example 16

Generation of Lm Strains that Secrete LLO Fragments Fused to her-2 Fragments

Materials and Experimental Methods

Figure 18:
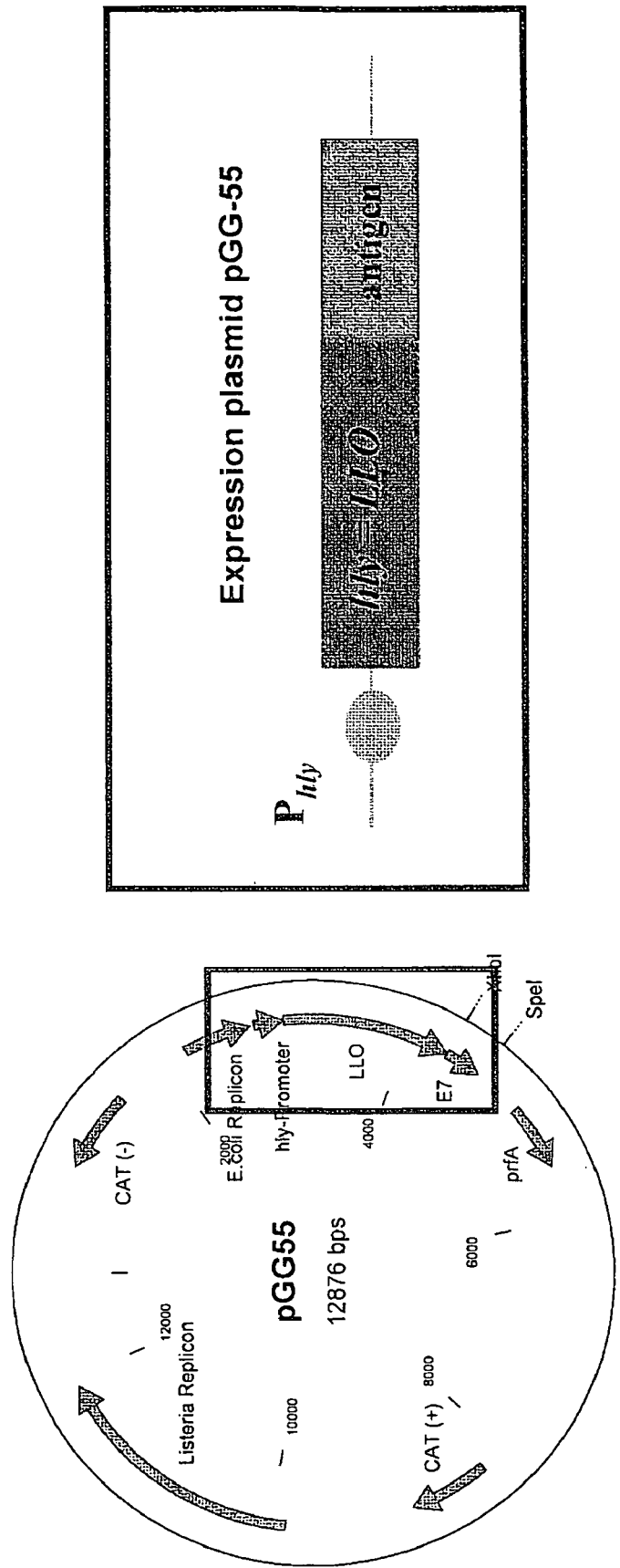
FIG. 18. Schematic representation of pGG55, used to construct the Lm-Δ-LLO-HER-2 vaccines.

Subcloning pGG-55, the backbone of the *Listeria* Her-2 constructs used in the Examples below, was created from pAM401. pAM401, a shuttle vector able to replicate in both gram+ and gram$^-$ bacteria, contains a gram+ chloramphenicol resistance gene and a gram$^-$ tetracycline resistance gene (Wirth, R et al, J Bacteriol, 165: 831, 1986). To produce pGG-55, an hly-HPV 16 E7 fusion gene (including the hly promoter and the portion of hly encoding the first 441 amino acids of LLO; referred to below as "ΔLLO" and having the sequence set forth in SEQ ID No: 25) and the pluripotent transcription factor, prfA (positive regulatory factor of listeriolysin expression) gene were cloned into pAM401 (FIG. 18).

Figure 19:
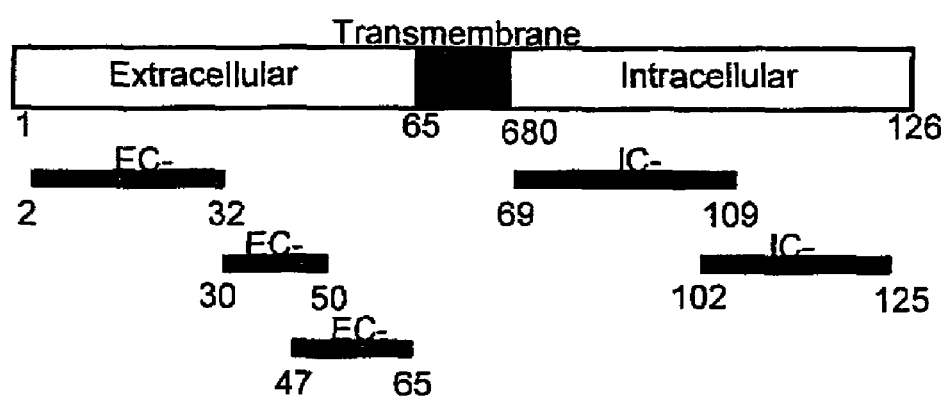
FIG. 19. Recombinant Listeria monocytogenes is capable of secreting each of Her-2 fragments as a ΔLLO-fusion protein. (A) Map of rat Her-2 fragments. (B) Confirmation of secretion of the fusion peptides by Western blot. Marker (lane 1), Lm-ΔLLO-E7 (lane 2), Lm-ΔLLO-EC1 (lane 3), Lm-ΔLLO-EC2 (lane 4), Lm-ΔLLO-EC3 (lane 5), Lm-ΔLLO-IC1 (lane 6), and Lm-ΔLLO-IC2 (lane 7).
Figure 19:
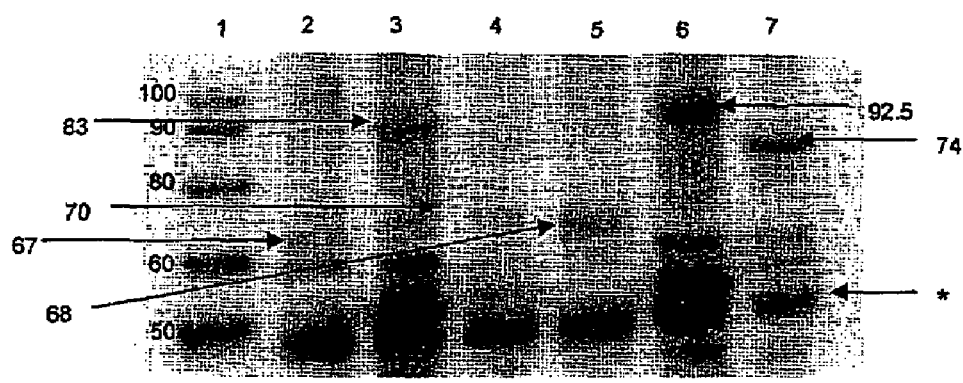

L. monocytogenes (LM) strains Lm-ΔLLO-EC1, Lm-ΔLLO-EC2, Lm-ΔLLO-EC3, Lm-ΔLLO-IC 1, and Lm-ΔLLO-IC2 each contain a plasmid expressing a fragment of rat Her-2 fused to a fragment of the Listerial hly gene (hly encodes LLO). The following overlapping fragments of the extracellular and intracellular domains of Her-2 were cloned into the plasmid pGG-55: base pairs (bp) 74-994, (Lm-ΔLLO-EC1; corresponding to AA 20-326 of Her-2), 923-1519 (Lm-ΔLLO-EC2; corresponding to AA 303-501), 1451-1981 (Lm-ΔLLO-EC3; corresponding to AA 479-655), 2084-3259 (Lm-ΔLLO-IC1; corresponding to AA 690-1081), and 3073-3796 (Lm-ΔLLO-IC2; corresponding to AA 1020-1255). The fragments are depicted in FIG. 19A. The $LD_{50}$ of EC1, EC2, EC3, IC1, and IC2 were $1\times10^8$, $1\times10^9$, $5\times10^8$, $1\times10^8$, and $1\times10^8$, respectively.

Each Her-2 fragment was amplified by PCR from the pNINA plasmid, which contains the full-length rat Her-2 gene, using the following primers. Restriction sites (XhoI in the case of EC1, IC1, and IC2 5' primers; SpeI for the 3' primers; and SalI for the EC2 and EC3 5' primers) are underlined, and the FLAG tag sequence in the EC2 and EC3 the 3' primers are indicated by italics:

```
EC1:
5' primer:   CACGCGGATGAAATCGATAAGCTC   (SEQ ID No:26)
             GAGCCCCCCGGAATCGCGGGCAC;

3' primer:   CCGGACTAGTGACCTCTTGGTTAT   (SEQ ID No:27)
             TCGGGGACACACC.

EC2:
5' primer:   CCGGGTCGACTGCCCCTACAACTA   (SEQ ID No:28)
             CCTGTCTACG;

3' primer:   CCGGACTAGTTTACTTGTCATCGT   (SEQ ID No:29)
             CGTCCTTGTAGTCCCCAC;

EC3:
5' primer:   CCGGGTCGACTGCTTTGTACACAC   (SEQ ID No:30)
             TGTACCTTGG;

3' primer:   CCGGACTAGTTTACTTGTCATCGT   (SEQ ID No:31)
             CGTCCTTGTAGTCCGGGCTGGCTC
             TCTGCTCTGC;

IC1:
5' primer:   CCGGCTCGAGTATACGATGCGTAG   (SEQ ID No:32)
             GCTGCTGCAGG;

3' primer:   CCGGACTAGTAGCCAGTGGAGATC   (SEQ ID No:33)
             TGGGGGGCCC;

IC2:
5' primer:   CCGGCTCGAGGGTGACCTGGTAGA   (SEQ ID No:34)
             CGCTGAAG
and 3' primer:   CCGGACTAGTTACAGGTACATCCA   (SEQ ID No:35)
             GGCCTAGG.
```

Fragments were amplified by PCR and cloned into the pCR 2.1 expression system (Invitrogen, Carlsbad, Calif.), then excised with the delineated enzymes. The E7 gene was excised from the pGG-55 plasmid using Xho I and Spe I, then the Her-2 fragment was fusion was ligated into the E7 site (ends digested with Sal I are compatible with XhoI ends). XFL-7, a prfA negative strain of LM, (Gunn G R et al, J Immunol 167: 647, 2001) was transfected with the plasmids by electroporation.

Bacteria

Bacteria were grown in brain heart infusion medium (BD, Sparks, MD) with 50 µg/ml chloramphenicol and were frozen in 1 ml aliquots at −80° C.

Western Blots

ΔLLO-Her-2 expressing strains were grown overnight at 37° C. in Luria-Bertani (LB) medium with 50 microgram per milliliter (µg/ml) chloramphenicol. Supernatants were TCA precipitated and resuspended in 1×LDS sample buffer (Invitrogen, San Diego, Calif.). 15 microliter (µl) of each sample was loaded on a 4-12% Bis-Tris SDS-PAGE gel (Invitrogen. San Diego, Calif.). Gels were transferred to a Immobilon-P polyvinylidene fluoride membrane (Millipore, Billerica, Mass.) and blotted with a polyclonal rabbit serum recognizing residues 1-30 of LLO, followed by HRP-conjugated anti-rabbit antibody (Amersham Pharmacia Biotech, UK).

Statistical Analyses

Statistical analyses were performed using Student's t-test throughout the Examples below.

Results

Five recombinant LM strains were constructed that express and secrete overlapping fragments of the rat Her-2 gene fused to the N-terminal portion of L. monocytogenes LLO protein (FIG. 19A). The signal sequence and transmembrane domain of Her-2 were not included among the fragments due to their hydrophobicity and the inability of LM to secrete extremely hydrophobic domains. Secretion of each Her-2 fragment was confirmed by Western blot (FIG. 19B). Molecular weights of the proteins Lm-ΔLLO-EC1 Lm-ΔLLO-EC2 Lm-ΔLLO-EC3, Lm-ΔLLO-IC1, and Lm-ΔLLO-IC2 were 83, 70, 68, 92.5, and 74-kDa (kilodalton), respectively. The strains were attenuated relative to the wild-type 10403S strain, exhibiting virulences comparable to Lm-ΔLLO-E7; namely $1\times10^8$, $5\times10^8$, $1\times10^9$, $1\times10^8$, and $1\times10^8$ colony forming units (CFU), respectively.

Example 17

Vaccination with LLO-Her-2 Constructs Halts and Reverses Growth of Her-2-Expressing Tumors Materials and Experimental Methods Mice Six to eight week old female FVB/N mice were purchased from Charles River Laboratories (Wilmington, Mass.).

Cell Lines

The FVB/N syngeneic NT-2 tumor cell line, derived from a spontaneously occurring mammary tumor in an FVB/N Her-2 transgenic mouse (Reilly R T et al, Canc Res 60: 3569, 2000), constitutively expresses low levels of rat Her-2 and is tumorigenic in wild type syngeneic mice. NT-2 cells were grown in RPMI 1640 medium with 20% FCS, 10.2 mM HEPES, 2 millimolar (mM) L-glutamine, 100 micromolar (µM) nonessential amino acids, 1 mM sodium pyruvate, 50 U (units)/ml penicillin G, 50 µg/ml streptomycin, 20 µg/ml insulin, and 2 µg/ml gentamycin at 37° C. with 5% $CO_2$.

Experimental Setup 6-8 week-old FVB/N mice (n=8) were injected subcutaneously in the right flank with $2\times10^6$ NT-2 tumor cells in 200 µl PBS. Seven days post-tumor inoculation, palpable tumors of 4-5 mm were observed, after which mice were injected intraperitoneally with recombinant LM or PBS on days 7, 14, and 21. The shortest and longest surface diameters of the tumors were measured every 2 days with calipers. Mice were sacrificed if they reached a point at which mean tumor diameter reached 20 mm.

Results

Figure 20:
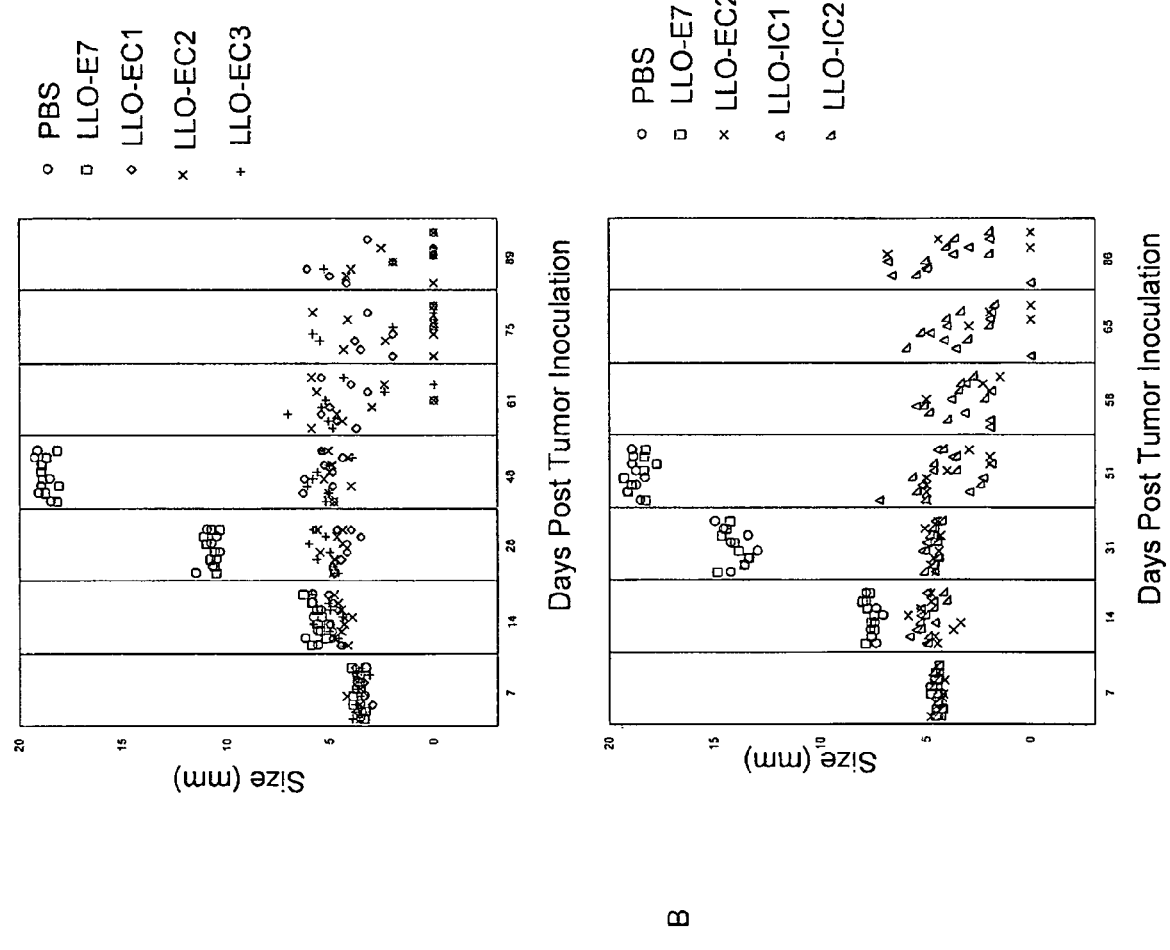
FIG. 20. Lm-ΔLLO-Her-2 vaccines each induce a halt in tumor growth of established NT-2 tumors in wild-type FVB mice. Each data point represents the average of shortest and longest surface tumor diameter of one mouse at a given time point. Mice were sacrificed when the average tumor diameter reached 2.0 cm; tumor measurements are only shown for the surviving mice at a given time point. Representative figures of two experiments are shown. (A) Lm-ΔLLO-EC1, Lm-ΔLLO-EC2, and Lm-ΔLLO-EC3; (B) Lm-LLO-IC1, and Lm-ΔLLO-IC2.

LM strains expressing ΔLLO-Her-2 fusions were compared to PBS and Lm-ΔLLO-E7 (negative controls) for their ability to induce immunity against and reduction of tumors composed of the rat Her-2 expressing tumor line, NT-2. FVB/N mice were injected with NT-2 tumors, then, on days 7, 14, and 21 following tumor inoculation, were administered 0.1 $LD_{50}$ of recombinant LM or PBS. Injection of LM expressing the ΔLLO-Her-2 fusions halted tumor growth after the first injection (FIGS. 20A and B); the cessation in tumor growth continued through the last timepoint, more than nine weeks after the last Her-2 vaccination. Moreover, a complete regression of tumors was subsequently observed in three out of 8 of the Lm-ΔLLO-EC2 and Lm-ΔLLO-EC3 mice and 1 of 8 of the Lm-ΔLLO-EC1 and LM-ΔLLO-IC1 mice. Additional mice from all five of the ΔLLO-Her-2 groups exhibited a reduction in tumor size. As expected, tumors grew continually in mice injected with PBS and Lm-ΔLLO-E7.

These findings demonstrate that fusions of a LLO fragment to Her-2 are capable of eliciting immunity against Her-2-expressing tumors. These findings further indicate that the elicited immunity (a) is strong enough to induces the complete regression of greater than 75% of established Her-2-expressing tumors; and (b) lasts over the course of over at least several months. Thus, vaccines of the present invention are efficacious for induction of regression of tumors and inhibition of tumor growth with either Her-2 or E7, showing that findings of the present invention are generalizable to all antigens. In addition, a number of different PEST-like sequences can be used (either LLO or ActA), showing that findings of the present invention are generalizable to all PEST-like sequences.

Example 18

IMMUNE Responses Induced by the Lm-LLO-Her-2 Vaccine Include CD8⁺ T Cells

Materials and Experimental Methods

CD8⁺ T Cell Depletion

CD8⁺ T cells were depleted by injection with 0.5 mg of the anti-CD8 antibody 2.43 (Sarmiento M et al, J Immunol 125 (6): 2665-72, 1980) on days 6, 7, 8, 11, 14, 17, 20, and 23 post-tumor injection. CD8⁺ T cell populations were reduced by greater than 95%, as measured by flow cytometric analysis on day 24.

Flow Cytometric Analysis

Three color flow cytometry for CD8 (53-6.7, FITC conjugated), CD62 ligand (Mel-14, APC conjugated) (BD Biosciences Pharmingen, San Diego, Calif.), and Her-2H-$2^q$ tetramer (PE conjugated) was performed using a FACSCalibur flow cytometer with CellQuest software (Becton Dickinson, San Jose, Calif.). Tetramers, provided by the NIAID Tetramer Core Facility of Emory University and the NIH AIDS Research and Reference Reagent Program, were loaded with an H-$2^q$ specific PDSLRDLSVF peptide. Splenocytes were stained at room temperature (rt) with the tetramer for one hour (hr) at 1:200 dilution, then at 4° C. with anti-CD8 and anti-CD62L antibodies for 30 minutes (min). The CD8⁺, CD62L$^{low}$ subset was selected ("gated on"), and percentages of tetramer⁺ cells were compared using FlowJo software (Tree Star, Inc, Ashland, OR.).

Results

Figure 21:
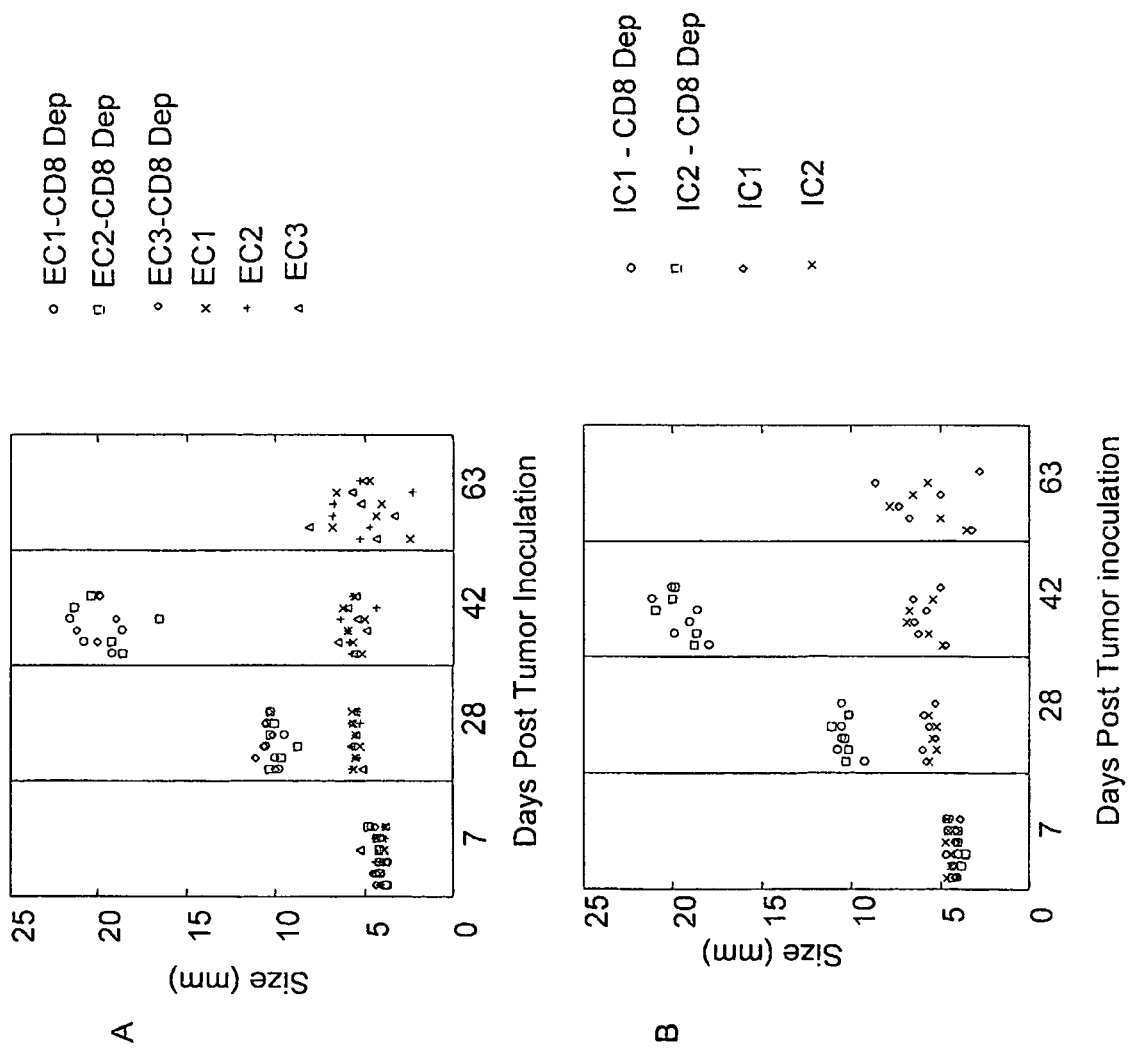
FIG. 21. CD8+ T cells participate in Lm-LLO-Her-2 induced tumor stasis. Tumor measurements are shown only for the surviving mice at a given time point. (A) Lm-ΔLLO-EC1, Lm-ΔLLO-EC2, and Lm-ΔLLO-EC3 both depleted and not depleted for CD8+ T cells. (B) Lm-ΔLLO-IC1 and Lm-ΔLLO-IC2 both depleted and not depleted for CD8+ T cells.

To determine the type of T cells that were mediating the observed anti-Her-2 immune responses, FVB/N mice with NT-2 tumors were depleted of CD8⁺ T cells, beginning 1 day prior to vaccination with Lm-ΔLLO-Her-2 vaccines, then vaccinated as described in Example 17. In the anti-CD8⁺-injected mice, each of the Lm-ΔLLO-Her-2 vaccines lost effectiveness (FIG. 21A-B); while in the non-depleted mice, tumor growth was controlled, as observed in Example 17.

Figure 22:
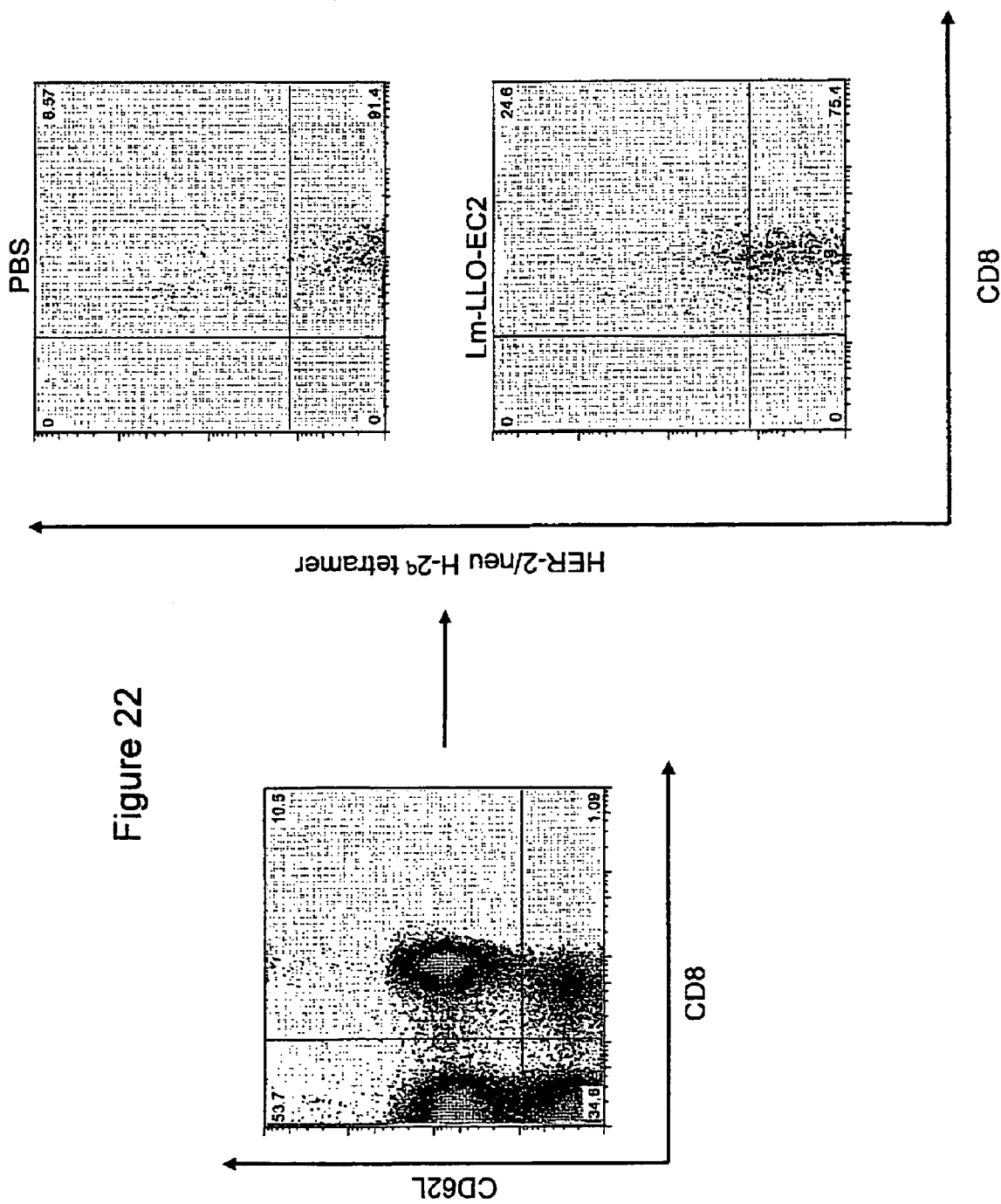
FIG. 22. Lm-ΔLLO-EC2 induces a 3-fold increase in tetramer+, CD8+ T cells. FVB/N mice were immunized with Lm-ΔLLO-EC2 or PBS. Subsequently, splenocytes were stained with an H-2$^q$ Her-2 tetramer, anti-CD8, and anti-CD62L.

Tetramer analysis was next used to confirm the above results. Non-tumor bearing 6-8 week-old FVB/N mice were immunized with either PBS or 0.1 $LD_{50}$ Lm-ΔLLO-EC2 and boosted 21 days later. Splenocytes were harvested 5 days after the boost and were stained with an H-$2^q$ tetramer specific for the epitope defined by amino acids 420-429 (PDSL-RDLVF; SEQ ID No: 36). A three-fold increase in tetramer positive cells was observed in the Lm-ΔLLO-EC2-vaccinated mice (FIG. 22).

These results show that CD8⁺ T cells are featured in the immunity elicited by fusion vaccines of the present invention.

Example 19

Fusion To LLO And Delivery By LM Enhance The Immunogenicity of Her-2

Materials and Experimental Methods

DNA Vaccines

DNA vaccines were constructed using pcDNA 3.1. Her-2 and the EC1 fragment were amplified by PCR using the following primers:

Full length, unfused Her-2: 5'CCGG GCTAGCATGGTCATCATGGAGCTGGCCGG (Nhe I site underlined; SEQ ID No: 37) and 3' CCGGGATATCTTA CTTGTCATCGTCGTCCTTGTAGTCT-CATACAGGTACATCCA GGCC (EcoRV site underlined, FLAG tag in italics, stop codon in bold; SEQ ID No: 38). The above 5' primer was also used for amplifying unfused EC1, and the 3' primer for amplifying ΔLLO—full length Her-2.

ΔLLO-full length Her-2: 5'CCGG GTCGACATGGTCATCATGGAGCTGGCCGG (Sal I site underlined; SEQ ID No: 39). This primer was also used for amplifying ΔLLO-EC1.

Unfused EC1: 3'CCGGGATATCTTA CTTGT-CATCGTCGTCCTTGTA GTCTCAGACCTCTTGGTTAT TCGGGGG (EcoRV site underlined, FLAG tag in italics, stop codon in bold; SEQ ID No: 40). This primer was also used for amplifying unfused EC1 fused to ΔLLO.

Fragments were cloned into the multicloning site of pcDNA3.1, and used to transform Escherichia coli. Bacteria were grown in Luria-Bertani media (BD, Sparks, MD) with 50 micrograms per milliliter (μg/ml) ampicillin.

Tumor Regression Experiments

Tumor regression experiments were performed as described in Example 17, except that 7×10⁵ NT-2 cells were utilized, and vaccinations were administered on days 3, 10, and 18. DNA vaccines (50 μg each of the recombinant pcDNA plasmid+the GM-CSF plasmid; or GM-CSF alone) were administered intra-muscularly and Lm administered intraperitoneally.

Results

Several factors were present in the Lm-ΔLLO-Her-2 vaccines that may have contributed to the recognition of sub-dominant epitopes: (a) delivery by LM; (b) fusion of the target antigen to ΔLLO; (c) breaking Her-2 into fragments. To determine which one or more of these factors contributed to the recognition of sub-dominant epitopes, as evidence by enhanced anti-Her-2 immune responses, mice were vaccinated with (a) pcDNA 3.1-full length Her-2 (a DNA vaccine;

"pcDNA neu"); (b) pcDNA 3.1 ΔLLO-full length Her-2 (pcDNA LLO-neu); (c) pcDNA 3.1-EC1 (pcDNA EC1); (d) pcDNA 3.1-ΔLLO-EC1 (pcDNA LLO-EC1); or (e) Lm-ΔLLO-EC1, and a tumor regression experiment was performed. GM-CSF was included with the DNA vaccines because of its ability to enhance the efficacy of DNA vaccines (McKay P F, Barouch D H et al., Eur J Immunol 2004 April; 34(4): 1011-20.).

Figure 23:
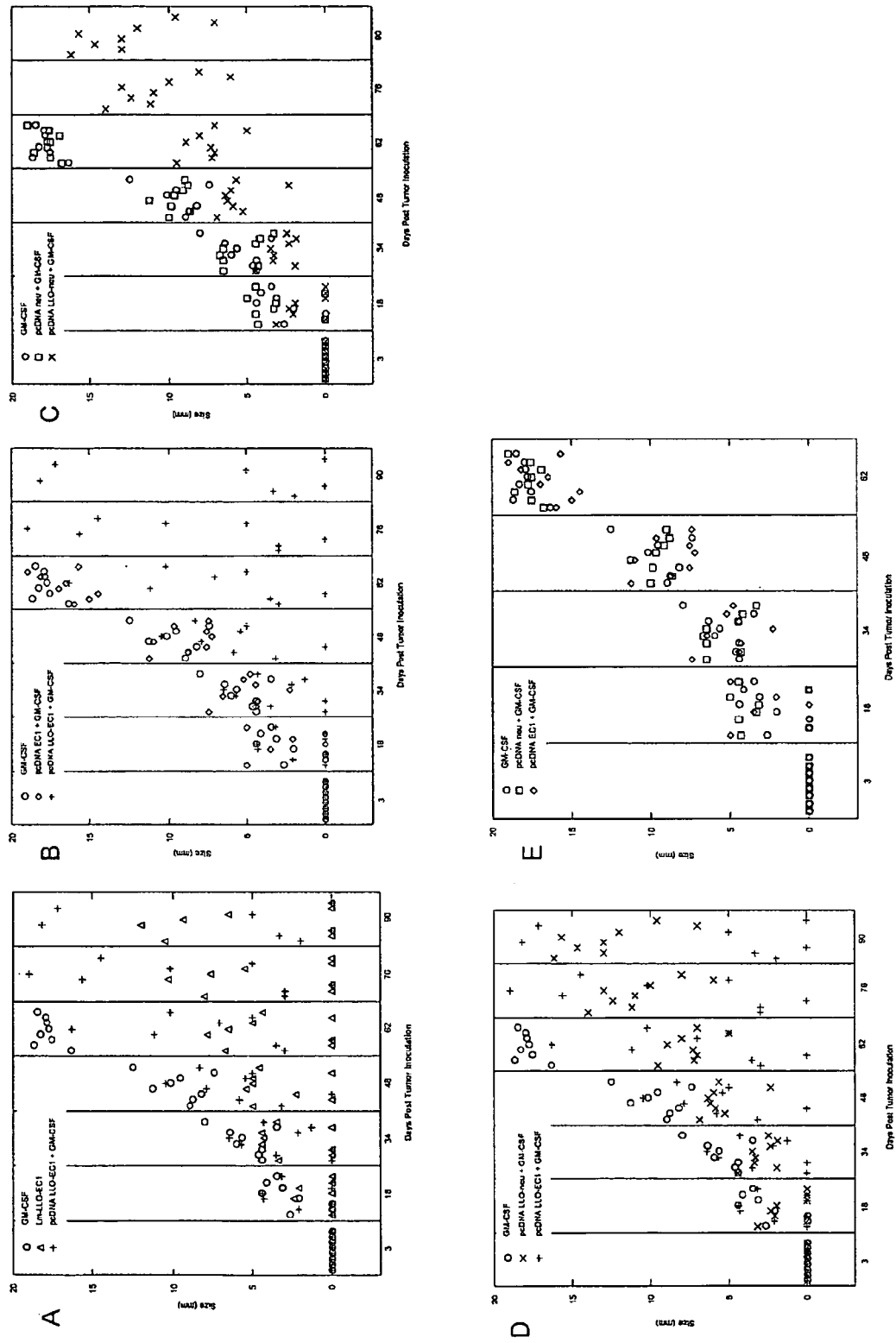
FIG. 23. Delivery by LM and fusion to ΔLLO increases the anti-tumor immune response of Her-2 vaccines using DNA plasmids for delivery. Average tumor diameter for each mouse is depicted. Tumor measurements are shown only for the surviving mice at a given time point. (A) Lm-ΔLLO-EC1 vs. pcDNA ΔLLO-EC1+GM-CSF, (B) pcDNA EC1+GM-CSF vs. pcDNA ΔLLO-EC1+GM-CSF, (C) pcDNA neu+GM-CSF vs. pcDNA ΔLLO-neu+GM-CSF, (D) pcDNA ΔLLO-neu+GM-CSF vs. pcDNA ΔLLO-EC1+GM-CSF, and (E) pcDNA neu+GM-CSF vs. pcDNA EC1+GM-CSF.
Figure 24:
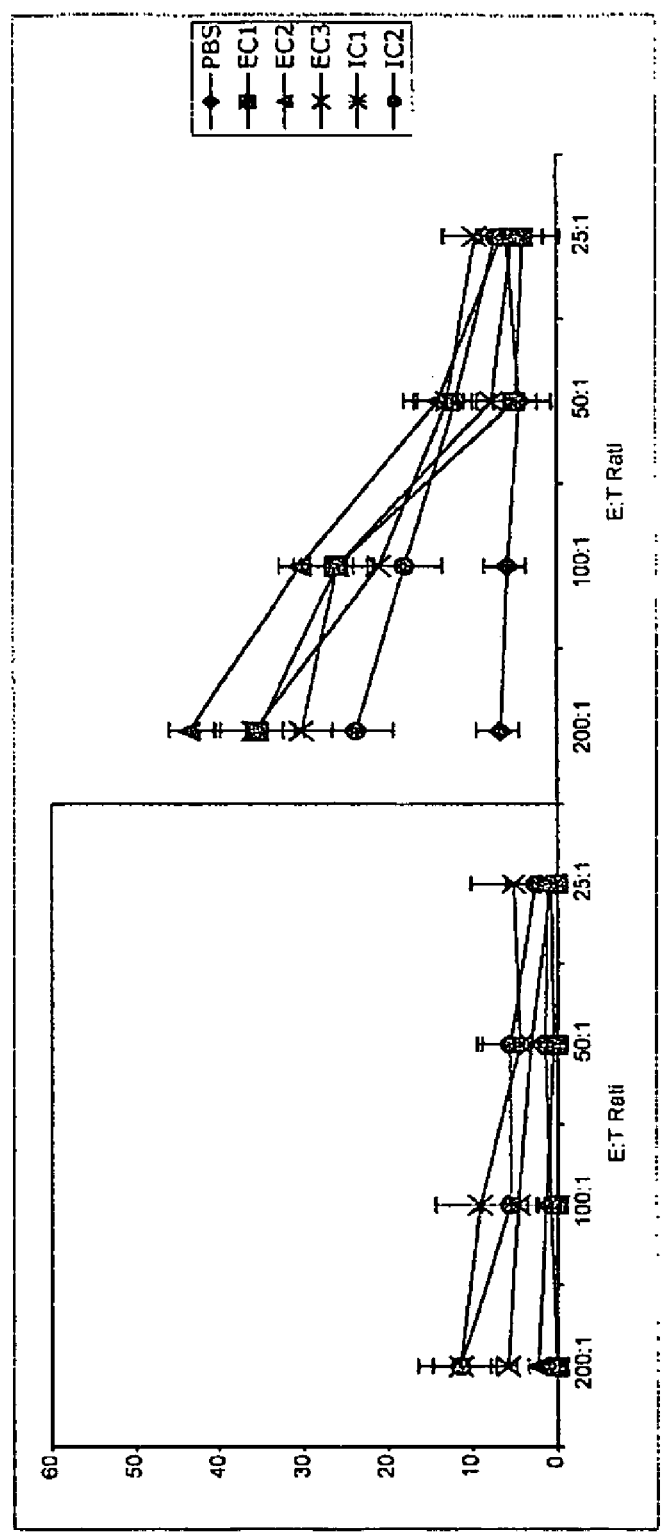
FIG. 24. Each of the Lm-ΔLLO-Her-2 vaccine constructs induces similar levels of anti-Her-2 CTL activity. A. wild type 3T3 (negative control). B. 3T3-neu (full length Her-2). Results are shown as the mean of triplicate cultures, and are representative of 5 experiments.

As depicted in FIG. 23A, the best control of tumor growth was observed with Lm-ΔLLO-EC1; 2/8 of the mice never developed palpable tumors; the tumor completely regressed in another two; and the other 4 mice exhibited slower (retarded) tumor growth than the mock-vaccinated controls. In the case of pcDNA ΔLLO-EC1, one mouse never developed a tumor, and several of the other mice exhibited retarded tumor growth. Fusion to ΔLLO enhanced immunogenicity of EC1, as seen by comparison of pcDNA EC1 vs. pcDNA ΔLLO-EC1 and pcDNA neu vs. pcDNA ΔLLO-neu (FIGS. 24B-C); vaccines in which the antigen was unfused exhibited tumors that grew at the same rate as mock-vaccinated controls. An enhancing effect of dividing Her-2 into smaller fragments, in the case of the ΔLLO fusions, is seen from a comparison of pcDNA ΔLLO-neu vs. pcDNA ΔLLO-EC1, in which the latter group exhibited superior tumor control (FIG. 23D). No effect was seen for the unfused antigens, as seen from a comparison of pcDNA neu vs. pcDNA EC1 (FIG. 23E).

Example 20

Vaccination with LLO-Her-2 Overcomes Immune Tolerance to a Self Antigen

Materials and Experimental Methods

Rat Her-2/neu transgenic mice were purchased form Jackson laboratories and bred in the University of Pennsylvania vivarium. Young, virgin HER-2/neu transgenic mice that had not spontaneously developed tumors were injected with $5 \times 10^4$ NT-2 cells. Because the transgenic mouse is profoundly tolerant to HER-2/neu, the minimum dose required for tumor growth in 100% of animals is much lower than wild-type mice (Reilly R T, Gottlieb M B et al, Cancer Res. 2000 Jul. 1; 60(13): 3569-76). NT-2 cells were injected into the subcutaneous space of the flank. Mice received 0.1 $LD_{50}$ of the *Listeria* vaccine when 4-5 mm palpable tumors were detected (typically on day 7 after tumor implantation) and weekly thereafter, for an additional 4 weeks.

Results

The rat Her-2/neu gene differs from the rat neu by 5-6% of amino acid residues, and thus is immunogenic in the mouse (Nagata Y, Furugen R et al, J. Immunol. 159: 1336-43). A transgenic mouse that over expresses rat Her-2/neu under the transcriptional control of the Mouse Mammary Tumor Virus (MMTV) promoter and enhancer is immunologically tolerant to rat Her-2/neu. These mice spontaneously develop breast cancer. The MMTV promoter also operates in hematopoietic cells, rendering the mice profoundly tolerant to HER-2/neu. This, this mouse is considered to be stringent model for human breast cancer and in general for tumors expressing antigens, such as Her-2/neu, that are expressed at low levels in normal tissue (Muller W. J. (1991) Expression of activated oncogenes in the murine mammary gland: transgenic models for human breast cancer. Canc Metastasis Rev 10: 217-27).

Figure 25:
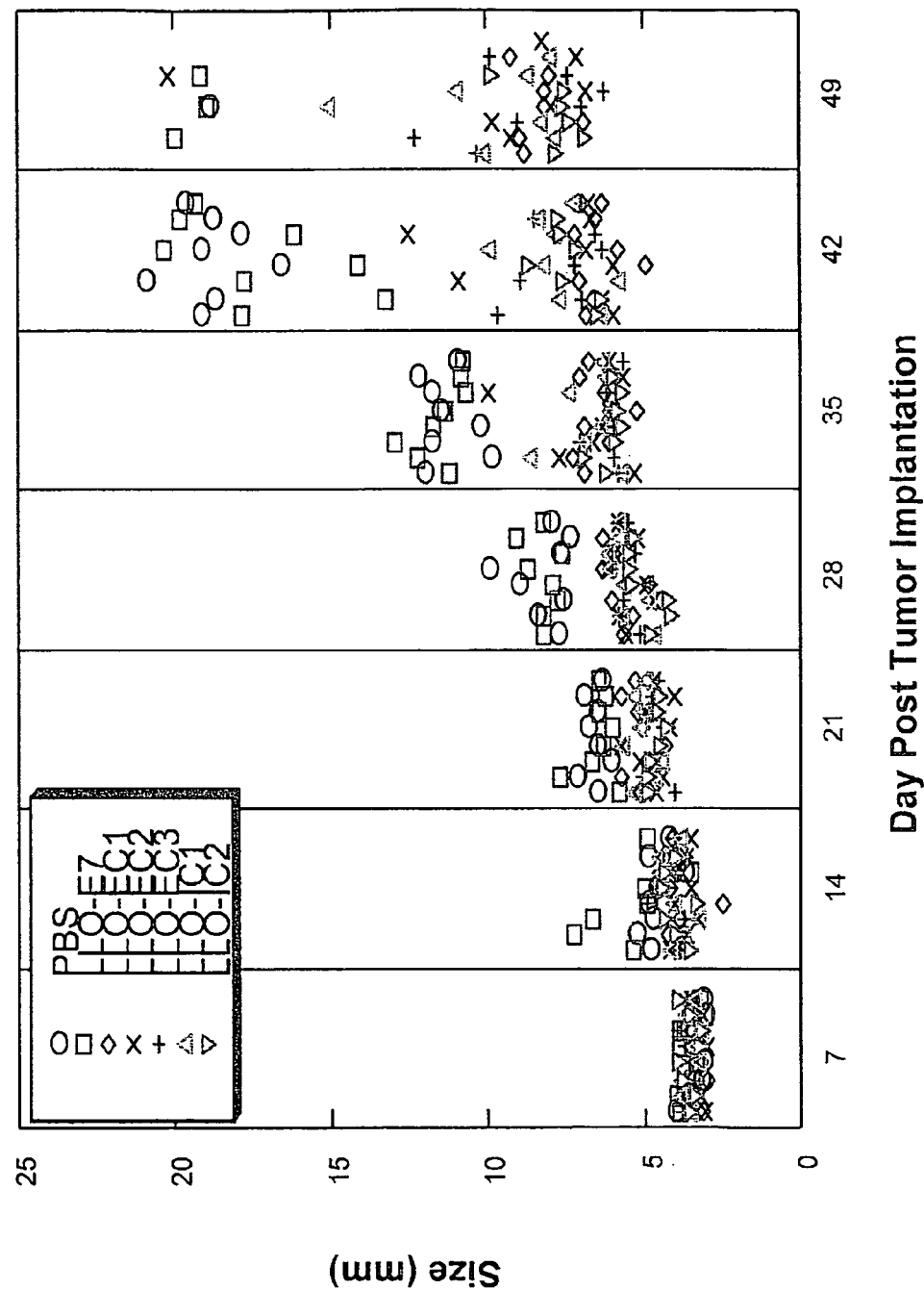
FIG. 25. Lm-ΔLLO-Her-2 vaccines slow the growth of established rat Her-2 expressing tumors in rat Her-2/neu transgenic mice, in which rat Her-2 is expressed as a self-antigen.

6-8 week-old HER-2/neu transgenic mice were injected with NT-2 cells, then immunized with each of the LM-ΔLLO-Her-2 vaccines, or with PBS or ΔLLO-E7 (negative controls). While most control mice had to be sacrificed by day 42 because of their tumor burden, tumor growth was controlled in all of the vaccinated mice (FIG. 25).

Thus, the ΔLM-LLO-Her-2 and *Listeria*-based Her-2 vaccines are able to break tolerance to self antigen expressed on a tumor cell, as evidenced by their ability to induce the regression of established NT-2 tumors. Accordingly, vaccines of the present invention are efficacious for breaking tolerance to self antigen with either Her-2 or E7, showing that findings of the present invention are generalizable to all antigens. In addition, a number of different PEST-like sequences can be used (either LLO or ActA), showing that findings of the present invention are generalizable to all PEST-like sequences.

Example 21

LLO-Her-2 Vaccines Control Spontaneous Tumor Growth in Her-2/Neu Transgenic Mice

Materials and Experimental Methods

ΔLM-LLO-Her-2 vaccines were administered in the following amounts: Lm-LLO-EC1: $1 \times 10^7$ cfu; Lm-Lm-LLO-EC2: $5 \times 10^7$ cfu; LLO-EC3: $1 \times 10^8$ cfu; Lm-LLO-IC2: $1 \times 10^7$ cfu; Lm-LLO-IC1: $1 \times 10^7$.

Results

Figure 26:
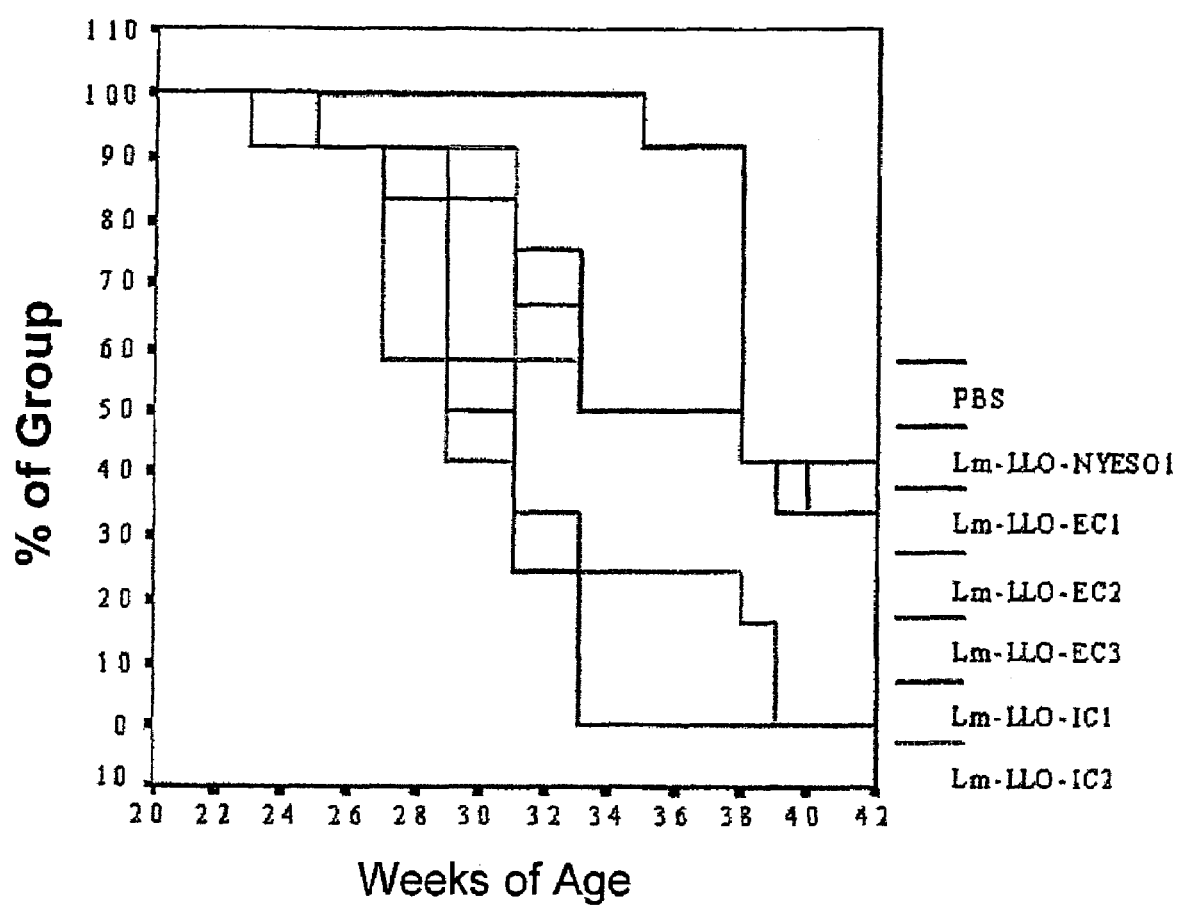
FIG. 26. LLO-Her-2 vaccines control spontaneous tumor growth in Her-2/neu transgenic mice.

The ΔLM-LLO-Her-2 vaccines were also evaluated for ability to prevent spontaneous tumor growth in the Her-2/neu transgenic mice. The transgenic mice (n=12 per vaccine group) were immunized 5 times with 0.1 $LD_{50}$ of one of the vaccine strains, beginning at age 6 weeks and continuing once every three weeks. Mice were monitored for tumor formation in the mammary glands. By week 35, all of the control mice (PBS or Lm-LLO-NY-ESO-1-immunized) had developed tumors. By contrast, 92% of the Lm-LLO-IC1 group were tumor free, as were 50% of the mice Lm-LLO-EC2, Lm-LLO-EC1, and Lm-LLO-IC2, and 25% of the mice immunized with Lm-LLO-EC3 (FIG. 26).

These findings confirm the results of the previous Examples, showing that vaccines of the present invention are able to break tolerance to self antigens and prevent spontaneous tumor growth.

Example 22

Vaccines of the Present Invention Reduce Autochthonous (Spontaneous) Tumors in E6/E7 Transgenic Mice To determine the impact of the Lm-LLO-E7 and Lm-ActA-E7 vaccines on autochthonous tumors in the E6/E7 transgenic mouse, 6 to 8 week old mice were immunized with $1 \times 10^8$ Lm-LLO-E7 or $2.5 \times 10^8$ Lm-ActA-E7 once per month for 8 months. Mice were sacrificed 20 days after the last immunization and their thyroids removed and weighed. The average weight of the thyroids in the vaccinated groups was significantly less than the unvaccinated or mock vaccinated groups (Table 4), showing that the Lm-LLO-E7 and Lm-ActA-E7 vaccines controlled spontaneous tumor growth.

TABLE 4

| Thyroid weight in unvaccinated and vaccinated transgenic mice at 8 months of age (mg). | | | | | | | |
|---|---|---|---|---|---|---|---|
| Untreated | ±S.D. | Lm-LLO-NP | ±S.D. | Lm-LLO-E7 | ±S.D. | Lm-ActA-E7 | ±S.D. |
| 408 | 123 | 385 | 130 | 225 | 54 | 305 | 92 |

Statistical analyses performed using Student's t test showed that the difference in thyroid weight between Lm-LLO-NP treated mice (irrelevant antigen control) and untreated mice was not significant: the difference between Lm-LLO-E7 treated mice and untreated mice was significant (p<0.001) and between Lm-LLO-ActA treated mice and untreated mice was also significant (p<0.05)

Thus, vaccines of the present invention are able to prevent formation of new tumors with either Her-2 or E7, showing that findings of the present invention are generalizable to all antigens. In addition, a number of different PEST-like sequences can be used (either LLO or ActA), showing that findings of the present invention are generalizable to all PEST-like sequences.

What is claimed:

1. A recombinant nucleotide encoding a recombinant polypeptide comprising an N-terminal fragment of an ActA protein consisting of the first 390 amino acids of the *Listeria monocytogenes* ActA protein fused to a tumor antigen or a fragment thereof, wherein said ActA fragment comprises a PEST-like sequence selected from the sequences set forth in SEQ ID No: 2-5 and wherein said tumor antigen is a self antigen.

2. The recombinant nucleotide of claim 1, wherein said self antigen is selected from the group consisting of Her-2/Neu, tyrosinase-related protein (TRP)-2, melanoma antigen (MAGE)-1, MAGE-3, gp-100, tyrosinase, melanoma antigen recognized by T-cells (MART)-1, heat shock protein (HSP)-70, beta-human chorionic gonadotropin (HCG), carcinoembryonic antigen (CEA), the ras protein, the p53 protein, Muc1, and prostate specific antigen (PSA).

3. The recombinant nucleotide of claim 1, wherein said self antigen and said N-terminal fragment of an ActA protein are expressed from a promoter selected from the group consisting of an hly promoter, a prfA promoter, and a p60 promoter.

4. The recombinant nucleotide of claim 1, wherein said *Listeria monocytogenes* is the 10403s strain.

5. A recombinant vector expressing a recombinant polypeptide comprising an N-terminal fragment of an ActA protein consisting of the first 390 amino acids of the *Listeria monocytogenes* ActA protein fused to a tumor antigen or a fragment thereof, wherein said ActA fragment comprises a PEST-like sequence selected from the sequences set forth in SEQ ID No: 2-5 and wherein said tumor antigen is a self antigen.

6. The recombinant vector of claim 5, wherein said self antigen is selected from the group consisting of Her-2/Neu, tyrosinase-related protein (TRP)-2, melanoma antigen (MAGE)-1, MAGE-3, gp-100, tyrosinase, melanoma antigen recognized by T-cells (MART)-1, heat shock protein (HSP)-70, beta-human chorionic gonadotropin (HCG), carcinoembryonic antigen (CEA), the ras protein, the p53 protein, Muc1, and prostate specific antigen (PSA).

7. The recombinant vector of claim 5, wherein said self antigen and said N-terminal fragment of an ActA protein are expressed from a promoter selected from the group consisting of an hly promoter, a prfA promoter, and a p60 promoter.

8. The recombinant vector of claim 5, wherein said *Listeria monocytogenes* is the 10403s strain.

9. A recombinant *Listeria* strain comprising a recombinant nucleotide, said recombinant nucleotide encoding a recombinant polypeptide comprising an N-terminal fragment of an ActA protein consisting of the first 390 amino acids of the *Listeria monocytogenes* ActA protein fused to a tumor antigen or a fragment thereof, wherein said ActA fragment comprises a PEST-like sequence selected from the sequences set forth in SEQ ID No: 2-5 and wherein said tumor antigen is a self antigen.

10. The recombinant *Listeria* strain of claim 9, wherein said self antigen is selected from the group consisting of Her-2/Neu, tyrosinase-related protein (TRP)-2, melanoma antigen (MAGE)-1, MAGE-3, gp-100, tyrosinase, melanoma antigen recognized by T-cells (MART)-1, heat shock protein (HSP)-70, beta-human chorionic gonadotropin (HCG), carcinoembryonic antigen (CEA), the ras protein, the p53 protein, Muc1, and prostate specific antigen (PSA).

11. The recombinant *Listeria* strain of claim 9, wherein said self antigen and said N-terminal fragment of an ActA protein are expressed from a promoter selected from the group consisting of an hly promoter, a prfA promoter, and a p60 promoter.

12. The recombinant *Listeria* strain of claim 9, wherein said *Listeria monocytogenes* is the 10403s strain.

13. A method of killing a cell of a Her-2 transformed tumor comprising administering a recombinant *Listeria* strain comprising a recombinant nucleotide, said recombinant nucleotide encoding a recombinant polypeptide comprising an N-termninal fragment of an ActA protein consisting of the first 390 amino acids of the *Listeria monocytogenes* ActA protein fused to Her-2/Neu tumor antigen or a fragment thereof, wherein said ActA fragment comprises a PEST-like sequence selected from the sequences set forth in SEQ ID NO: 2-5, thereby killing the cell of a Her-2 transformed tumor.

14. A method of reducing the size of a Her-2 transformed tumor comprising administering a recombinant *Listeria* strain comprising a recombinant nucleotide, said recombinant nucleotide encoding a recombinant polypeptide comprising an N-terminal fragment of an ActA protein consisting of the first 390 amino acids of the *Listeria monocytogenes* ActA protein fused to a Her-2/Neu tumor antigen or a fragment thereof, wherein said ActA fragment comprises a PEST-like sequence selected from the sequences set forth in SEQ ID NO: 2-5, thereby reducing the size of said Her-2 transformed tumor.

15. A method of treating a subject having a Her-2 transformed tumor comprising administering to said subject a recombinant *Listeria* strain comprising a recombinant nucleotide, said recombinant nucleotide encoding a recombinant polypeptide comprising an N-terminal fragment of an ActA protein consisting of the first 390 amino acids of the *Listeria monocytogenes* ActA protein fused to a Her-2/Neu tumor antigen or a fragment thereof, wherein said ActA fragment comprises a PEST-like sequence selected from the sequences set forth in SEQ ID NO: 2-5, thereby treating said subject having said Her-2 transformed tumor.

16. A method for overcoming the immune tolerance of a subject to a self antigen-expressing tumor comprising administering to said subject a composition comprising a recombinant *Listeria* strain comprising a recombinant nucleotide, said recombinant nucleotide encoding a recombinant polypeptide comprising an N-terminal fragment of an ActA protein consisting of the first 390 amino acids of the *Listeria monocytogenes* ActA protein fused to a tumor antigen or a fragment thereof, wherein said ActA fragment comprises a PEST-like sequence selected from the sequences set forth in SEQ ID No: 2-5 and wherein said tumor antigen is a self antigen, whereby said subject mounts an immune response against said self-antigen-expressing tumor, thereby overcoming the immune tolerance of said subject to said self-antigen-expressing tumor.

17. A method of suppressing the formation of a self antigen-expressing tumor in a subject comprising administering to said subject a composition comprising a recombinant *Listeria* strain comprising a recombinant nucleotide, said recombinant nucleotide encoding a recombinant polypeptide comprising an N-terminal fragment of an ActA protein consisting of the first 390 amino acids of the *Listeria monocytogenes* ActA protein fused to a tumor antigen or a fragment thereof, wherein said ActA fragment comprises a PEST-like sequence selected from the sequences set forth in SEQ ID No: 2-5 and wherein said tumor antigen is a self antigen, whereby said subject mounts an immune response against said self-antigen-expressing tumor, thereby suppressing the formation of said self-antigen-expressing tumor.

18. A recombinant nucleotide encoding a recombinant polypeptide consisting of a PEST-like sequence selected from the sequences set forth in SEQ ID No: 2-5 fused to a tumor antigen or a fragment thereof, wherein said tumor antigen is a self antigen.

19. The recombinant nucleotide of claim 18, wherein said self antigen is selected from the group consisting of Her-2/Neu, tyrosinase-related protein (TRP)-2, melanoma antigen (MAGE)-1 MAGE-3, gp-100, tyrosinase, melanoma antigen recognized by T-cells (MART)-1, heat shock protein (HSP)-70, beta-human chorionic gonadotropin (HCG), carcinoembryonic antigen (CEA), the ras protein, the p53 protein, Muc1, and prostate specific antigen (PSA).

20. The recombinant nucleotide of claim 18, wherein said self antigen and said PEST-like sequence are expressed from a promoter selected from the group consisting of an hly promoter, a prfA promoter, and a p60 promoter.

21. A recombinant vector expressing a recombinant polypeptide, consisting of a PEST-like sequence selected from the sequences set forth in SEQ ID No: 2-5 fused to a tumor antigen or a fragment thereof, wherein said tumor antigen is a self antigen.

22. The recombinant vector of claim 21, wherein said self antigen is selected from the group consisting of Her-2/Neu, tyrosinase-related protein (TRP)-2, melanoma antigen (MAGE)-1, MAGE-3, gp-100, tyrosinase, melanoma antigen recognized by T-cells (MART)-1, heat shock protein (HSP)-70, beta-human chorionic gonadotropin (HCG) carcinoembryonic antigen (CEA) the ras protein, the p53 protein, Muc1, and prostate specific antigen (PSA).

23. The recombinant vector of claim 21, wherein said self antigen and said PEST-like sequence are expressed from a promoter selected from the group consisting of an hly promoter, a prfA promoter, and a p60 promoter.

24. A recombinant *Listeria* strain comprising a recombinant nucleotide, said recombinant nucleotide encoding a recombinant polypeptide consisting of a PEST-like sequence selected from the sequences set forth in SEQ ID No: 2-5 fused to a tumor antigen or a fragment thereof, wherein said tumor antigen is a self antigen.

25. The recombinant *Listeria* strain of claim 24, wherein said self antigen is selected from the group consisting of Her-2/Neu, tyrosinase-related protein (TRP)-2, melanoma antigen (MAGE)-1, MAGE-3, gp-100, tyrosinase, melanoma antigen recognized by T-cells (MART)-1, heat shock protein (HSP)-70, beta-human chorionic gonadotropin (HCG) carcinoembryonic antigen (CEA) the ras protein, the p53 protein, Muc1, and prostate specific antigen (PSA).

26. The recombinant *Listeria* strain of claim 24, wherein said self antigen and said N-terminal fragment of an ActA protein are expressed from a promoter selected from the group consisting of an hly promoter, a prfA promoter, and a p60 promoter.

27. A method of killing a cell of a Her-2 transformed tumor comprising administering a recombinant *Listeria* strain comprising a recombinant nucleotide, said recombinant nucleotide encoding a recombinant polypeptide consisting of a PEST-like sequence selected from the sequences set forth in SEQ ID NO: 2-5 fused to a Her-2/Neu tumor antigen or a fragment thereof, thereby killing said cell of said Her-2 transformed tumor.

28. A method of reducing the size of a Her-2 transformed tumor comprising administering a recombinant *Listeria* strain comprising a recombinant nucleotide, said recombinant nucleotide encoding a recombinant polypeptide consisting of a PEST-like sequence selected from the sequences set forth in SEQ ID NO: 2-5 fused to a Her-2/Neu tumor antigen or a fragment thereof, thereby reducing the size of said Her-2 transformed tumor.

29. A method of treating a subject having a Her-2 transformed tumor comprising administering to said subject a recombinant *Listeria* strain comprising a recombinant nucleotide, said recombinant nucleotide encoding a recombinant polypeptide consisting of a PEST-like sequence selected from the sequences set forth in SEQ ID NO: 2-5 fused to a Her-2/Neu tumor antigen or a fragment thereof, thereby treating said subject having said Her-2 transformned tumor.

30. A method for overcoming the immune tolerance of a subject to a self antigen-expressing tumor, comprising administering to said subject a composition comprising a recombinant *Listeria* strain comprising a recombinant nucleotide, said recombinant nucleotide encoding a recombinant polypeptide consisting of a PEST-like sequence selected from the sequences set forth in SEQ ID No: 2-5 fused to a tumor antigen or a fragment thereof, wherein said tumor antigen is a self antigen, whereby said subject mounts an immune response against said self-antigen-expressing tumor, thereby overcoming the immune tolerance of said subject to said self-antigen-expressing tumor.

31. A method of suppressing a formation of a self antigen-expressing tumor in a subject, comprising administering to said subject a composition comprising a recombinant *Listeria* strain comprising a recombinant nucleotide said recombinant nucleotide encoding a recombinant polypeptide consisting of a PEST-like sequence selected from the sequences set forth in SEQ ID No: 2-5 fused to a tumor antigen or a fragment thereof, wherein said tumor antigen is a self antigen, whereby said subject mounts an immune response against said self-antigen-expressing tumor, thereby suppressing the formation of said self-antigen-expressing tumor in the subject.

* * * * *

```
                         SEQUENCE LISTING

<160> NUMBER OF SEQ ID NOS: 39

<210> SEQ ID NO 1
<211> LENGTH: 61
<212> TYPE: DNA
<213> ORGANISM: Artificial
<220> FEATURE:
<223> OTHER INFORMATION: primer

<400> SEQUENCE: 1
ccgggatatc ttacttgtca tcgtcgtcct tgtagtctca gacctcttgg ttattcgggg      60
g                                                                     61

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30
```

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
1               5                   10                  15

Lys

<210> SEQ ID NO 8
<211> LENGTH: 27
<212> TYPE: DNA
<213> ORGANISM: Artificial
<220> FEATURE:
<223> OTHER INFORMATION: primer

<400> SEQUENCE: 8
gctagccctc ctttgattag tatattc                                    27

<210> SEQ ID NO 9
<211> LENGTH: 36
<212> TYPE: DNA
<213> ORGANISM: Artificial
<220> FEATURE:
<223> OTHER INFORMATION: primer

<400> SEQUENCE: 9
gcggatgaaa tcgataagca tggagataca cctaca                          36

<210> SEQ ID NO 10
<211> LENGTH: 36
<212> TYPE: DNA
<213> ORGANISM: Artificial
<220> FEATURE:
<223> OTHER INFORMATION: primer

<400> SEQUENCE: 10
cgcctacttt agctattcgt acctctatgt ggatgt                          36

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
gagtctttgg tattgggccc                                            20

<210> SEQ ID NO 12
<211> LENGTH: 19

```
<212> TYPE: DNA
<213> ORGANISM: Artificial
<220> FEATURE:
<223> OTHER INFORMATION: primer

<400> SEQUENCE: 12
gctctagatt atggtttct                                          19

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13 ggggtacccct cctttgatta gtatat                                 26

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14
ggggtctaga cctcctttga ttagtatatt c                            31

<210> SEQ ID NO 15
<211> LENGTH: 45
<212> TYPE: DNA
<213> ORGANISM: Artificial
<220> FEATURE:
<223> OTHER INFORMATION: primer

<400> SEQUENCE: 15
atcttcgcta tctgtcgccg cggcgcgtgc ttcagtttgt tgcgc              45

<210> SEQ ID NO 16
<211> LENGTH: 45
<212> TYPE: DNA
<213> ORGANISM: Artificial
<220> FEATURE:
<223> OTHER INFORMATION: primer

<400> SEQUENCE: 16
gcgcaacaaa ctgaagcagc ggccgcggcg acagatagcg aagat              45

<210> SEQ ID NO 17
<211> LENGTH: 42
<212> TYPE: DNA
<213> ORGANISM: Artificial
<220> FEATURE:
<223> OTHER INFORMATION: primer

<400> SEQUENCE: 17
tgtaggtgta tctccatgct cgagagctag gcgatcaatt tc                 42

<210> SEQ ID NO 18
<211> LENGTH: 42
<212> TYPE: DNA
<213> ORGANISM: Artificial
<220> FEATURE:
<223> OTHER INFORMATION: primer

<400> SEQUENCE: 18
```

-continued

```
<210> SEQ ID NO 19
<211> LENGTH: 42
<212> TYPE: DNA
<213> ORGANISM: Artificial
<220> FEATURE:
<223> OTHER INFORMATION: primer

<400> SEQUENCE: 19
aaacggattt atttagatcc cgggttatgg tttctgagaa ca                              42

<210> SEQ ID NO 20
<211> LENGTH: 42
<212> TYPE: DNA
<213> ORGANISM: Artificial
<220> FEATURE:
<223> OTHER INFORMATION: primer

<400> SEQUENCE: 20
tgttctcaga aaccataacc cgggatctaa ataaatccgt tt                              42

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
gggggtcgac cagctcttct tggtgaag                                              28

<210> SEQ ID NO 22
<211> LENGTH: 9
<212> TYPE: PRT
<213> ORGANISM: Human papillomavirus type 16

<400> SEQUENCE: 22

Arg Ala His Tyr Asn Ile Val Thr Phe
1               5

<210> SEQ ID NO 23
<211> LENGTH: 416
<212> TYPE: PRT
<213> ORGANISM: Listeria monocytogenes

<400> SEQUENCE: 23

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
```

```
            115                 120                 125
Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 24
<211> LENGTH: 529
<212> TYPE: PRT
<213> ORGANISM: Listeria monocytogenes

<400> SEQUENCE: 24

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65              70                  75                  80
```

-continued

```
Asp Ala Val Thr Asn Val Pro Pro Arg Lys Gly Tyr Lys Asp Gly Asn
                 85                  90                  95
Glu Tyr Ile Val Val Glu Lys Lys Lys Ser Ile Asn Gln Asn Asn
            100                 105                 110
Ala Asp Ile Gln Val Val Asn Ala Ile Ser Ser Leu Thr Tyr Pro Gly
        115                 120                 125
Ala Leu Val Lys Ala Asn Ser Glu Leu Val Glu Asn Gln Pro Asp Val
    130                 135                 140
Leu Pro Val Lys Arg Asp Ser Leu Thr Leu Ser Ile Asp Leu Pro Gly
145                 150                 155                 160
Met Thr Asn Gln Asp Asn Lys Ile Val Val Lys Asn Ala Thr Lys Ser
                165                 170                 175
Asn Val Asn Asn Ala Val Asn Thr Leu Val Glu Arg Trp Asn Glu Lys
            180                 185                 190
Tyr Ala Gln Ala Tyr Pro Asn Val Ser Ala Lys Ile Asp Tyr Asp Asp
        195                 200                 205
Glu Met Ala Tyr Ser Glu Ser Gln Leu Ile Ala Lys Phe Gly Thr Ala
    210                 215                 220
Phe Lys Ala Val Asn Asn Ser Leu Asn Val Asn Phe Gly Ala Ile Ser
225                 230                 235                 240
Glu Gly Lys Met Gln Glu Val Ile Ser Phe Lys Gln Ile Tyr Tyr
                245                 250                 255
Asn Val Asn Val Asn Glu Pro Thr Arg Pro Ser Arg Phe Phe Gly Lys
            260                 265                 270
Ala Val Thr Lys Glu Gln Leu Gln Ala Leu Gly Val Asn Ala Glu Asn
        275                 280                 285
Pro Pro Ala Tyr Ile Ser Ser Val Ala Tyr Gly Arg Gln Val Tyr Leu
    290                 295                 300
Lys Leu Ser Thr Asn Ser His Ser Thr Lys Val Lys Ala Ala Phe Asp
305                 310                 315                 320
Ala Ala Val Ser Gly Lys Ser Val Ser Gly Asp Val Glu Leu Thr Asn
                325                 330                 335
Ile Ile Lys Asn Ser Ser Phe Lys Ala Val Ile Tyr Gly Gly Ser Ala
            340                 345                 350
Lys Asp Glu Val Gln Ile Ile Asp Gly Asn Leu Gly Asp Leu Arg Asp
        355                 360                 365
Ile Leu Lys Lys Gly Ala Thr Phe Asn Arg Glu Thr Pro Gly Val Pro
    370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
            420                 425                 430
Ile Ser Trp Asp Glu Val Asn Tyr Asp Pro Glu Gly Asn Glu Ile Val
        435                 440                 445
Gln His Lys Asn Trp Ser Glu Asn Asn Lys Ser Lys Leu Ala His Phe
    450                 455                 460
Thr Ser Ser Ile Tyr Leu Pro Gly Asn Ala Arg Asn Ile Asn Val Tyr
465                 470                 475                 480
Ala Lys Glu Cys Thr Gly Leu Ala Trp Glu Trp Trp Arg Thr Val Ile
                485                 490                 495
Asp Asp Arg Asn Leu Pro Leu Val Lys Asn Arg Asn Ile Ser Ile Trp
```

```
                        500                 505                 510
Gly Thr Thr Leu Tyr Pro Lys Tyr Ser Asn Lys Val Asp Asn Pro Ile
        515                 520                 525
Glu

<210> SEQ ID NO 25
<211> LENGTH: 441
<212> TYPE: PRT
<213> ORGANISM: Listeria monocytogenes

<400> SEQUENCE: 25

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
```

```
                340             345             350
Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 26
<211> LENGTH: 47
<212> TYPE: DNA
<213> ORGANISM: Artificial
<220> FEATURE:
<223> OTHER INFORMATION: primer

<400> SEQUENCE: 26
cacgcggatg aaatcgataa gctcgagccc cccggaatcg cgggcac                  47

<210> SEQ ID NO 27
<211> LENGTH: 38
<212> TYPE: DNA
<213> ORGANISM: Artificial
<220> FEATURE:
<223> OTHER INFORMATION: primer

<400> SEQUENCE: 27
ccggactagt gacctcttgg ttattcgggg gacacacc                            38

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
ccgggtcgac tgcccctaca actacctgtc tacg                                34

<210> SEQ ID NO 29
<211> LENGTH: 42
<212> TYPE: DNA
<213> ORGANISM: Artificial
<220> FEATURE:
<223> OTHER INFORMATION: primer

<400> SEQUENCE: 29
ccggactagt ttacttgtca tcgtcgtcct tgtagtcccc ac                       42

<210> SEQ ID NO 30
<211> LENGTH: 34
<212> TYPE: DNA
<213> ORGANISM: Artificial
<220> FEATURE:
<223> OTHER INFORMATION: primer

<400> SEQUENCE: 30
ccgggtcgac tgctttgtac acactgtacc ttgg                                34
```

<210> SEQ ID NO 31
<211> LENGTH: 58
<212> TYPE: DNA
<213> ORGANISM: Artificial
<220> FEATURE:
<223> OTHER INFORMATION: primer

<400> SEQUENCE: 31
ccggactagt ttacttgtca tcgtcgtcct tgtagtccgg gctggctctc tgctctgc        58

<210> SEQ ID NO 32
<211> LENGTH: 35
<212> TYPE: DNA
<213> ORGANISM: Artificial
<220> FEATURE:
<223> OTHER INFORMATION: primer

<400> SEQUENCE: 32
ccggctcgag tatacgatgc gtaggctgct gcagg        35

<210> SEQ ID NO 33
<211> LENGTH: 34
<212> TYPE: DNA
<213> ORGANISM: Artificial
<220> FEATURE:
<223> OTHER INFORMATION: primer

<400> SEQUENCE: 33
ccggactagt agccagtgga gatctggggg gccc        34

<210> SEQ ID NO 34
<211> LENGTH: 32
<212> TYPE: DNA
<213> ORGANISM: Artificial
<220> FEATURE:
<223> OTHER INFORMATION: primer

<400> SEQUENCE: 34
ccggctcgag ggtgacctgg tagacgctga ag        32

<210> SEQ ID NO 35
<211> LENGTH: 32
<212> TYPE: DNA
<213> ORGANISM: Artificial
<220> FEATURE:
<223> OTHER INFORMATION: primer

<400> SEQUENCE: 35
ccggactagt tacaggtaca tccaggccta gg        32

<210> SEQ ID NO 36
<211> LENGTH: 9
<212> TYPE: PRT
<213> ORGANISM: homo

<400> SEQUENCE: 36

Pro Asp Ser Leu Arg Asp Leu Val Phe
1               5

<210> SEQ ID NO 37
<211> LENGTH: 33
<212> TYPE: DNA
<213> ORGANISM: Artificial
<220> FEATURE:
<223> OTHER INFORMATION: primer -continued

```
<400> SEQUENCE: 37
ccgggctagc atggtcatca tggagctggc cgg                                33

<210> SEQ ID NO 38
<211> LENGTH: 58
<212> TYPE: DNA
<213> ORGANISM: Artificial
<220> FEATURE:
<223> OTHER INFORMATION: primer

<400> SEQUENCE: 38
ccgggatatc ttacttgtca tcgtcgtcct tgtagtctca tacaggtaca tccaggcc    58

<210> SEQ ID NO 39
<211> LENGTH: 33
<212> TYPE: DNA
<213> ORGANISM: Artificial
<220> FEATURE:
<223> OTHER INFORMATION: primer

<400> SEQUENCE: 39
ccgggtcgac atggtcatca tggagctggc cgg                                33
```